(12) United States Patent
Zou et al.

(10) Patent No.: US 8,658,855 B2
(45) Date of Patent: Feb. 25, 2014

(54) DIACYLGLYCEROL ACYLTRANSFERASE 2 GENES AND PROTEINS ENCODED THEREBY FROM ALGAE

(75) Inventors: Jitao Zou, Saskatoon (CA); Jingyu Xu, Saskatoon (CA); Zhifu Zheng, Zionsville, IN (US)

(73) Assignees: National Research Council of Canada, Ottawa, Ontario (CA); Dow AgroSciences LLC, Indianapolis, IN (US)

( * ) Notice: Subject to any disclaimer, the term of this patent is extended or adjusted under 35 U.S.C. 154(b) by 372 days.

(21) Appl. No.: 12/735,132

(22) PCT Filed: Dec. 16, 2008

(86) PCT No.: PCT/US2008/013811
§ 371 (c)(1),
(2), (4) Date: Nov. 4, 2010

(87) PCT Pub. No.: WO2009/085169
PCT Pub. Date: Jul. 9, 2009

(65) Prior Publication Data
US 2011/0061130 A1    Mar. 10, 2011

Related U.S. Application Data

(60) Provisional application No. 61/008,742, filed on Dec. 21, 2007.

(51) Int. Cl.
| | |
|---|---|
| *C12N 15/05* | (2006.01) |
| *C12N 15/81* | (2006.01) |
| *C12N 15/82* | (2006.01) |
| *A01H 5/00* | (2006.01) |
| *A01H 5/10* | (2006.01) |
| *C12P 7/64* | (2006.01) |
| *C12N 9/10* | (2006.01) |
| *C12N 1/00* | (2006.01) |
| *C12N 5/04* | (2006.01) |
| *C07H 21/04* | (2006.01) |

(52) U.S. Cl.
USPC ........... 800/281; 800/295; 800/306; 435/134; 435/193; 435/255.1; 435/410; 536/23.2

(58) Field of Classification Search
None
See application file for complete search history.

(56) References Cited

U.S. PATENT DOCUMENTS

| | | | |
|---|---|---|---|
| 7,105,723 B2 * | 9/2006 | Haertel et al. | 800/298 |
| 2005/0130284 A1 | 6/2005 | Milcamps et al. | |
| 2006/0094088 A1 | 5/2006 | Picataggio et al. | |

FOREIGN PATENT DOCUMENTS

WO    WO 2009/085169 A2    12/2008

OTHER PUBLICATIONS

Richardson et al Dec. 12, 2007 GenBank: FC532806.1.*
Guo et al 2004 PNAS 101: p. 9205-9210.*
Dubois et al 2007 Eur. J. Lipid Sci. Technol. 109: p. 710-732.*
Richardson et al Dec. 12, 2007, GenBank: FC532806.1.*
PCT International Search Report, PCT/US2008/13811 dated May 12, 2009.
PCT Written Opinion for PCT/US2008/13811 dated Apr. 22, 2009.
Armbrust et al., The genome of the diatom *Thalassiosira pseudonana*: Ecology, evolution and metabolism, Science, Oct. 1, 2004, pp. 79-85, vol. 306.
Tonon et al., Long chain polyunsaturated fatty acid production and partitioning to triacylglycerols in four microalgae, Phytochemistry, 2002, pp. 15-24, vol. 61.
Database UniProt [Online] XP002627492, Database accession No. A8IXB2, printed May 11, 2010.
Supplementary European Search Report, EP 08 86 8776, dated Mar. 10, 2011.

* cited by examiner

*Primary Examiner* — Brent T Page
*Assistant Examiner* — Matthew Keogh
(74) *Attorney, Agent, or Firm* — TraskBritt

(57) ABSTRACT

The present disclosure relates to the isolation, purification, and characterization of a diacylglycerol acyltransferase 2 (DGAT2), and genes encoding DGAT2, from algae. DGAT2 can incorporate very long chain polyunsaturated fatty acids in to triacylglycerol more efficiently than DGAT1. The disclosure concerns methods of regulating seed oil content, fatty acid synthesis and fatty acid composition using the DGAT2 gene and to tissues and plants transformed with the gene. The disclosure also relates to transgenic plants, plant tissues and plant seeds having a genome containing an introduced DNA sequence of the disclosure, and a method of producing such plants and plant seeds.

19 Claims, 9 Drawing Sheets

FIG 1A

```
TpDGA2-Pro         M   T   T   K   K   R   P   K   P   R   H   K   H   L
TpDGA2-DNA    1  atg aca aca aag aag cgt cca cta ccc cgt cat ctg cac ctt
                   P   P   G   V   E   V   L   V   S   P   P   P   Y   E
             43  cca cct gga gta gaa gta ctc gtc tct cca cca ccc tac gaa
                   V   C   T   L   V   D   R   L   L   V   Y   A   S   S
             85  gta tgc acg ctc gtc gac aga ttg ttg gtc tac gcc tcg tcg
                   L   I   V   V   G   S   P   V   W   F   Y   G   G   I
            127  ttg att gtc gtt gga tct ccc gtt tgg ttc tac gga ggc atc
                   I   Y   F   Y   R   K   W   K   L   Y   R   S   K   A
            169  att tat ttt tac agg aag tgg aag aag tat cgt tct ctt gct
                   A   A   T   F   A   A   R   H   E   S   G   G   G   G
            211  gct gct act gag gct gcg aga cat gag agt ggt ggc ggt ggt
                   A   S   S   T   V   R   C   R   G   T   R   Q   R   T
            253  gca tcg tca acg gtt cgt tgc aga ggt aca cgt caa cgt aca
                   S   S   D   D   G   N   Y   T   S   S   T   G   E   S
            295  tcg tct gat gac ggc aac tac aca tcg tca act ggc gaa agc
                   S   Q   E   M   N   E   Q   E   T   Q   T   Q   S   H
            337  tcg caa gaa atg aac gaa caa gag aca caa aca caa tca cat
                   R   Q   Q   T   E   Q   Y   N   N   Y   K   R   L   A
            379  cga caa caa aca gag caa tac aac aac tac aaa cga tta gca
                   T   R   Y   G   V   A   K   A   A   I   I   K   I   S
            421  aca aga tac gga gta gca ctc gct gca atc att ctc ata tcc
                   I   W   G   P   H   R   D   K   R   V   G   E   W   L
            463  atc tgg ggg cct cat cgt gac aag cgt gta gga gaa tgg ctc
                   G   V   K   K   W   R   L   W   D   A   W   L   N   Y
            505  ggt gtc aag aag tgg aga ttg tgg gat gca tgg ttg aac tat
                   V   G   F   T   V   L   K   D   N   G   D   D   D   H
            547  gtt gga ttc act gta cta aag gac aat gga gat gat gac cac
                   T   I   I   E   T   N   P   H   S   A   I   P   N   Q
            589  aca ata ata caa acg aat cca cac tca gca ata ccc aat caa
                   E   E   F   D   I   H   T   S   P   S   I   F   A   F
            631  gaa gag ttt gac ata cac aca tct cca tca atc ttc gca ttc
                   V   P   H   G   I   F   P   F   G   L   A   F   S   C
            673  gta ccc cac ggc atc ttt cct ttc gga ctc gcc ttt tca tgt
                   L   P   E   R   G   H   E   Q   T   W   G   L   F   R
            715  cta ccc gaa cga gga cac gaa caa aca tgg ggt ctc ttc cga
                   P   V   V   A   T   A   T   K   L   F   P   L   V   R
            757  cca gtc gtt gca aca gcc acc aaa ctc ttt ccg ctg gta cga
                   T   F   I   S   W   M   N   G   V   D   A   S   D   S
            799  acc ttc att tct tgg atg aac gga gtg gat gct tcg cgt tcg
                   A   V   S   R   A   L   A   P   P   Y   T   S   D   H
            841  gcg gtg tct cgt gct ctt gct cct ccg tat acc agt gat cat
                   P   G   R   V   G   V   S   P   G   G   I   A   E   M
            883  ccg gga aga gtg gga gtt tcg ccc ggt ggt att gcc gag atg
                   F   E   T   Y   P   K   P   G   F   H   P   N   D   E
            925  ttt gag acg tat cca aag ccg ggg ttt cat cct aat gac gag
                   A   A   L   L   K   D   R   N   G   L   F   K   L   A
            967  gca gca ttg tta aaa gat cgg aat gga ttg ttc aag ctt gcg
                   M   K   H   K   L   P   I   V   P   V   Y   C   F   G
           1009  atg aaa cac aag ctg ccg att gtt ccg gtg tac tgc ttt gga
                   A   T   K   M   L   R   R   V   Q   L   P   A   F   V
           1051  gct aca aag atg ttg aga cga gtg caa tta cct gcg ttt gtg
                   E   T   L   S   R   M   L   K   I   S   L   C   L   F
           1093  gag acg ttg agc aga atg ctc aag atc agt ctt tgt tta ttc
```

FIG 1B

```
           F   G   K   L   G   L   P   I   P   F   R   Q   R   L
      1135 ttt gga aag ctt ggg ttg cct att cct ttc cga cag cgg ctg
           M   Y   V   M   G   K   T   L   F   P   P   L   P   R
      1177 atg tat gtc atg ggc aag acg ttg ttt cct cct ctg ccg aga
           D   G   V   N   T   S   M   M   E   G   G   E   E   F
      1219 gat ggc gtg aac act tct atg atg gaa gga gga gaa gaa ttt
           D   G   R   V   Q   E   M   H   D   A   F   C   N   E
      1261 gat gaa cga gtg caa gag atg cat gat gca ttc tgc aat gag
           I   T   R   I   F   E   R   N   K   D   H   Y   G   W
      1303 ata act cgc atc ttc gag cga aac aaa gac cac tac ggt tgg
           G   N   K   N   L   R   L   V
      1345 ggt aac aaa aac ttg aga ctc gta tga gag tgt gag tga tat 1387 tca tat gca act ctt aac tta aag cca cag acc aca cag gca 1429 caa a
```

FIG 2A

| | | |
|---|---|---|
| TpDGA2 | 1 | MTTKKRPKPRHKHLPPGVEVLVSPPPYEVCTLVDRLLVYA |

| | | |
|---|---|---|
| TpDGA2 | 41 | SSLIVVGSPVWFYGGIIYFYRKWKLYRSKAAATFAARHES |

| | | |
|---|---|---|
| TpDGA2 | 81 | GGGGASSTVRCRGTRQRTSSDDGNYTSSTGESSQEMNEQE |

| | | |
|---|---|---|
| TpDGA2 | 121 | TQTQSHRQQTEQYNNYKRLATRYGVAKAAIIKISIWGPHR |
| 37182187 | 1 | PKK |

| | | |
|---|---|---|
| TpDGA2 | 161 | DKRVGEWLGVKKWRLWDAWLNYVGFTVLKDNGDDD---HT |
| 37182187 | 4 | GGRRSQW--VRNWAVWRHFANYFPVTLIKE-FDLDPKGNY |
| 50541689 | 1 | RRSQW--VRNWAVWRYFRDYFPIQLVKT--------HN |
| 74623358 | 1 | VRKLPLWKHFANYFPVTLIKE-FDLDPKGNY |

| | | |
|---|---|---|
| TpDGA2 | 201 | IIETNPHSAIPNQEEFDIHTSPS-IFAFVPHGIFPFG--- |
| 37182187 | 44 | LLTTRNY----------------IFGYHPHGIMGLG--- |
| 50541689 | 41 | LLTSRNY----------------IFGYHPHGIMGLG--- |
| 74623358 | 41 | IMSYHPHGII-----------S-MAAFANFATEATG--- |
| 74623359 | 1 | KEADLDPSKNYIFGYHPHGIISMGSF- |
| 86279638 | 1 | VFGYEPHSVFPIGVMI |
| 62825813 | 1 | VFGYEPHSVFPLG--- |

| | | |
|---|---|---|
| TpDGA2 | 241 | LAFSCLPERGHE--QTWGLFRPVVATATKL-F--PLVRTF |
| 37182187 | 84 | -AFCNFSTEATEVSKKFPGIRPYLATLAGN-FRMPVLREY |
| 50541689 | 81 | -AFCNFSTEATEVSKKFPGIRPYLATLAGN-FRMPVLREY |
| 74623358 | 81 | FS---------E--QYPGIVPSLLTLASNFRL--PLYRDF |
| 74623359 | 41 | CTFST-NATGFD--DLFPGIRPSLLTLTSN-PNIPLYRDY |
| 86279638 | 41 | LSLGLIPLPN---------IKFLASSAVFY-T--PFLRHI |
| 62825813 | 41 | V--SVLSDHFAV--LPLPKMKVLASNAVFR-T--PVLRHI |

| | | |
|---|---|---|
| TpDGA2 | 281 | ISWMNGVDASDSAVSRALAPPYTSDHPGR-VGVSPGGIAE |
| 37182187 | 124 | LMSGGICPVSRDTIDYLLSKNGSGN---A-IIIVGGAAE |
| 50541689 | 121 | LMSGGICPVNRDTIDYLLSKNGSGN---A-IIIVGGAAE |
| 74623358 | 121 | M-----MSLGMCSVSRHSCEAILRSGPGRSIVIVTGGASE |
| 74623359 | 81 | LMACGLCSVSKTSCQNIL----TKGGPGRSIAIVVGGASE |
| 86279638 | 81 | WSWCGLTPATRKNFVSLLSSGYSCI-------LVPGGVQE |
| 62825813 | 81 | WTWCGLTSATKKNFTALLASGYSCI-------VIPGGVQE |

| | | |
|---|---|---|
| TpDGA2 | 321 | MFETYPKPGFHPNDEAALLKDRNGLFKLAMKHKLPIVPVY |
| 37182187 | 164 | SLSSMP------GKNAVTLRNRKGFVKLALRHGADLVPIY |
| 50541689 | 161 | SLSSMP------GKNAVTLRNRKGFVKLALRHGADLVPTY |
| 74623358 | 161 | SLSA------RPGTNDLTLKKRLGFIRLAIRNGASLVPIF |
| 74623359 | 121 | SLNA------RPGVMDLVLKRRFGFIKIAVQTGASLVPTI |
| 86279638 | 121 | TF--YMKQ----DSEIAFLKARRGFIRIAMQTGTPLVPVF |
| 62825813 | 121 | TF--YMKHG----SEIAFLKARRGFVRVAMEMGKPLVPVF |

FIG 2B

```
TpDGA2     361  CFGATKMLR--RVQ------LPA------FVETLSRMLKI
37182187   204  SFGENEVYK--QVI------FEEGSWGRWVQKKFQKYIGF
50541689   201  SFGENEVYK--QVI------FEEGSWGRWVQKKFQKYIGF
74623358   201  SFGENDIYE--QYDNKKGSLIWR------YQRWFQKITGF
74623359   161  SFGENELYE--QIESNENSKLHR------WQKKIQHALGF
86279638   161  CFGQMHTFKWWKPD------GEL------FMK-IARAIKF
62825813   161  CFGQSNVYKWWKPD------GEL------FMK-IARAIKF

TpDGA2     401  SLCL-----FFGK-------LGLPIPFRQRLMYVMGKTLF
37182187   244  APCI-----FHGRGLFSSDTWGL-VPYSKPITTVVGEPIT
50541689   241  APCI-----FHGRGL---------VPYSKPITTVVGEPI-
74623358   241  TVPLAHARGIFNY-------NAGGIPFRHPIVTVVGKPIA
74623359   201  TMPL-----FHGRGVFNYD-FGL-LPHRHPIYTIVGKPI-
86279638   201  TPTI-----FWGV-------LGTPLPFKNPMHVVVGRPI-
62825813   201  SPIV-----FWGV-------LGSHLPLQRPMHVVVGKPI-

TpDGA2     441  PPLPRDGVNTSMMEGGEEFDGRVQEMHDAFCNEITRIFER
37182187   284  IP---------KLEHPTQQD--IDLYHTMYMEALVKLFDK
50541689   281  -TIPR-------LERPTQQD--IDLHAMYVQALVKLFDQ
74623358   281  VPLLAEGET-------EPSEEQMHQVQAQYIESLQAIYDK
74623359   241  -PVPS-------IKYGQTKDEIIRELHDSYMHAVQDLYDR
86279638   241  ------EVKQNPQPTAEE----VAEVQREFIASLKNLFER
62825813   241  ----------EVKQNPQPTVEEVSEVQGQFVAALKDLFER

TpDGA2     481  NKDHYGWGNKNLRLV
37182187   324  HKTKFG
50541689   321  HKTKFG
74623358   321  YKDIY
74623359   281  YKDIYHKTKFG
86279638   281  HKARVGYSDLKLEI
62825813   281  HKARVGYADLTLEIL
```

FIG 3A

```
  1 MTTKKRPKPRHKHLPPGVEVLVSPPPYEVCTLVDRLLVYA
 41 SSLIVVGSPVWFYGGIIYFYRKWKLYRSKAAATFAARHES
 81 GGGGASSTVRCRGTRQRTSSDDGNYTSSTGESSQEMNEQE
121 TQTQSHRQQTEQYNNYKRLATRYGVAKAAIIKISIWGPHR
161 DKRVGEWLGVRKWRLWDAWLNYVGFTVLKDNGDDDHTIIE
201 TNPHSAIPNQEEFDIHTSPSIFAFVPHGIPPFGLAFSCLP
241 ERGHEQTWGLFRPVVATATKLFPLVRTFISWMNGVDASDS
281 AVSRALAPPYTSDHPGRVGVSPGGIAEMFETYPKPGFHPN
321 DEAALLKDRNGLFKLAMKHKLPIVPVYCFGATKMLRRVQL
361 PAFVETLSRMLKISLCLFFGKLGLPIPFRQRLMYVMGKTL
401 FPPLPRDGVNTSMMEGGEEFDGRVQEMHDAFCNEITRIFE
441 RNKDHYGWGNKNLRLV
```

FIG 3B

```
169   G    V    R    K    W    R    L    W    D    A    W    L    N    Y
505  ggt  gtc  agg  aag  tgg  aga  ttg  tgg  gat  gca  tgg  ttg  aac  tat
```

FIG 4A

```
  1 MTTKKRPKPRHKHLPPGVEVLVSPPPYEVCTLVDRLLVYA
 41 SSLIVVGSPVWFYGGIIYFYRKWKLYRSKAAATFAARHES
 81 GGGGASSTVRCRGTRQRTSSDDGNYTSSTGESSQEMNEQE
121 TQTQSHRQQTEQYNNYKRLATRYGVAKAAIIKISIWGPHR
161 DKRVGEWLGVKKWRLWDAWLNYVGFTVLKDNGDDDHTIIE
201 TNPHSAIPNQEEFDIHTSPSIFAYVPHGIPPFGLAFSCLP
241 ERGHEQTWGLFRPVVATATKLFPLVRTFISWMNGVDASDS
281 AVSRALAPPYTSDHPGRVGVSPGGIAEMFETYPKPGFHPN
321 DEAALLKDRNGLFKLAMKHKLPIVPVYCFGATKMLRRVQL
361 PAFVETLSRMLKISLCLFFGKLGLPIPFRQRLMYVMGKTL
401 FPPLPRDGVNTSMMEGGEEFDGRVQEMHDAFCNEITRIFE
441 RNKDHYGWGNKNLRLV
```

FIG 4B

```
211   E    E    F    D    I    H    T    S    P    S    I    F    A    Y
631  gaa  gag  ttt  gac  ata  cac  aca  tct  cca  tca  atc  ttc  gca  tac
```

FIG 5A

```
  1 MTTKKRPKPRHKHLPPGVEVLVSPPPYEVCTLVDRLLVYA
 41 SSLIVVGSPVWFYGGIIYFYRKWKLYRSKAAATFAARHES
 81 GGGGASSTVRCRGTRQRTSSDDGNYTSSTGESSQEMNEQE
121 TQTQSHRQQTEQYNNYKRLATRYGVAKAAIIKISIWGPHR
161 DKRVGEWLGVKKWRLWDAWLNYVGFTVLKDNGDDDHTIIE
201 TNPHSAIPNQEEFDIHTSPSIFAFVPHGIFPFGLAFSCLP
241 ERGHEQTWGLFRPVVATATKLFPLVRTFISWMNGVDASDS
281 AVSRALAPPYTSDHPGRIGVSPGGIAEMFETYPKPGFHPN
321 DEAALLKDRNGLFKLAMKHKLPIVPVYCFGATKMLRRVQL
361 PAFVETLSRMLKISLCLFFGKLGLPIPFRQRLMYVMGKTL
401 FPPLPRDGVNTSMMEGGEEFDGRVQEMHDAFCNEITRIFE
441 RNKDHYGWGNKNLRLV
```

FIG 5B

```
295   P    G    R    I    G    V    S    P    G    G    I    A    E    M
883  ccg  gga  aga  atc  gga  gtt  tcg  ccc  ggt  ggt  att  gcc  gag  atg
```

FIG 6A

```
  1 MTTKKRPKPRHKHLPPGVEVLVSPPPYEVCTLVDRLLVYA
 41 SSLIVVGSPVWFYGGIIYFYRKWKLYRSKAAATFAARHES
 81 GGGGASSTVRCRGTRQRTSSDDGNYTSSTGESSQEMNEQE
121 TQTQSHRQQTEQYNNYKRLATRYGVAKAAIIKISIWGPHR
161 DKRVGEWLGVKKWRLWDAWLNYVGFTVLKDNGDDDHTIIE
201 TNPHSAIPNQEEFDIHTSPSIFAFVPHGIFPFGLAFSCLP
241 ERGHEQTWGLFRPVVATATKLFPLVRTFISWMNGVDASDS
281 AVSRALAPPYTSDHPGRVGVSPGGIAEMFETYPKPGFHPN
321 DEAALLKDRNGLFKLAMKHKLPLVPVYCFGATKMLRRVQL
361 PAFVETLSRMLKISLCLFFGKLGLPIPFRQRLMYVMGKTL
401 FPPLPRDGVNTSMMEGGEEFDGRVQEMHDAFCNEITRIFE
441 RNKDHYGWGNKNLRLV
```

FIG 6B

```
337    M    K    H    K    L    P    L    V    P    V    Y    C    F    G
1009  atg  aaa  cac  aag  ctg  ccg  ctt  gtt  ccg  gtg  tac  tgc  ttt  gga
```

FIG 7A

```
  1  MTTKKRPKPRHKHLPPGVEVLVSPPPYEVCTLVDRLLVYA
 41  SSLIVVGSPVWFYGGIIYFYRKWKLYRSKAAATFAARHES
 81  GGGGASSTVRCRGTRQRTSSDDGNYTSSTGESSQEMNEQE
121  TQTQSHRQQTEQYNNYKRLATRYGVAKAAIIKISIWGPHR
161  DKRVGEWLGVKKWRLWDAWLNYVGFTVLKDNGDDDHTIIE
201  TNPHSAIPNQEEFDIHTSPSIFAFVPHGIFPFGLAFSCLP
241  ERGHEQTWGLFRPVVATATKLFPLVRTFISWMNGVDASDS
281  AVSRALAPPYTSDHPGRVGVSPGGIAEMFETYPKPGFHPN
321  DEAALLKDRNGLFKLAMKHKLPIVPVYCFGATKMLRRVQL
361  PAFVKTLSRMLKISLCLFFGKLGLPIPFRQRLMYVMGKTL
401  FPPLPRDGVNTSMMEGGEEFDGRVQEMHDAFCNEITRIFE
441  RNKDHYGWGNKNLRLV
```

FIG 7B

```
 365  K    T    L    S    R    M    L    K    I    S    L    C    L    F
1093  aag  acg  ttg  agc  aga  atg  ctc  aag  atc  agt  ctt  tgt  tta  ttc
```

FIG 8A

```
  1  MTTKKRPKPRHKHLPPGVEVLVSPPPYEVCTLVDRLLVYA
 41  SSLIVVGSPVWFYGGIIYFYRKWKLYRSKAAATFAARHES
 81  GGGGASSTVRCRGTRQRTSSDDGNYTSSTGESSQEMNEQE
121  TQTQSHRQQTEQYNNYKRLATRYGVAKAAIIKISIWGPHR
161  DKRVGEWLGVKKWRLWDAWLNYVGFTVLKDNGDDDHTIIE
201  TNPHSAIPNQEEFDIHTSPSIFAFVPHGIFPFGLAFSCLP
241  ERGHEQTWGLFRPVVATATKLFPLVRTFISWMNGVDASDS
281  AVSRALAPPYTSDHPGRVGVSPGGIAEMFETYPKPGFHPN
321  DEAALLKDRNGLFKLAMKHKLPIVPVYCFGATKMLRRVQL
361  PAFVETLSRMLKISLCLFFGKLGLPIPFRQRLMYVMGKTI
401  FPPLPRDGVNTSMMEGGEEFDGRVQEMHDAFCNEITRIFE
441  RNKDHYGWGNKNLRLV
```

FIG 8B

```
 393  M    Y    V    M    G    K    T    I    F    P    P    L    P    R
1177  atg  tat  gtc  atg  ggc  aag  acg  atc  ttt  cct  cct  ctg  ccg  aga
```

DIACYLGLYCEROL ACYLTRANSFERASE 2 GENES AND PROTEINS ENCODED THEREBY FROM ALGAE

PRIORITY CLAIM

This application claims the benefit of the filing date of U.S. Provisional Patent Application Ser. No. 61/008,742, filed Dec. 21, 2007, for "DIACYLGLYCEROL ACYLTRANSFERASE 2 GENES AND PROTEINS ENCODED THEREBY FROM ALGAE."

TECHNICAL FIELD

This disclosure relates generally to biotechnology and, more particularly, to genes useful for the genetic manipulation of plant characteristics. In certain embodiments, the disclosure relates to isolated and/or purified polypeptides and nucleic acids encoding diacylglycerol acyltransferase 2 (DGAT2) and methods of their use.

BACKGROUND

Oil seed crops are a significant agricultural commodity. Plant seed oils are major sources of essential polyunsaturated fatty acids for human diets and renewable feedstocks for chemical industries. The enzymes of the fatty acid synthase complex in the plastids of developing seeds are responsible for the biosynthesis of fatty acids that are channeled into the cytosolic acyl CoA pool to sustain triacylglycerol accumulation. Triacylglycerol (TAG) biosynthesis is located in the endoplasmic reticulum with glycerol 3 phosphate and fatty acyl CoAs as the primary substrates. There are three acyltransferases involved in the plant storage lipid bioassembly, namely the glycerol 3 phosphate acyltransferase (GPAT, EC 2.3.1.15), the lyso phosphatidic acid acyltransferase (LPAT, EC 2.3.1.51) and the diacylglycerol acyltransferase (DGAT, EC 2.3.1.20). These three acyltransferases catalyze the stepwise acylation of the glycerol backbone with the final step being the acylation of sn-1,2-diacylglycerol (DAG) by DGAT into the formation of TAGs, a biochemical process generally known as the Kennedy pathway. DGAT-mediated acylation of the glycerol backbone to produce TAG has been suggested as the rate limiting step in plant lipids accumulation. Thus, DGAT is a target in the genetic modification of plant lipid biosynthesis.

DISCLOSURE OF INVENTION

We disclose herein a genus of polypeptides having at least 90% sequence identity to *T. pseudonana* diacylglycerol acyltransferase 2 (DGAT). These polypeptides may be used to alter the levels of polyunsaturated fatty acids in plants. Also disclosed are polypeptides comprising the catalytic diacylglycerol transferase domain of *Thalassiosira pseudonana* DGAT2, and polypeptides having at least 90% sequence identity to the catalytic diacylglycerol transferase domain of DGAT2. Further described are polynucleotide sequences that encode polypeptides having at least 90% sequence identity to *T. pseudonana* DGAT2, and polynucleotides encoding polypeptides with at least 90% identity to the diacylglycerol transferase domain of *T. pseudonana* DGAT2.

Herein we disclose an isolated and purified diacylglycerol acyltransferase 2 (DGAT) gene and cDNA sequences from *T. pseudonana*. Also disclosed is the full length DGAT2 cDNA sequence from *T. pseudonana*, and cDNA sequences with at least 80% sequence identity to the DGAT2 cDNA. In some embodiments, these cDNA sequences may be contained within a vector. These polynucleotides may be used to modify the natural formation of triacylglycerols in plants in order to increase the yield of commercial plant oils, or to modify their composition to achieve specific commercial improvements of plants and plant products.

Also disclosed are other isolated and purified genes and cDNA sequences of the DGAT2 family from *T. pseudonana*, and from other species of algae, including *Chlamydomonas reinhardtii, Ostreococcus lucimarinus, Ostreococcus tauri*, and *Phaeodactylum tricornutum*. These polynucleotides may also be used to modify the natural formation of triacylglycerols in plants in order to increase the yield of commercial plant oils, or to modify their composition to achieve specific commercial improvements of plants and plant products.

A transgenic plant containing a nucleic acid construct is also disclosed. A method of transforming a cell or a plant is described; the method comprising introducing the isolated, purified or recombinant nucleic acid into the cell or plant. A process for producing a genetically transformed plant seed comprises introducing the nucleic acid into the plant seed. In some embodiments, these methods may be used for modifying plants to change their seed oil content.

Stated most generally, some examples disclose the isolation, purification and characterization of a DGAT2 gene from algae, and the utility of DGAT2 in the production of very long chain polyunsaturated fatty acids. The foregoing will become more apparent from the following detailed description of several embodiments, which proceeds with reference to the accompanying figures.

BRIEF DESCRIPTION OF DRAWINGS

FIG. 1 depicts the deduced amino acid sequence (SEQ ID NO:1) corresponding to the full length DGAT2 cDNA sequence of *T. pseudonana* DGAT2 (SEQ ID NO:2).

FIG. 2 depicts a sequence alignment between SEQ ID NO:1 (TpDGA2) and gi:37182187, gi:50541689, gi:74623358, gi:74623359, gi:86279638, and gi:62825813, which are all type 2 diacylglycerol acyltransferases. Amino acids common to four or more of the sequences are indicated in bold. The amino acid sequence comprising the catalytic diacylglycerol transferase domain of these type 2 diacylglycerol acyltransferases consists of residues: 236-365. (TpDGA2); 79-208 (gi:37182187); 76-205 (gi:50541689); 76-205 (gi:74623358); 34-165 (gi:74623359); 33-165 (gi:86279638); 36-165 (gi:62825813).

FIG. 3A depicts one example of a polypeptide sequence homologous to SEQ ID NO:1; (SEQ ID NO:3). FIG. 3B depicts a portion of a polynucleotide sequence with at least 90% homology to SEQ ID NO:2, and encoding a portion of the polypeptide of SEQ ID NO:3; (SEQ ID NO:4).

FIG. 4A depicts another example of a polypeptide sequence homologous to SEQ ID NO:1; (SEQ ID NO:5). FIG. 4B depicts a portion of a polynucleotide sequence with at least 90% homology to SEQ ID NO:2, and encoding a portion of the polypeptide of SEQ ID NO:5; (SEQ ID NO:6).

FIG. 5A depicts another example of a polypeptide sequence homologous to SEQ ID NO:1; (SEQ ID NO:7). FIG. 5B depicts a portion of a polynucleotide sequence with at least 90% homology to SEQ ID NO:2, and encoding a portion of the polypeptide of SEQ ID NO:7; (SEQ ID NO:8).

FIG. 6A depicts another example of a polypeptide sequence homologous to SEQ ID NO:1; (SEQ ID NO:9). FIG. 6B depicts a portion of a polynucleotide sequence with at least 90% homology to SEQ ID NO:2, and encoding a portion of the polypeptide of SEQ ID NO:9; (SEQ ID NO:10).

FIG. 7A depicts another example of a polypeptide sequence homologous to SEQ ID NO:1; (SEQ ID NO:11). FIG. 7B depicts a portion of a polynucleotide sequence with at least 90% homology to SEQ ID NO:2, and encoding a portion of the polypeptide of SEQ ID NO:11; (SEQ ID NO:12).

FIG. 8A depicts another example of a polypeptide sequence homologous to SEQ ID NO:1; (SEQ ID NO:13). FIG. 8B depicts a portion of a polynucleotide sequence with at least 90% homology to SEQ ID NO:2, and encoding a portion of the polypeptide of SEQ ID NO:13; (SEQ ID NO:14).

BEST MODES FOR CARRYING OUT THE INVENTION

I. Overview of Several Embodiments

Disclosed herein is the isolated and purified type 2 diacylglycerol acyltransferase (DGAT2) of T. pseudonana. The surprising ability of this polypeptide to modify the synthesis of very long chain polyunsaturated fatty acids (VLCPUFA) in other organisms, and cells from other organisms, is used to transform plants and plant seeds to yield transgenic plants and plant seeds with desirable fatty acid compositions. Included in this disclosure are polypeptides with DGAT2 activity having an amino acid sequence of at least 90% sequence identity to that of T. pseudonana DGAT2. In certain embodiments, these polypeptide sequences comprise, for example, SEQ ID NO:1, SEQ ID NO:3, SEQ ID NO:5, SEQ ID NO:7, SEQ ID NO:9, SEQ ID NO:11, or SEQ ID NO:13. Also disclosed are polypeptides comprising sequences with at least 90% sequence identity to the catalytic diacylglycerol acyltransferase domain of T. pseudonana DGAT2. In certain embodiments, these polypeptide sequences comprise, for example, SEQ ID NO:15, SEQ ID NO:17, or SEQ ID NO:19. The catalytic diacylglycerol acyltransferase domain of T. pseudonana DGAT2 is depicted in FIG. 2; it consists of amino acid residues 236-365 in the complete disclosed polypeptide sequence of T. pseudonana DGAT2.

Figure 10:
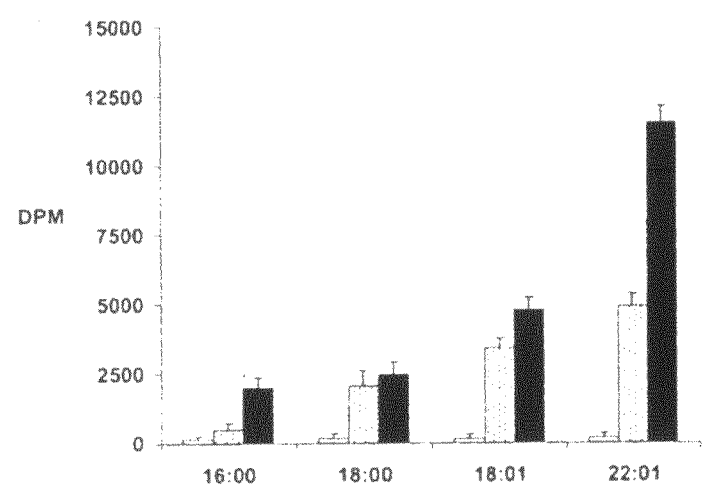
FIG. 10 shows DGAT activity in yeast mutant H1246 MAT α transformed with empty plasmid (pYES2.1 Con; empty bars), with the T. pseudonana DGAT2 cDNA (pYES:DGAT; stippled bars) and with the A. thaliana DGAT1 cDNA (solid black bars). The microsomal membrane fractions prepared from lysates of the induced yeast cells were assayed for DGAT activity using different $^{14}$C-labelled acyl-CoAs as acyl donors, and unlabeled sn-1,2 diolein as acceptor. The relative DGAT activity here was expressed as DPM (the amount of $^{14}$C-labeled substrates incorporated into TAGs). The results illustrate the substrate preference and relative activity of TpDGAT2 and AtDGAT1.
Figure 11:
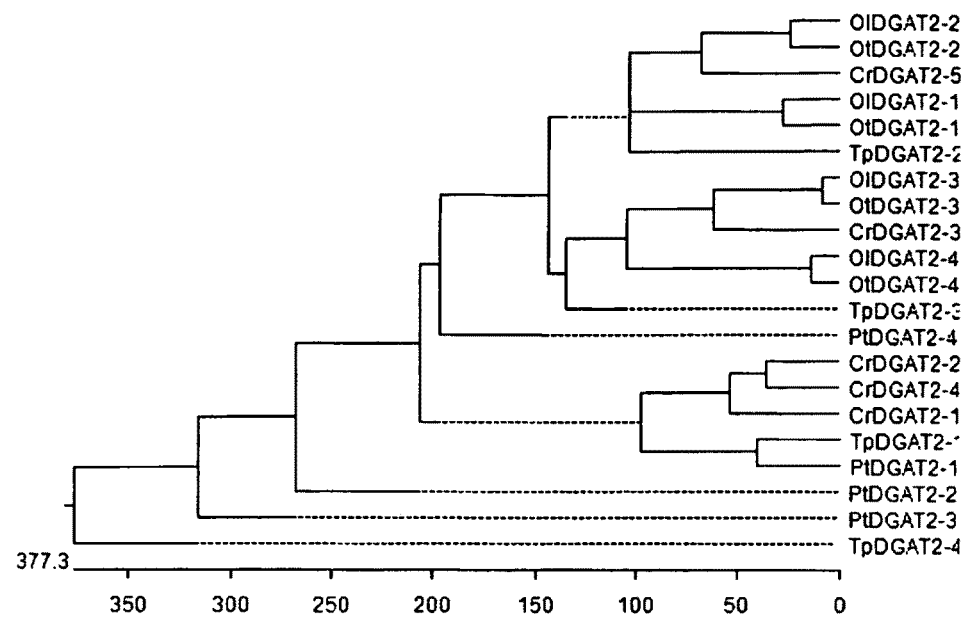
FIG. 11 depicts a homology comparison of the amino acid sequences of the TpDGAT2 (TpDGAT2-1) with its family members from T. pseudonana or from other algae species (Cr—Chlamydomonas reinhardtii; Ol—Ostreococcus lucimarinus; Ot—Ostreococcus tauri; Pt—Phaeodactylum tricornutum). TpDGAT2 (TpDGAT2-1) shares 24%, 25%, and 17% sequence identity with its family members TpDGAT2-2, TpDGAT2-3, and TpDGAT2-4, respectively. Among different algae species TpDGAT2 (TpDGAT2-1) exhibits high sequence similarity with PtDGAT2-1 (48% sequence identity), and relatively high similarity with CrDGAT2-1, CrDGAT2-2, and CrDGAT2-4 (20%, 23%, and 24% respectively).

The polypeptide of SEQ ID NO:15 comprises the diacylglycerol acyltransferase domain of T. pseudonana DGAT2. Some embodiments relate to isolated or purified polypeptides comprising sequences with at least about 90%, 91%, 92%, 93%, 94%, 95%, 96%, 97%, 98%, 99%, 99.5%, 99.6%, or 99.7% sequence identity to the isolated or purified polypeptide of SEQ ID NO:15, for example, SEQ ID NO:1. In particular embodiments, these polypeptides have diacylglycerol acyltransferase activity. Diacylglycerol acyltransferase activity can easily be determined by one skilled in the art by, for example, in vitro enzyme assay. This method is described in detail in Example 4, and typical results of this assay are shown in FIG. 10. As will be appreciated by persons skilled in the art, the disclosure also relates to substantially homologous DNA sequences from plants and algae encoding proteins comprising deduced amino acid sequences of 90% or greater identity to SEQ ID NO:15.

Other isolated or purified polypeptides from algae that are members of the DGAT2 family comprise amino acid sequences that are at least 90% identical to, for example, SEQ ID NO:25 (TpDGAT2-2), SEQ ID NO:27 (TpDGAT2-3), SEQ ID NO:29 (TpDGAT2-4), SEQ ID NO:31 (CrDGAT2-1), SEQ ID NO:33 (CrDGAT2-2), SEQ ID NO:35 (CrDGAT2-3), SEQ ID NO:37 (CrDGAT2-4), SEQ ID NO:39 (CrDGAT2-5), SEQ ID NO:41 (OlDGAT2-1), SEQ ID NO:43 (OlDGAT2-2), SEQ ID NO:45 (OlDGAT2-3), SEQ ID NO:47 (OlDGAT2-4), SEQ ID NO:49 (OtDGAT2-1), SEQ ID NO:51 (OtDGAT2-2), SEQ ID NO:53 (OtDGAT2-3), SEQ ID NO:55 (OtDGAT2-4), SEQ ID NO:57 (PtDGAT2-1), SEQ ID NO:59 (PtDGAT2-2), SEQ ID NO:61 (PtDGAT2-3), or SEQ ID NO:63 (PtDGAT2-4).

Some embodiments relate to isolated or purified nucleic acids (polynucleotides) that encode the polypeptides described above. The sequences of these polynucleotides may comprise, for example, SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:26 (TpDGAT2-2), SEQ ID NO:28 (TpDGAT2-3), SEQ ID NO:30 (TpDGAT2-4), SEQ ID NO:32 (CrDGAT2-1), SEQ ID NO:34 (CrDGAT2-2), SEQ ID NO:36 (CrDGAT2-3), SEQ ID NO:38 (CrDGAT2-4), SEQ ID NO:40 (CrDGAT2-5), SEQ ID NO:42 (OlDGAT2-1), SEQ ID NO:44 (OlDGAT2-2), SEQ ID NO:46 (OlDGAT2-3), SEQ ID NO:48 (OlDGAT2-4), SEQ ID NO:50 (OtDGAT2-1), SEQ ID NO:52 (OtDGAT2-2), SEQ ID NO:54 (OtDGAT2-3), SEQ ID NO:56 (OtDGAT2-4), SEQ ID NO:58 (PtDGAT2-1), SEQ ID NO:60 (PtDGAT2-2), SEQ ID NO:62 (PtDGAT2-3), or SEQ ID NO:64 (PtDGAT2-4). In some embodiments, the polynucleotide sequences have a percentage identity with the bases of a disclosed nucleotide sequence of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7% that encode a disclosed polypeptide. Several examples of such polynucleotides are SEQ ID NOS:21-24. As will be appreciated by the skilled practitioner, slight changes in nucleic acid sequence do not necessarily alter the amino acid sequence of the encoded polypeptide. It will be appreciated by persons skilled in the art that changes in the identities of nucleotides in a specific gene sequence that change the amino acid sequence of the encoded polypeptide may result in reduced or enhanced effectiveness of the genes and that, in some applications (i.e., antisense, co-suppression, or RNAi), partial sequences often work as effectively as full length versions. The ways in which the gene sequence can be varied or shortened are well known to persons skilled in the art, as are ways of testing the effectiveness of the altered genes. In certain embodiments, effectiveness may easily be tested by, for example, conventional gas chromatography. All such variations of the genes are therefore included as part hereof.

Some embodiments relate to a vector containing an isolated or purified polynucleotide having at least 80% homology to SEQ ID NO:2; for example, SEQ ID NO:2, SEQ ID NO:15, SEQ ID NO:16, SEQ ID NO:17, SEQ ID NO:18, SEQ ID NO:20, SEQ ID NO:21-24. Accordingly, there is provided a method for preparing a vector including a sequence selected from a group consisting of, for example SEQ ID NO:2; for example, SEQ ID NO:2, SEQ ID NO:15, SEQ ID NO:16, SEQ ID NO:17, SEQ ID NO:18, SEQ ID NO:20, or SEQ ID NO:21-24, or a part thereof, for introduction of the sequence or partial sequence in an antisense orientation, or the complement thereof, into a plant cell.

Certain embodiments relate to a vector containing polynucleotide having at least 80% homology to members of the DGAT2 family in algae. These vectors may comprise polynucleotide sequences of, for example, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, SEQ ED NO:60, SEQ ID NO:62, or SEQ ID NO:64.

In some embodiments, the isolated and purified polynucleotides, and vectors comprising these isolated and purified polynucleotides, may be used to create transgenic plants that produce polypeptides with DGAT2 activity. Therefore, one embodiment relates to transgenic plants and plant seeds including an isolated or purified polynucleotide having at least 80% homology to SEQ ID NO:2; for example, a deoxyribonucleic acid molecule with the sequence of SEQ ID NO:2, SEQ ID NO:15, SEQ ID NO:16, SEQ ID NO:17, SEQ ID NO:18, SEQ ID NO:20, or SEQ ID NO:21-24. Other embodiments relate to transgenic plants and plant seeds including an isolated or purified polynucleotide having at least 80% homology to another member of the DGAT2 family in algae; for example a deoxyribonucleic acid molecule with the sequence of SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48; SEQ ID NO:50, SEQ ID NO:52, SEQ ID NO:54, SEQ ID NO:56, SEQ ID NO:58, SEQ ID NO:60, SEQ ID NO:62, or SEQ ID NO:64. Plants of these embodiments may have altered levels of polyunsaturated fatty acids in seeds as compared to levels in a plant lacking the nucleic acid construct. The fatty acids in the plant may be more than about 70% polyunsaturated fatty acids.

One embodiment comprises a method of producing such plants and plant seeds. The method comprises creating a nucleic acid construct comprising a polynucleotide encoding a polypeptide having at least 90% sequence identity to a polypeptide selected from the group consisting of SEQ ID NOS: 1, 3, 5, 7, 9, 11, 13, 15, 17, and 19, or a polypeptide having at least 90% sequence identity to a polypeptide of the DGAT2 family in algae; for example, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, or SEQ ID NO:63; and introducing the construct into a plant. The method of this embodiment may be accomplished by any means known to one of ordinary skill in the art, by way of non-limiting example, *Agrobacterium*-mediated transformation. In specific embodiments, the method further comprises introducing a polynucleotide encoding a polypeptide with *Brassica* pyruvate dehydrogenase kinase activity, a polynucleotide encoding a polypeptide with diacylglycerol acetyltransferase activity, and/or a polynucleotide encoding a polypeptide with glycerol-3-phosphate dehydrogenase activity into the plant. This method may be practiced wherein the plant is selected from the group consisting of *Arabidopsis thaliana*, *Borago* spp., Canola. *Ricinus* spp., *Theobroma* spp., *Zea* spp., *Gossypium* spp, *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Carthamus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae.

In some embodiments, the method further comprises harvesting a seed from the plant including the introduced nucleic acid construct, and extracting oil from the harvested seed. Therefore, other embodiments include a plant produced by the method, and oil extracted from the plant produced by the method.

Some of the manipulations and deliverables which are possible using the DGAT2 gene or a part thereof, include, but are not limited to, the following: seeds with increased or decreased oil content; seeds containing oils with an enhanced very long chain polyunsaturated fatty acid content, and plants exhibiting an enhanced or altered capacity to accumulate very long chain polyunsaturated fatty acids.

II. Abbreviations

| | |
|---|---|
| CaMV | cauliflower mosaic virus |
| cDNA | complementary DNA |
| CERV | carnation etched ring virus |
| CrDGAT2 | *Chlamydomonas reinhardtii* type 2 diacylglycerol transferase |
| DAG | sn-1,2-diacylglycerol |
| DGAT | diacylglycerol acyltransferase |
| DGAT2 | type 2 diacylglycerol transferase |
| DHA | docosahexaenoic acid |
| DNA | deoxyribonucleic acid |
| EPA | eicosapentaenoic acid |
| GPAT | glycerol 3 phosphate acyltransferase |
| LPAT | lyso phosphatidic acid acyltransferase |
| OlDGAT2 | *Ostreococcus lucimarinus* type 2 diacylglycerol transferase |
| OtDGAT2 | *Ostreococcus tauri* type 2 diacylglycerol transferase |
| PCR | polymerase chain reaction |
| PtDGAT2 | *Phaeodactylum tricornutum* type 2 diacylglycerol transferase |
| RNA | ribonucleic acid |
| RNAi | RNA interference |
| RT-PCR | reverse transcription PCR |
| T35S | CaMV 35S terminator |
| TAG | triacylglycerol |
| TLC | thin layer chromatography |
| Tmas | mannopine synthase terminator |

| | |
|---|---|
| Tnos | nopaline synthase terminator |
| TpDGAT2 | *T. pseudonana* type 2 diacylglycerol transferase |
| TrbcS | ribulose bisphosphate carboxylase small subunit termination region |
| VLCPUFA | very long chain polyunsaturated fatty acids |

III. Terms

In order to facilitate review of the various embodiments of the disclosure, the following explanations of specific terms are provided:

Complementary nucleotide sequence: "Complementary nucleotide sequence" of a sequence is understood as meaning any DNA whose nucleotides are complementary to those of sequence of the disclosure, and whose orientation is reversed (antiparallel sequence).

Degree or percentage of sequence homology: The term "degree or percentage of sequence homology" refers to degree or percentage of sequence identity between two sequences: after optimal alignment. Percentage of sequence identity (or degree or identity) is determined by comparing two optimally aligned sequences over a comparison window, where the portion of the peptide or polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity.

Homologous isolated and/or purified sequence: "Homologous isolated and/or purified sequence" is understood to mean an isolated and/or purified sequence having a percentage identity with the bases of a nucleotide sequence, or the amino acids of a polypeptide sequence, of at least about 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%. This percentage is purely statistical, and it is possible to distribute the differences between the two nucleotide sequences at random and over the whole of their length. Sequence identity can be determined, for example, by computer programs designed to perform single and multiple sequence alignments. It will be appreciated that this disclosure embraces the degeneracy of codon usage as would be understood by one of ordinary skill in the art. Furthermore, it will be understood by one skilled in the art that conservative substitutions may be made in the amino acid sequence of a polypeptide without disrupting the structure or function of the polypeptide. Conservative substitutions are accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins.

Isolated: As will be appreciated by one of skill in the art, "isolated" refers to polypeptides that have been "isolated" from their native environment.

Nucleotide, polynucleotide, or nucleic acid sequence: "Nucleotide, polynucleotide, or nucleic acid sequence" will be understood as meaning both a double-stranded or single-stranded DNA in the monomeric and dimeric (so-called in tandem) forms and the transcription products of said DNAs.

Sequence identity: Two amino-acids or nucleotide sequences are said to be "dentical" if the sequence of amino-acids or nucleotidic residues in the two sequences is the same when aligned for maximum correspondence as described below. Sequence comparisons between two (or more) peptides or polynucleotides are typically performed by comparing sequences of two optimally aligned sequences over a segment or "comparison window" to identify and compare local regions of sequence similarity. Optimal alignment of sequences for comparison may be conducted by the local homology algorithm of Smith and Waterman, Ad. App. Math 2: 482 (1981), by the homology alignment algorithm of Neddleman and Wunsch, J. Mol. Biol. 48: 443 (1970), by the search for similarity method of Pearson and Lipman, Proc. Natl. Acad. Sci. (U.S.A.) 85: 2444 (1988), by computerized implementation of these algorithms (GAP, BESTFIT, FASTA, and TFASTA in the Wisconsin Genetics Software Package, Genetics Computer Group (GCG), 575 Science Dr., Madison, Wis.), or by visual inspection.

The definition of sequence identity given above is the definition that would be used by one of skill in the art. The definition by itself does not need the help of any algorithm, said algorithms being helpful only to achieve the optimal alignments of sequences, rather than the calculation of sequence identity.

From the definition given above, it follows that there is a well defined and only one value for the sequence identity between two compared sequences which value corresponds to the value obtained for the best or optimal alignment.

In the BLAST N or BLAST P "BLAST 2 sequence," software which is available in the web site blast(DOT)ncbi(DOT)nlm(DOT)nih(DOT)gov/Blast(DOT)cgi, and habitually used by the inventors and in general by the skilled man for comparing and determining the identity between two sequences, gap cost which depends on the sequence length to be compared is directly selected by the software (i.e. 11.2 for substitution matrix BLOSUM-62 for length>85).

Stringent hybridization: Hybridization under conditions of stringency with a nucleotide sequence is understood as meaning a hybridization under conditions of temperature and ionic strength chosen in such a way that they allow the maintenance of the hybridization between two fragments of complementary DNA. Homologs of the DGAT2 genes described herein obtained from other organisms, for example plants, may be obtained by screening appropriate libraries that include the homologs, wherein the screening is performed with the nucleotide sequence of the specific DGAT2 genes disclosed herein, or portions or probes thereof, or identified by sequence homology search using sequence alignment search programs such as BLAST, FASTA.

III. Modification of Fatty Acid Levels by DGAT2 from Algae

A. Overview

Recent studies on DGAT2 from tung tree and castor bean suggest that in plants containing unusual fatty acids, DGAT2 may play an important role in channeling unusual fatty acids into seed storage oils. While DGAT2 may be a potential target in the genetic modification of plant lipid biosynthesis in oilseeds, the recently characterized enzymes contributed to the utilization of conjugated fatty acid eleostearic acid (tung tree DGAT2) and ricinolenic acid (castor bean DGAT2) respectively. Neither enzyme (tung tree DGAT2 or castor bean DGAT2) is involved in the incorporation of commercially desirable long chain omega-3 polyunsaturated fatty acids eicosapentaenoic acid (EPA) and docosahexaenoic acid (DHA) in triacylglycerol (TAG).

The marine centric diatom algae *T. pseudonana* is able to produce and accumulate long chain omega-3 polyunsaturated fatty acids EPA and DHA in TAG and is a good source of high level very long chain polyunsaturated fatty acid (VLCPUFA) accumulated oils. For this reason, the *T. pseudonana* diacylglycerol acyltransferase 2 (TpDGAT2) gene was investigated and characterized. Surprisingly, it was discovered that TpDGAT2, unlike DGAT2 from tung tree or castor bean, can efficiently incorporate very long chain polyunsaturated fatty acids into TAG. Using the TpDGAT2 gene to search polynucleotide sequences from *T. pseudonana* and related species of algae, other members of the DGAT2 family in algae were identified. Thus, algal DGAT2 genes were determined to be useful in transgenic tools and for the modification of TAG composition and accumulation in seeds.

B. Polypeptides Homologous to *T. pseudonana* DGAT2 with Type 2 Diacylglycerol Transferase Activity Proteins that are homologous to full-length *T. pseudonana* DGAT2 can be found by searching protein databases, such as the NCBI protein database, with search engines, such as BLAST. They may also be identified by rational design. The process of rational design may comprise identifying conservative amino acid substitutions within the desired polypeptide sequence length, and making those substitutions in the encoded protein.

Searching the NCBI protein database with the full-length amino acid sequence of *T. pseudonana* DGAT2 (BLASTP) reveals polypeptides with significant sequence homology to TpDGAT2, several of which are shown aligned with TpDGAT2 in FIG. 2. The conserved type 2 diacylglycerol transferase domain is aligned in FIG. 2, and consists of amino acid residues 236-365 in TpDGAT2 and the corresponding residues from the other DGAT2 polypeptides depicted. The conserved type 2 diacylglycerol transferase domain is described within NCBI's conserved domain database ncbi(DOT)nlm (DOT)nih(DOT)gov/Structure/cdd/wrpsb(DOT)cgi. Polypeptide sequences that are homologous to this conserved domain impart the type 2 diacylglycerol activity of TpDGAT2 to proteins wherein it is contained.

It is understood by those of ordinary skill in the art that polypeptides with homologous sequences may be designed to exhibit the same structure and function as their homologs. The skilled artisan is enabled to design homologous polypeptides to those specifically described in the examples of this disclosure by the sequence alignment of FIG. 2. Such homologous polypeptides may be those that contain conservative substitutions to polypeptides of the present disclosure, for example the polypeptides of SEQ ID NO:3, SEQ ID NO:5, SEQ ID NO:7, SEQ ID NO:9, SEQ ID NO:11, SEQ ID NO:13, SEQ ID NO:15, SEQ ID NO:17, or SEQ ID NO:19. Simple experimental assays that determine which homologous proteins exhibit substantially similar type 2 diacylglycerol transferase activity to TpDGAT2 are known to those skilled in the art. Such assays are not unduly time-consuming, expensive, or technically difficult. For example, conventional gas chromatography may be used to detect TAG produced by TpDGAT2. Several of these assays are described in the detailed examples below.

C. Use of Nucleic Acid Molecules to Transform with DGAT2 Activity

It must be understood that disclosed embodiments do not include the genomic nucleotide sequences taken in their natural environment; that is to say, in the natural genome of *T. pseudonana*, *Chlamydomonas reinhardtii*, *Ostreococcus lucimarinus*, *Ostreococcus tauri*, or *Phaeodactylum tricornutum*. Some embodiments concern sequences which it has been possible to isolate, purify or partially purify, starting from separation methods such as, for example, ion-exchange chromatography, by exclusion based on molecular size, or by affinity, or alternatively fractionation techniques based on solubility in different solvents, or starting from methods of genetic engineering such as amplification, cloning, and subcloning, it being possible for the sequences to be carried by vectors.

Further included are nucleic acid molecules that hybridize to the above disclosed sequences. Hybridization conditions may be stringent in that hybridization will occur if there is at least a 90%, 95% or 97% identity with the nucleic acid molecule that encodes the disclosed DGAT2 molecules. The stringent conditions may include those used for known Southern hybridizations such as, for example, incubation overnight at 420 C in a solution having: 50% formamide, 5×SSC (150 mM NaCl, 15 mM trisodium citrate), 50 mM sodium phosphate (pH 7.6), 5×Denhardt's solution, 10% dextran sulfate, and 20 micrograms/milliliter denatured, sheared salmon sperm DNA, following by washing the hybridization support in 0.1×SSC at about 65° C. Other known hybridization conditions are well known and are described in Sambrook, et al., Molecular Cloning: A Laboratory Manual, Third Edition, Cold Spring Harbor, N.Y. (2001).

DNA isolation and cloning is well established. Similarly, DNA encoding an isolated enzyme may be inserted into a vector and transformed into yeast cells by conventional techniques. However, because no DGAT2 gene that can efficiently use VLCPUFA has been cloned, it has not been possible to address the possibility of genetic modifications by modulating DGAT2 activity. We confirmed that DGAT2 is involved with TAG synthesis and utilizes VLCPUFA more efficiently than DGAT.

Nucleic acid molecules that code for DGAT2, for example sequences having at least 80% identity to SEQ ID NO:2, SEQ ID NO:16, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, or SEQ ID NO:61, may be transformed into an organism, for example a plant. Such homologous sequences are exemplified by SEQ ID NOS:21-24. As known in the art, there are a number of ways by which genes and gene constructs can be introduced into organisms, for example plants, and a combination of transformation and tissue culture techniques have been successfully integrated into effective strategies for creating transgenic organisms, for example crop plants. These methods have been described elsewhere (Potrykus, 1991; Vasil, 1994; Walden and Wingender, 1995; Songstad, et al., 1995), and are well known to persons skilled in the art. For example, one skilled in the art will certainly be aware that, in addition to *Agrobacterium*-mediated transformation of *Arabidopsis* by vacuum infiltration (Bechtold et al., 1993) or wound inoculation (Katavic, et al., 1994), it is equally possible to transform other plant and crop species, using *Agrobacterium* Ti-plasmid mediated transformation (e.g., hypocotyl (DeBlock, et al., 1989) or cotyledonary petiole (Moloney, et al., 1989) wound infection), particle bombardment/biolistic methods (Sanford, et al., 1987; Nehra, et al., 1994; Becker, et al., 1994) or polyethylene glycol-assisted, protoplast transformation (Rhodes, et al., 1988; Shimamoto, et al., 1989) methods.

There are many examples of successful modifications to plant metabolism that have been achieved by genetic engineering to transfer new genes or to alter the expression of existing genes, in plants. It is now routinely possible to introduce genes into many plant species of agronomic significance to improve crop performance (e.g. seed oil or tuber starch content/composition; meal improvement; herbicide, disease or insect resistance; heavy metal tolerance etc.) (MacKenzie and Jain, 1997; Budziszewski, et al., 1996; Somerville, 1993; Kishore and Somerville, 1993).

As will also be apparent to persons skilled in the art, and as described elsewhere (Meyer, 1995; Dada, et al., 1997), it is possible to utilize plant, promoters to direct any intended up- or down-regulation of transgene expression using constitutive promoters (e.g., those based on CaMV35S), or by using promoters which can target gene expression to particular cells, tissues (e.g., napin promoter for expression of transgenes in developing seed cotyledons), organs (e.g., roots), to a particular developmental stage, or in response to a particular external stimulus (e.g., heat shock).

Promoters for use herein may be inducible, constitutive, or tissue-specific or have various combinations of such characteristics. Useful promoters include, but are not limited to, constitutive promoters, e.g., carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter).

It may be desirable to use a tissue-specific or developmentally regulated promoter instead of a constitutive promoter in certain circumstances. A tissue-specific promoter allows for overexpression in certain tissues without affecting expression in other tissues. By way of illustration, a promoter used in overexpression of enzymes in seed tissue is an ACP promoter as described in PCT International Publication WO 92/18634, published Oct. 29, 1992.

The promoter and termination regulatory regions may be functional in the host plant cell and may be heterologous (that is, not naturally occurring) or homologous (derived from the plant host species) to the plant cell and the gene. Suitable promoters which may be used are described above.

The termination regulatory region may be derived from the 3' region of the gene from which the promoter was obtained or from another gene. Suitable termination regions which may be used are well known in the art and include *Agrobacterium tumefaciens* nopaline synthase terminator (Tnos), *A. tumefaciens* mannopine synthase terminator (Tmas) and the CaMV 35S terminator (T35S), the pea ribulose bisphosphate carboxylase small subunit termination region (TrbcS), or the Tnos termination region. Such gene constructs may suitably be screened for activity by transformation into a host plant via *Agrobacterium* and screening for increased isoprenoid levels.

Suitably, the nucleotide sequences for the genes may be extracted from the GenBank® (a registered trademark of the U.S. Department of Health and Human Services) nucleotide database and searched for restriction enzymes that do not cut. These restriction sites may be added to the genes by conventional methods such as incorporating these sites in PCR primers or by sub-cloning.

Preferably, a DNA construct for use herein is comprised within a vector, most suitably an expression vector adapted for expression in an appropriate host (plant) cell. It will be appreciated that any vector which is capable of producing a plant comprising the introduced DNA sequence will be sufficient.

Suitable vectors are well known to those skilled in the art and are described in general technical references such as Pouwels, et al., Cloning Vectors. A Laboratory Manual, Elsevier, Amsterdam (1986). Particularly suitable vectors include the Ti plasmid vectors.

Transformation techniques for introducing the DNA constructs into host cells are well known in the art and include such methods as micro-injection, using polyethylene glycol, electroporation, high velocity ballistic penetration, or *Agrobacterium*-mediated transformation. After transformation of the plant cells or plant, those plant cells or plants into which the desired DNA has been incorporated may be selected by such methods as antibiotic resistance, herbicide resistance, tolerance to amino-acid analogues, or using phenotypic markers.

Various assays may be used to determine whether the plant cell shows an increase in gene expression, for example, Northern blotting or quantitative reverse transcriptase PCR (RT-PCR). Whole transgenic plants may be regenerated from the transformed cell by conventional methods. Such transgenic plants having improved isoprenoid levels may be propagated and self-pollinated to produce homozygous lines. Such plants produce seeds containing the genes for the introduced trait and can be grown to produce plants that will produce the selected phenotype.

Particularly preferred plants for modification according to the present disclosure include *Arabidopsis thaliana*, borage (*Borago* spp.), Canola, castor (*Ricinus communis*)(*Ricinus* spp.), cocoa bean (*Theobroma cacao*) (*Theobroma* spp.), corn (*Zea mays*) (*Zea* spp.), cotton (*Gossypium* spp), *Crambe* spp., *Cuphea* spp., flax (*Linum* spp.), *Lesquerella* spp. and *Limnanthes* spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (*Glycine* spp. and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the plant family Gramineae.

Some embodiments are used to modify the yield or composition of oilseed produced from oilseed crops. Oilseed crops are plant species that are capable of generating edible or industrially useful oils in commercially significant yields, and include many of the plant species listed above. Such oilseed crops are well known to persons skilled in the art.

In one example, plants transformed with a nucleotide sequence that codes for a DGAT2 are grown. Seeds of the transgenic plants are harvested and fatty acids of the seeds are extracted. The extracted fatty acids are used for subsequent incorporation into a composition, for example a pharmaceutical composition, a nutraceutical composition or a food composition.

In certain embodiments, other methods of enhancing or altering oil production may also be used with the plant to be transformed (e.g., incorporating, for expression in the plant, a nucleic acid sequence selected from the group comprising a nucleic acid sequence encoding a peptide having, for example, *Brassica* pyruvate dehydrogenase kinase activity (see, e.g., U.S. Pat. No. 7,214,859 to Marilla, et al. (May 8, 2007), U.S. Pat. No. 6,500,670 to Zou, et al. (December 2002), and U.S. Pat. No. 6,256,636 to Randall, et al. (July 2001), a nucleic acid sequence encoding a peptide having diacylglycerol acyltransferase activity (see, e.g., U.S. Pat. No. 7,015,373 and U.S. Pat. No. 6,500,670 to Zou, et al. (December 2002), and a nucleic acid sequence encoding a peptide having glycerol-3-phosphate dehydrogenase activity (see, e.g., U.S. Pat. No. 7,112,724 and combinations thereof).

Embodiments are susceptible to various modifications and alternative forms in addition to those specific examples described in detail herein. Thus, embodiments are not limited to the particular forms disclosed. Rather, the scope of the disclosure encompasses all modifications, equivalents, and alternatives falling within the following appended claims.

EXAMPLES

Example 1

DNA Manipulation

Standard methods and procedures were used for DNA preparation, plasmid propagation and isolation (Sambrook, et al., 1989). Sequencing was conducted on an Applied Biosystems Model 373A DNA Sequencing System using the Taq DyeDeoxy™ Terminator Cycle Sequencing Kit (Applied Biosystems, Inc.). The nucleotide and the deduced amino acid sequences were compared with sequences available in databanks using the BLAST program (Altschul et al., 1990). The DGAT2 clones were identified on the basis of homology with other fatty acid diacylglycerol acyltransferase genes in the NCBI nucleotide and protein databases as known in the art.

Example 2

In vivo Triacylglycerol (TAG) Formed in Yeast Transformants by Expressing TpDGAT2

The DGAT2 gene was inserted into the pYES2.1 (Invitrogen). The construct was confirmed by sequencing and pYES2.1/TpDGAT2 was used to transform *Saccharomyces cerevisiae* strain H1246 MAT-α. This mutant strain is a quadruple mutant (DGAT−, PDAT−, ASAT−, ASAT2−). Plasmid DNA was isolated from putative transformants and the presence of the pYES2.1/TpDGAT2 was confirmed by Southern analysis. H1246 MAT-α transformants containing vector only (pYES2.1) were used as controls. H1246 MAT-α transformed with *Arabidopsis thaliana* DGAT1 served as a positive control.

Single colonies were cultured overnight in 20 mL of SD medium (Synthetic Dextrose medium with glucose and without uracil, as described by Ausubel, et al., 1995, Vol. 2, p. 13.1.3) on a rotary shaker (270 rpm) at 28° C. Cells were pelleted from the overnight culture and resuspended in 50 mL of medium for induction of expression (SD medium containing galactose and without uracil). Cells were reincubated at 28° C., with shaking at 270 rpm, and harvested after four to six hours. GAL induced yeast transformants were harvested by centrifugation at 5000 rpm for 5 min. and resuspended in 100 mM Hepes NaOH, pH 7.4, containing 1 mM EDTA and 1 mM DTT.

Figure 9:
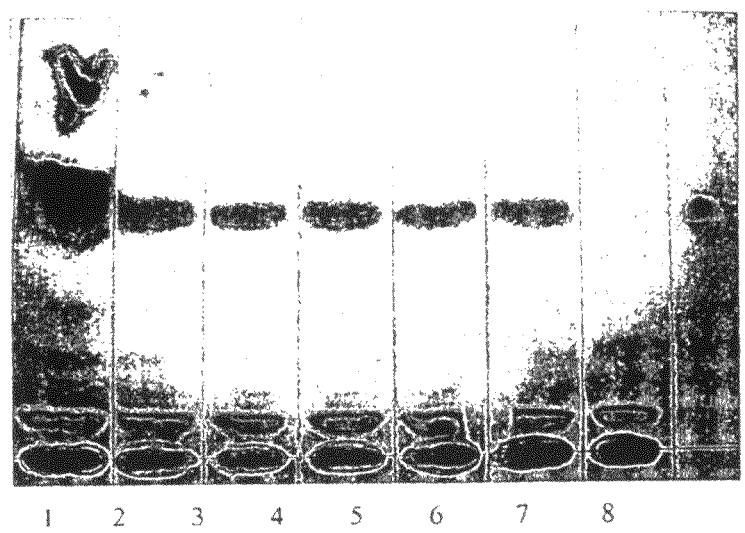
FIG. 9 depicts thin layer chromatography (TLC) analysis of TAG produced by expressing TpDGAT2 and AtDGAT1 in yeast mutant H1246 MAT α (DGAT⁻, PDAT⁻, ASAT1⁻, ASAT2⁻, which is deficient in TAG formation). Lane 1 represents the expression of AtDGAT1, Lanes 2-6 represent the expression of TpDGAT2. Clear TAG (triacylglycerol) bands were observed in lanes 2-6. Lane 8 represents an empty vector (pYES2.1) control, and there is no TAG (triacylglycerol) band in this lane. The lane on the right of lane 8 was loaded with a TAG marker which can be used as a TAG marker.

Referring to FIG. 9, no TAG was produced in the empty vector, negative control (lane 8) while the positive control (lane 1) showed a TAG band. Each of the DGAT2 containing vectors (lanes 2-6) showed a TAG band which confirmed that DGAT2 has the capacity to synthesize TAG. The lane on the right of lane 8 was loaded with a TAG standard which was used as a TAG marker.

Example 3

Substrate Preference of TpDGAT2

Cell lysates were prepared using acid washed glass beads as described by Ausubel, et al. (1995). Protein in yeast lysates was measured using the Bradford (1976) assay, protein levels in each lysate were normalized and aliquots (250 µg protein) were assayed for DGAT2 activity.

DGAT assays were conducted at pH 7.4, with shaking at 100 rev/min in a water bath at 30° C. for 10 min. Assay mixtures (0.5 ml final volume) contained 100 µg lysate protein, 90 mM HEPES-NaOH, 200 µM sn-1,2 diolein, and 18 µM $^{14}$C Acyl-CoAs (specific activity 2 nCi/nmol) as the acyl donor. The $^{14}$C-labelled TAGs were isolated by TLC on silica gel G plates developed in hexane:diethyl ether:acetic acid (70:30:1 v/v/v/), the radiolabelled TAG bands visualized on a Bioscan AR-2000 radio-TLC scanner using Win-Scan 2D® software (Bioscan Inc., Washington D.C., USA) and the bands scraped and quantified as described by Taylor et al. (1991).

Example 4

Fatty Acid Composition of TpDGAT2 Transformants

*S. cerevisiae* strain H1246 MAT-α was transformed with *A. thaliana*/pYES2.1 or *T. pseudonana*/pYES2.1. Transformants were grown for 3 days at 28° C. and induced by galactose. The transformants were treated with either nothing (control), 50 uM DHA or 150 uM DHA. The fatty acid profile of three transformants containing AtDGAT1/pYES2.1 and three transformants containing TpDGAT2/pYES2.1 are shown in Table 1 based on conventional gas chromatography analysis.

Fatty acids are identified as 16:0, 16:1, 18:0, 18:1 (oleic acid), and 22:6 (DHA); and the composition of each is presented as a percentage of the total fatty acids. Expression of DHA increased from zero in the control strain to 6.01% in the 150 µM TpDGAT2/pYES2.1 and was more than double that of 150 µM AtDGAT/pYES2.1. (Table 1) These results further confirm that TpDGAT2 utilizes DHA fatty acids more efficiently than DGAT1.

In terms of fatty acid composition, the mutant lines containing DGAT2 cDNA showed a decrease in the total saturates, and increases in the unsaturates as shown in Table 1. Such changes are all towards a "healthier" oil profile and can be applied directly to canola, other oilseeds in the Brassicaceae and other edible oil crops to produce similar oil composition improvements.

TABLE 1

Fatty Acid Composition of TAG Expressed by DGAT2 and DGAT1 in Yeast Mutant H1246 MAT-α.

| Treatment | % 16:0 | % 16:1 | % 18:0 | % 18:1 | % 22:6 | Fatty acid composition % Sats | % Unsats |
|---|---|---|---|---|---|---|---|
| AtDGAT/pYES2.1 - no feeding | 13.93 | 35.71 | 17.84 | 32.51 | 0.00 | 31.78 | 68.22 |
| AtDGAT/pYES2.1 - 50 µM DHA | 19.68 | 27.54 | 16.51 | 34.82 | 1.46 | 36.18 | 62.36 |
| AtDGAT/pYES2.1 - 150 µM DHA | 19.24 | 27.83 | 15.21 | 35.08 | 2.63 | 34.45 | 62.91 |
| TpDGAT2/pYES2.1 - no feeding | 10.03 | 30.23 | 13.83 | 45.90 | 0.00 | 23.87 | 76.13 |

TABLE 1-continued

Fatty Acid Composition of TAG Expressed by DGAT2 and DGAT1 in Yeast Mutant H1246 MAT-α.

| Treatment | % 16:0 | % 16:1 | % 18:0 | % 18:1 | % 22:6 | Fatty acid composition % Sats | % Unsats |
|---|---|---|---|---|---|---|---|
| TpDGAT2/pYES2.1 - 50 µM DHA | 6.43 | 35.39 | 8.49 | 45.07 | 4.62 | 14.92 | 80.47 |
| TpDGAT2/pYES2.1 - 150 µM DHA | 5.77 | 31.73 | 11.57 | 44.93 | 6.01 | 17.34 | 76.66 |

Example 5

Over Expression of the DGAT2 cDNA in Wild Type A. thaliana

The full length DGAT2 cDNA is used as a template for PCR amplification. A fragment is excised by restriction endonuclease digestion and ligated into the corresponding sites of a vector. The construct integrity is confirmed by sequencing.

The vector is introduced into A. tumefaciens, used to transform wild type A. thaliana, and is progeny analyzed.

Example 6

Construction of DGAT2 cDNA Plant Transformation Vector for Seed Specific Expression The full length DGAT2 cDNA is used as a template for PCR amplification with primers to provide new restriction sites on each end of the sequence. The PCR profile is as follows: 94° C. 1 minute; 30 cycles of 94° C. 30 seconds, 55° C. 30 seconds, 72° C. 1 minute; and 72° C. 5 minutes. The PCR product is then ligated into the PCR 2.1 vector (Invitrogen). A fragment is excised and ligated into the corresponding sites of a vector. The construct integrity is confirmed by sequencing.

Example 7

Transformation of Agrobacterium with Plant DGAT2 Vector Constructs

Electrocompetent Agrobacterium cells, GV3101 (pMP90) strain, are prepared as follows: An Agrobacterium culture is grown 24 to 48 hours in 2YT, and when the absorbance at 600 nm is reached 0.5 to 0.7, the cells are chilled on ice and pelleted by centrifugation (5,000×g, 10 minutes in a GSA rotor at 4° C.). The pellet is washed in 1, 0.5, and 0.02 volumes of cold 10% sterile glycerol and resuspended in 0.01 volume of cold 10% glycerol. The electrocompetent cells are then frozen in liquid $N_2$ and stored at −70° C. The Agrobacterium cells are transformed by electroporation with 20-50 ng of transforming DNA according to the manufacturer's instructions, plated on a selective medium (LB with 50 µg/mL kanamycin) and incubated overnight at 28° C. Single transformed cells are grown overnight (28° C., 225 r.p.m.) in 5 mL LB with 50 µg/mL Kanamycin and 25 µg/mL Gentamycin. DNA extraction and purification are performed. The fidelity of the construct is re checked by DNA sequencing before plant transformation.

Example 8

Transformation of Arabidopsis thaliana

Seeds of A. thaliana are grown at 22° C. under fluorescent illumination (120 µE·m$^{-2}$S$^{-1}$) in a 16 hour light/8 hour dark regime. Four to six plants are raised in a 10 cm$^2$ pot in moistened TERRA-LITE REDI-EARTH (W. R. Grace & Co. Canada Ltd. Ajax, ON, Canada). To prevent the soil mix in the pot from falling into the inoculation media, soil is mounded as a platform with seeds sown on top, and the whole pot covered by a nylon window screen and secured by a rubber band. Plants are vacuum infiltrated in an Agrobacterium suspension when the first flowers started opening.

To grow Agrobacterium, a 5 mL suspension in LB medium containing 50 µg/mL kanamycin and 25 µg/mL gentamycin is cultured overnight at 28° C. The day before infiltration, this "seed culture" is divided into four flasks containing 250 mL of LB medium supplemented with 50 µg/mL kanamycin and 25 µg/mL gentamycin. These cultures are grown overnight at 28° C. The next morning after the absorbance at 600 nm is checked (approximately =1.0), the cells are harvested by centrifugation (5,000×g, 10 minutes in a GSA rotor at room temperature) and resuspended in the infiltration medium (sucrose 5%; Silwet-77 0.005% in water) to obtain an optical density at 600 nm of 0.8.

The Agrobacterium suspension is poured into a beaker and the potted plants inverted into the beaker so that the flowers and bolts are submerged. The beaker is placed into a large Bell jar and a vacuum is drawn using a vacuum pump, until bubbles form on the stem surfaces and the solution starts to bubble slightly, and then the vacuum is released rapidly. The necessary time and pressure will vary from one lab setup to the next, but good infiltration is visibly apparent as uniformly darkened, water soaked tissue. Pots are removed from the beaker, laid on their side in a plastic tray and covered with a plastic dome, to maintain humidity. The following day, the plants are uncovered, set upright and allowed to grow for approximately four weeks in a growth chamber under continuous light conditions as described by Katavic, et al. (1995). When the siliques are mature and dry, seeds are harvested and are selected for positive transformants.

Example 9

Transformation of Brassica napus

Transformation is essentially carried out as described by Moloney, et al., 1989, Plant Cell Reports 8:238-242.

A. tumifaciens strain GV3101/pMP90 (Koncz C. & Schell, J., 1986, Mol. Gen. Genet. 204:383-396) is used for transformation studies. A stationary phase bacterial culture in LB broth (Difco, USA) (100 ml) is harvested by centrifugation and re-suspended in 10 ml fresh LB broth with 1% DMSO (dimethyl sulfoxide) (Sigma, USA) as a cryoprotectant. Aliquots of 200 µA are stored at −20° C. until used for transformation wherein a bacterial aliquot is added to 2 ml Brain Heart Infusion Broth (Difco, USA) containing 2% sucrose, 50 µM acetosyringone, pH 5.6 and incubated overnight at 28° C. Bacterial cell density is approximately 1×109 cells per ml.

Cotyledonary explants are exposed to *Agrobacterium* containing the plant transformation vector according to the method of Moloney, et al. (1989), Plant Cell Rep. 8:238-242. The cut surface of the petiole of the explants is briefly submerged into the bacterial culture. The explants are inserted into co-cultivation medium such that the cut surface is in contact with the medium. Ten explants are placed in each 100×15 mm Petri plate. Co-cultivation plates are sealed with STRETCH'N SEAL™ plastic wrap. Plates are incubated for three days in a growth cabinet with temperature and photoperiod conditions, as above, with respect to the seed germination step. The explants are then transferred to selection medium.

After 3 to 4 weeks in the selection medium, regenerating green shoots (putative transformants) are excised and transferred to fresh selection medium for continued growth. When shoots attained a length of 1.5-2.0 cm they are transferred to rooting medium. Putative transgenic shoots are screened for expression of the gus gene essentially as described by Jefferson, R. A. (1987), Plant Mol. Biol. Rep. 5:387-405. The presence of blue staining is regarded as evidence of transformation.

Confirmation of transformation is established by selection on kanamycin, Southern blots, PCR (Polymerase Chain Reaction) and progeny analysis.

Example 10

Selection of Putative Transformants (Transgenic Plants) and Analysis of Transgenic Plants For each construct, seeds are harvested in bulk. Seeds are surface sterilized by submerging them in a solution containing 20% bleach and 0.01% Triton X-100 for 20 minutes, followed by three rinses with sterile water. Sterilized seeds are plated by re-suspending them in sterile 0.1% phytagar at room temperature (about 1 mL phytagar for every 500-1000 seeds), and applying a volume containing 2,000-4,000 seeds onto 150×15 mm kanamycin selection plate. Plates are incubated for two days in the cold without light, and grown for seven to ten days in a controlled environment (22° C. under fluorescent illumination (120 $\mu E \cdot m^{-2} s^{-1}$) in a 16-hour light/ 8-hour dark regime). The selection media contains ½ MSG medium, 0.8% phytagar, 3% sucrose, 50 µg/mL kanamycin and 50 µg/mL Timentin. Petri dishes and lids are sealed with a Micropore™ surgical tape (3M Canada, London, ON, Canada). After seven to ten days, drug resistant plants that have green leaves and well established roots within the medium are identified as transformants and at the three to five leaf stage, selected transformants are transplanted into flats filled with heavily moistened soil mix. Transformants are grown to maturity and mature seeds ($T_2$ generation as defined in Katavic, et al. (1994)) are harvested from individual plants, and further analyzed.

Genomic DNA is isolated from individual $T_1$ plants. PCR amplification is performed to confirm the presence of the cDNA or the gene, respectively, in the $T_1$ transformants. Southern analysis is performed to select the transformants containing a single copy of the inserted fragment. DNA samples are digested with restriction enzymes, resolved by electrophoresis on a 1% agarose gel, and Southern blotting is performed using a nylon filter (Hybond-N+, Amersham). The DGAT2 cDNA fragment, labeled with $\alpha$-[$^{32}$P] dCTP (NEN/ DuPont) is used as a probe. Hybridization is performed at 60° C. The filter is then exposed to Kodak X-OMAT-AR film.

References

Ausubel F. M., R. Brent, R. E. Kingston, D. D. Moore, J. G. Seidman, J. A. Smith, and K. Stuhl, eds (1995). *Current Protocols in Molecular Biology*, Vols 1, 2, and 3. Wiley, New York.

Bechtold N., J. Ellis, and G. Pelletier (1993). In planta *Agrobacterium*-mediated gene transfer by infiltration of adult *Arabidopsis thaliana* plants. C.R. Acad. Sci. Paris, Sciences de la vie/Life sciences 316:1194-1199.

Becker D., R. Brettschneider and H. Lorz (1994). Fertile transgenic wheat from microprojectile bombardment of scutellar tissue. *Plant J.* 5:299-307.

Bradford M. M. (1976). A rapid and sensitive method for the quantification of microgram quantities of protein utilizing the principle of protein-dye binding. *Anal. Biochem.* 72:248-254.

Budziszewski G. J., K. P. C. Croft, and D. F. Hildebrand (1996). Uses of biotechnology in modifying plant lipids. *Lipids* 31:557-569.

Datla R., J. W. Anderson, and G. Selvaraj (1997). Plant promoters for transgene expression. *Biotechnology Annual Review* 3:269-296.

DeBlock M., D. DeBrouwer, and P. Tenning (1989). Transformation of *Brassica napus* and *Brassica oleracea* using *Agrobacterium tumefaciens* and the expression of the bar and neo genes in the transgenic plants. *Plant Physiol.* 91:694-701.

Jefferson R. A. (1987). Assaying chimeric genes in plants: The GUS gene fusion system. *Plant Mol. Biol. Rep.* 5:387-405.

Katavic V., G. W. Haughn, D. Reed, M. Martin, and L. Kunst (1994). In planta transformation of *Arabidopsis thaliana*. *Mol. Gen. Genet.* 245:363-370.

Katavic V., D. W. Reed, D. C. Taylor, E. M. Giblin, D. L. Barton, J.-T. Zou, S. L. MacKenzie, P. S. Covello, and L. Kunst (1995). Alteration of fatty acid composition by an EMS-induced mutation in *Arabidopsis thaliana* affecting diacylglycerol acyltransferase activity. *Plant Physiol.* 108: 399-409.

Kishore G. M. and C. R. Somerville (1993). Genetic engineering of commercially useful biosynthetic pathways in transgenic plants. *Current Opinion in Biotechnology* 4:152-158.

Koncz C. and J. Schell (1986). The promoter of $T_L$-DNA gene 5 controls the tissue-specific expression of chimaeric genes carried by a novel type of *Agrobacterium* binary vector. *Mol. Gen. Genet.* 204:383-396.

MacKenzie S. L. and R. K. Jain (1997). Improvement of oils crops via biotechnology. *Recent Res. Dev. In Oil Chem.* 1:149-158.

Meyer P. (1995). Understanding and controlling transgene expression. *Trends in Biotechnology* 13: 332-337.

Moloney M. M., J. M. Walker, and K. K. Sharma (1989). High efficiency transformation of *Brassica napus* using *Agrobacterium* vectors. *Plant Cell Rep.* 8:238-242.

Nehra N. S., R. N. Chibbar, N. Leung, K. Caswell, C. Mallard, L. Steinhauer; M. Baga, and K. K. Kartha (1994). Self-fertile transgenic wheat plants regenerated from isolated scutellar tissues following microprojectile bombardment with two distinct gene constructs. *Plant J.* 5:285-297.

Potrykus I. (1991). Gene transfer to plants: Assessment of published approaches and results. *Annu. Rev. Plant Physiol. Plant Mol. Biol.* 42:205-225.

Rhodes C. A., D. A. Pierce, I. J. Mettler, D. Mascarenhas, and J. J. Detmer (1988). Genetically transformed maize plants from protoplasts. *Science* 240:204-207.

Sambrook J., E. F. Fritsch, and T. Maniatis (1989). *In Molecular Cloning, A Laboratory Manual,* 2nd edition. Cold Spring Harbor Laboratory Press.

Sanford J. C., T. M. Klein, E. D. Wolf, and N. Allen (1987). Delivery of substances into cells and tissues using a particle bombardment process. *J. Part. Sci. Technol.* 5:27-37.

Shimamoto K., R. Terada, T. Izawa, and H. Fujimoto (1989). Fertile transgenic rice plants regenerated from transformed protoplasts. *Nature* 338:274-276.

Somerville C. R. (1993). Future prospects for genetic modification of the composition of edible oils from higher plants. *Am. J. Clin. Nutr.* 58 (2 Suppl.): 270S-275S.

Songstad D. D., D. A. Somers, and R. J. Griesbach (1995). Advances in alternative DNA delivery techniques. *Plant Cell, Tissue and Organ Culture* 40:1-15.

Southern E. M. (1975). Detection of specific sequences among DNA fragments separated by gel electrophoresis. *J. Mol. Biol.* 98:503-517.

Taylor D. C., N. Weber, D. L. Barton, E. W. Underhill, L. R. Hogge, R. J. Weselake, and M. K. Pomeroy (1991). Triacylglycerol bioassembly in microspore-derived embryos of *Brassica napus* L. cv. Reston. *Plant Physiol.* 97:65-79.

Vasil I. K. (1994). Molecular improvement of cereals. *Plant Mol. Biol.* 25:925-937.

Walden R. and R. Wingender (1995). Gene-transfer and plant regeneration techniques. *Trends in Biotechnology* 13:324-331.

Zou J-T., V. Katavic, E. M. Giblin, D. L. Barton, S. L. MacKenzie, W. A. Keller, X. Hu, and D. C. Taylor (1997). Modification of seed oil content and acyl composition in the Brassicaceae by expression of a yeast sn-2 acyltransferase gene. *The Plant Cell* 9:909-923.

---

What is claimed is:

1. An isolated polypeptide comprising a peptide having at least 90% sequence identity to SEQ ID NO:15, wherein the polypeptide has diacylglycerol acyltransferase activity.

2. The isolated polypeptide of claim 1, wherein the polypeptide has at least 90% sequence identity to SEQ ID NO:1.

3. A nucleic acid molecule comprising a heterologous promoter operably linked to a polynucleotide encoding a polypeptide comprisinq a peptide having at least 90% sequence identity to SEQ ID NO:15, wherein the encoded polypeptide has diacylglycerol acyltransferase activity.

4. A vector comprising a polynucleotide encoding a polypeptide comprising a peptide having at least 90% sequence identity to SEQ ID NO:15, wherein the encoded polypeptide has diacylglycerol acyltransferase activity.

5. A transgenic plant cell comprising the nucleic acid molecule of claim 3.

6. A yeast cell transformed with the nucleic acid molecule of claim 3.

7. A method of altering levels of very long chain polyunsaturated fatty acids in a plant, the method comprising:
introducing into the plant the nucleic acid molecule of claim 3.

8. The method according to claim 7, wherein the nucleic acid molecule is introduced into the plant by *Agrobacterium*-mediated transformation.

9. The method according to claim 7, wherein the method further comprises
introducing into the plant a polynucleotide encoding a polypeptide with pyruvate dehydrogenase kinase activity.

10. The method according to claim 7, wherein the method further comprises
introducing into the plant a polynucleotide encoding a polypeptide with diacylglycerol acetyltransferase activity.

11. The method according to claim 7, wherein the method further comprises
introducing into the plant a polynucleotide encoding a polypeptide with glycerol-3-phosphate dehydrogenase activity.

12. The method according to claim 7, wherein the plant is selected from the group consisting of *Arabidopsis thaliana, Borago* spp., Canola, *Ricinus* spp., *Theobroma* spp., *Zea* spp., *Gossypium* spp, *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Carthamus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae.

13. A plant produced by a method comprising introducing into the plant a nucleic acid molecule encoding a polypeptide comprising a peptide having at least 90% sequence identity to SEQ ID NO:15.

14. A seed harvested from the plant of claim 13, wherein the seed comprises a polynucleotide encoding a polypeptide comprising a peptide having at least 90% sequence identity to SEQ ID NO:15, wherein the encoded polypeptide has diacylglycerol acyltransferase activity.

15. The method according to claim 7, wherein the method comprises:
harvesting a seed from the plant; and
extracting oil from the harvested seed.

16. A transgenic plant comprising the plant cell of claim 5.

17. The method according to claim 9, wherein the polypeptide with pyruvate dehydrogenase kinase activity is from a plant of the genus *Brassica*.

18. The transgenic plant of claim 16, wherein the transgenic plant is a *Brassica* plant, and wherein the plant has altered levels of polyunsaturated fatty acids in seeds as compared to levels in a plant of the same species lacking the polynucleotide.

19. The transgenic plant of claim 16, wherein the transgenic plant is a
*Brassica* plant, and wherein the fatty acids in the plant are more than 70% polyunsaturated
fatty acids.

* * * * *

UNITED STATES PATENT AND TRADEMARK OFFICE
CERTIFICATE OF CORRECTION

PATENT NO. : 8,658,855 B2  Page 1 of 1
APPLICATION NO. : 12/735132
DATED : February 25, 2014
INVENTOR(S) : Jitao Zou, Jingyu Xu and Zhifu Zheng It is certified that error appears in the above-identified patent and that said Letters Patent is hereby corrected as shown below:

In the specification:
COLUMN 1, LINE 8, change "61/008,742" to --61/008,752--

Signed and Sealed this
First Day of March, 2016

Michelle K. Lee
*Director of the United States Patent and Trademark Office*

SEQUENCE LISTING

<160> NUMBER OF SEQ ID NOS: 64

<210> SEQ ID NO 1
<211> LENGTH: 456
<212> TYPE: PRT
<213> ORGANISM: T. pseudonana

<400> SEQUENCE: 1

```
Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Val Gly Ser
        35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
            100                 105                 110

Ser Gln Glu Met Asn Glu Gln Glu Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255
```

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
            275                 280                 285

Pro Tyr Thr Ser Asp His Pro Gly Arg Val Gly Val Ser Pro Gly Gly
            290                 295                 300

Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
            325                 330                 335

Met Lys His Lys Leu Pro Ile Val Pro Val Tyr Cys Phe Gly Ala Thr
            340                 345                 350

Lys Met Leu Arg Arg Val Gln Leu Pro Ala Phe Val Glu Thr Leu Ser
            355                 360                 365

Arg Met Leu Lys Ile Ser Leu Cys Leu Phe Gly Lys Leu Gly Leu
            370                 375                 380

Pro Ile Pro Phe Arg Gln Arg Leu Met Tyr Val Met Gly Lys Thr Leu
385                 390                 395                 400

Phe Pro Pro Leu Pro Arg Asp Gly Val Asn Thr Ser Met Met Glu Gly
            405                 410                 415

Gly Glu Glu Phe Asp Gly Arg Val Gln Glu Met His Asp Ala Phe Cys
            420                 425                 430

Asn Glu Ile Thr Arg Ile Phe Glu Arg Asn Lys Asp His Tyr Gly Trp
            435                 440                 445

Gly Asn Lys Asn Leu Arg Leu Val
450                 455

<210> SEQ ID NO 2
<211> LENGTH: 1432
<212> TYPE: DNA
<213> ORGANISM: T. pseudonana

<400> SEQUENCE: 2
atgacaacaa agaagcgtcc actacccgt catctgcacc ttccacctgg agtagaagta      60
ctcgtctctc caccacccta cgaagtatgc acgctcgtcg acagattgtt ggtctacgcc    120
tcgtcgttga ttgtcgttgg atctcccgtt tggtttacg gaggcatcat ttatttttac     180
aggaagtgga agaagtatcg ttctcttgct gctgctactg aggctgcgag acatgagagt    240
ggtggcggtg tgcatcgtc aacggttcgt tgcagaggta cacgtcaacg tacatcgtct     300
gatgacggca actacacatc gtcaactggc gaaagctcgc aagaaatgaa cgaacaagag    360
acacaaacac aatcacatcg acaacaaaca gagcaataca caactacaa acgattagca     420 acaagatacg gagtagcact cgctgcaatc attctcatat ccatctgggg gcctcatcgt    480
gacaagcgtg taggagaatg gctcggtgtc aagaagtgga gattgtggga tgcatggttg    540
aactatgttg gattcactgt actaaaggac aatggagatg atgaccacac aataatacaa    600
acgaatccac actcagcaat acccaatcaa gaagagtttg acatacacac atctccatca    660
atcttcgcat tcgtacccca cggcatcttt cctttcggac tcgccttttc atgtctaccc    720
gaacgaggac acgaacaaac atggggtctc ttccgaccag tcgttgcaac agccaccaaa    780 ctcttttccgc tggtacgaac cttcattct tggatgaacg gagtggatgc ttcgcgttcg    840
gcggtgtctc gtgctcttgc tcctccgtat accagtgatc atccgggaag agtgggagtt    900
tcgcccggtg gtattgccga gatgtttgag acgtatccaa agccggggtt tcatcctaat    960

```
gacgaggcag cattgttaaa agatcggaat ggattgttca agcttgcgat gaaacacaag   1020
ctgccgattg ttccggtgta ctgctttgga gctacaaaga tgttgagacg agtgcaatta   1080
cctgcgtttg tggagacgtt gagcagaatg ctcaagatca gtctttgttt attctttgga   1140
aagcttgggt tgcctattcc tttccgacag cggctgatgt atgtcatggg caagacgttg   1200
tttcctcctc tgccgagaga tggcgtgaac acttctatga tggaaggagg agaagaattt   1260
gatgaacgag tgcaagagat gcatgatgca ttctgcaatg agataactcg catcttcgag   1320
cgaaacaaag accactacgg ttggggtaac aaaaacttga gactcgtatg agagtgtgag   1380
tgatattcat atgcaactct taacttaaag ccacagacca cacaggcaca aa            1432
```

<210> SEQ ID NO 3
<211> LENGTH: 456
<212> TYPE: PRT
<213> ORGANISM: Artificial
<220> FEATURE:
<223> OTHER INFORMATION: K171R mutant

<400> SEQUENCE: 3

```
Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
                20                  25                  30

Val Asp Arg Leu Leu Val Tyr Ala Ser Ser Leu Ile Val Val Gly Ser
                35                  40                  45

Pro Val Trp Phe Tyr Gly Gly Ile Ile Tyr Phe Tyr Arg Lys Trp Lys
        50                  55                  60

Leu Tyr Arg Ser Lys Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
                100                 105                 110

Ser Gln Glu Met Asn Glu Gln Glu Thr Gln Thr Gln Ser His Arg Gln
            115                 120                 125

Gln Thr Glu Gln Tyr Asn Asn Tyr Lys Arg Leu Ala Thr Arg Tyr Gly
        130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Arg Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285
```

-continued

```
Pro Tyr Thr Ser Asp His Pro Gly Arg Val Gly Val Ser Pro Gly Gly
        290                 295                 300

Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
                325                 330                 335

Met Lys His Lys Leu Pro Ile Val Pro Val Tyr Cys Phe Gly Ala Thr
                    340                 345                 350

Lys Met Leu Arg Arg Val Gln Leu Pro Ala Phe Val Glu Thr Leu Ser
            355                 360                 365

Arg Met Leu Lys Ile Ser Leu Cys Leu Phe Phe Gly Lys Leu Gly Leu
370                 375                 380

Pro Ile Pro Phe Arg Gln Arg Leu Met Tyr Val Met Gly Lys Thr Leu
385                 390                 395                 400

Phe Pro Pro Leu Pro Arg Asp Gly Val Asn Thr Ser Met Met Glu Gly
                405                 410                 415

Gly Glu Glu Phe Asp Gly Arg Val Gln Glu Met His Asp Ala Phe Cys
                420                 425                 430

Asn Glu Ile Thr Arg Ile Phe Glu Arg Asn Lys Asp His Tyr Gly Trp
                435                 440                 445

Gly Asn Lys Asn Leu Arg Leu Val
450                 455

<210> SEQ ID NO 4
<211> LENGTH: 1432
<212> TYPE: DNA
<213> ORGANISM: Artificial
<220> FEATURE:
<223> OTHER INFORMATION: K171R mutant

<400> SEQUENCE: 4
atgacaacaa agaagcgtcc actacccegt catctgcacc ttccacctgg agtagaagta      60
ctcgtctctc caccacccta cgaagtatgc acgctcgtcg acagattgtt ggtctacgcc     120
tcgtcgttga ttgtcgttgg atctcccgtt tggttctacg aggcatcat ttattttac       180 aggaagtgga agaagtatcg ttctcttgct gctgctactg aggctgcgag acatgagagt     240
ggtggcggtg gtgcatcgtc aacggttcgt tgcagaggta cacgtcaacg tacatcgtct     300
gatgacggca actacacatc gtcaactggc gaaagctcgc aagaaatgaa cgaacaagag     360
acacaaacac aatcacatcg acaacaaaca gagcaataca caactacaa acgattagca     420 acaagatacg gagtagcact cgctgcaatc attctcatat ccatctgggg gcctcatcgt     480
gacaagcgtg taggagaatg gctcggtgtc aggaagtgga gattgtggga tgcatggttg     540
aactatgttg gattcactgt actaaaggac aatggagatg atgaccacac aataatacaa     600
acgaatccac actcagcaat acccaatcaa gaagagtttg acatacacac atctccatca     660
atcttcgcat tcgtaccca cggcatcttt cctttcggac tcgcctttc atgtctaccc       720 gaacgaggac acgaacaaac atggggtctc ttccgaccag tcgttgcaac agccaccaaa     780
ctctttccgc tggtacgaac cttcatttct ggatgaacg gagtggatgc ttcgcgttcg      840
gcggtgtctc gtgctcttgc tcctccgtat accagtgatc atccgggaag agtgggagtt     900
tcgcccggtg gtattgccga gatgtttgag acgtatccaa agccggggtt tcatcctaat     960
gacgaggcag cattgttaaa agatcggaat ggattgttca gcttgcgat gaaacacaag    1020 ctgccgattt ttccggtgta ctgctttgga gctacaaaga tgttgagacg agtgcaatta   1080
cctgcgtttg tggagacgtt gagcagaatg ctcaagatca gtctttgttt attctttgga   1140
```

```
aagcttgggt tgcctattcc tttccgacag cggctgatgt atgtcatggg caagacgttg    1200
tttcctcctc tgccgagaga tggcgtgaac acttctatga tggaaggagg agaagaattt    1260
gatgaacgag tgcaagagat gcatgatgca ttctgcaatg agataactcg catcttcgag    1320
cgaaacaaag accactacgg ttggggtaac aaaaacttga gactcgtatg agagtgtgag    1380
tgatattcat atgcaactct taacttaaag ccacagacca cacaggcaca aa             1432
```

```
<210> SEQ ID NO 5
<211> LENGTH: 456
<212> TYPE: PRT
<213> ORGANISM: Artificial
<220> FEATURE:
<223> OTHER INFORMATION: F224Y mutant

<400> SEQUENCE: 5
```

| Met | Thr | Thr | Lys | Lys | Arg | Pro | Lys | Pro | Arg | His | Lys | His | Leu | Pro | Pro |
|---|---|---|---|---|---|---|---|---|---|---|---|---|---|---|---|
| 1 | | | | 5 | | | | | 10 | | | | | 15 | |

| Gly | Val | Glu | Val | Leu | Val | Ser | Pro | Pro | Tyr | Glu | Val | Cys | Thr | Leu |
|---|---|---|---|---|---|---|---|---|---|---|---|---|---|---|
| | | | 20 | | | | | 25 | | | | 30 | | |

| Val | Asp | Arg | Leu | Leu | Val | Tyr | Ala | Ser | Ser | Leu | Ile | Val | Val | Gly | Ser |
|---|---|---|---|---|---|---|---|---|---|---|---|---|---|---|---|
| | | 35 | | | | | 40 | | | | | 45 | | | |

| Pro | Val | Trp | Phe | Tyr | Gly | Gly | Ile | Ile | Tyr | Phe | Tyr | Arg | Lys | Trp | Lys |
|---|---|---|---|---|---|---|---|---|---|---|---|---|---|---|---|
| | 50 | | | | | 55 | | | | | 60 | | | | |

| Leu | Tyr | Arg | Ser | Lys | Ala | Ala | Ala | Thr | Phe | Ala | Ala | Arg | His | Glu | Ser |
|---|---|---|---|---|---|---|---|---|---|---|---|---|---|---|---|
| 65 | | | | | 70 | | | | | 75 | | | | | 80 |

| Gly | Gly | Gly | Gly | Ala | Ser | Ser | Thr | Val | Arg | Cys | Arg | Gly | Thr | Arg | Gln |
|---|---|---|---|---|---|---|---|---|---|---|---|---|---|---|---|
| | | | | 85 | | | | | 90 | | | | | 95 | |

| Arg | Thr | Ser | Ser | Asp | Asp | Gly | Asn | Tyr | Thr | Ser | Ser | Thr | Gly | Glu | Ser |
|---|---|---|---|---|---|---|---|---|---|---|---|---|---|---|---|
| | | | 100 | | | | | 105 | | | | | 110 | | |

| Ser | Gln | Glu | Met | Asn | Glu | Gln | Glu | Thr | Gln | Thr | Gln | Ser | His | Arg | Gln |
|---|---|---|---|---|---|---|---|---|---|---|---|---|---|---|---|
| | | | 115 | | | | | 120 | | | | | 125 | | |

| Gln | Thr | Glu | Gln | Tyr | Asn | Asn | Tyr | Lys | Arg | Leu | Ala | Thr | Arg | Tyr | Gly |
|---|---|---|---|---|---|---|---|---|---|---|---|---|---|---|---|
| | 130 | | | | | 135 | | | | | 140 | | | | |

| Val | Ala | Lys | Ala | Ala | Ile | Ile | Lys | Ile | Ser | Ile | Trp | Gly | Pro | His | Arg |
|---|---|---|---|---|---|---|---|---|---|---|---|---|---|---|---|
| 145 | | | | | 150 | | | | | 155 | | | | | 160 |

| Asp | Lys | Arg | Val | Gly | Glu | Trp | Leu | Gly | Val | Lys | Lys | Trp | Arg | Leu | Trp |
|---|---|---|---|---|---|---|---|---|---|---|---|---|---|---|---|
| | | | | 165 | | | | | 170 | | | | | 175 | |

| Asp | Ala | Trp | Leu | Asn | Tyr | Val | Gly | Phe | Thr | Val | Leu | Lys | Asp | Asn | Gly |
|---|---|---|---|---|---|---|---|---|---|---|---|---|---|---|---|
| | | | 180 | | | | | 185 | | | | | 190 | | |

| Asp | Asp | Asp | His | Thr | Ile | Ile | Glu | Thr | Asn | Pro | His | Ser | Ala | Ile | Pro |
|---|---|---|---|---|---|---|---|---|---|---|---|---|---|---|---|
| | | | 195 | | | | | 200 | | | | | 205 | | |

| Asn | Gln | Glu | Glu | Phe | Asp | Ile | His | Thr | Ser | Pro | Ser | Ile | Phe | Ala | Tyr |
|---|---|---|---|---|---|---|---|---|---|---|---|---|---|---|---|
| | 210 | | | | | 215 | | | | | 220 | | | | |

| Val | Pro | His | Gly | Ile | Phe | Pro | Phe | Gly | Leu | Ala | Phe | Ser | Cys | Leu | Pro |
|---|---|---|---|---|---|---|---|---|---|---|---|---|---|---|---|
| 225 | | | | | 230 | | | | | 235 | | | | | 240 |

| Glu | Arg | Gly | His | Glu | Gln | Thr | Trp | Gly | Leu | Phe | Arg | Pro | Val | Val | Ala |
|---|---|---|---|---|---|---|---|---|---|---|---|---|---|---|---|
| | | | | 245 | | | | | 250 | | | | | 255 | |

| Thr | Ala | Thr | Lys | Leu | Phe | Pro | Leu | Val | Arg | Thr | Phe | Ile | Ser | Trp | Met |
|---|---|---|---|---|---|---|---|---|---|---|---|---|---|---|---|
| | | | 260 | | | | | 265 | | | | | 270 | | |

| Asn | Gly | Val | Asp | Ala | Ser | Asp | Ser | Ala | Val | Ser | Arg | Ala | Leu | Ala | Pro |
|---|---|---|---|---|---|---|---|---|---|---|---|---|---|---|---|
| | | | 275 | | | | | 280 | | | | | 285 | | |

| Pro | Tyr | Thr | Ser | Asp | His | Pro | Gly | Arg | Val | Gly | Val | Ser | Pro | Gly | Gly |
|---|---|---|---|---|---|---|---|---|---|---|---|---|---|---|---|
| | 290 | | | | | 295 | | | | | 300 | | | | |

| Ile | Ala | Glu | Met | Phe | Glu | Thr | Tyr | Pro | Lys | Pro | Gly | Phe | His | Pro | Asn |
|---|---|---|---|---|---|---|---|---|---|---|---|---|---|---|---|
| 305 | | | | | 310 | | | | | 315 | | | | | 320 |

Asp Glu Ala Ala Leu Leu Lys Asp Arg Asn Gly Phe Lys Leu Ala
              325                 330                 335

Met Lys His Lys Leu Pro Ile Val Pro Val Tyr Cys Phe Gly Ala Thr
              340                 345                 350

Lys Met Leu Arg Arg Val Gln Leu Pro Ala Phe Val Glu Thr Leu Ser
              355                 360                 365

Arg Met Leu Lys Ile Ser Leu Cys Leu Phe Phe Gly Lys Leu Gly Leu
              370                 375                 380

Pro Ile Pro Phe Arg Gln Arg Leu Met Tyr Val Met Gly Lys Thr Leu
385                 390                 395                 400

Phe Pro Pro Leu Pro Arg Asp Gly Val Asn Thr Ser Met Met Glu Gly
              405                 410                 415

Gly Glu Glu Phe Asp Gly Arg Val Gln Glu Met His Asp Ala Phe Cys
              420                 425                 430

Asn Glu Ile Thr Arg Ile Phe Glu Arg Asn Lys Asp His Tyr Gly Trp
              435                 440                 445

Gly Asn Lys Asn Leu Arg Leu Val
450                 455

<210> SEQ ID NO 6
<211> LENGTH: 1432
<212> TYPE: DNA
<213> ORGANISM: Artificial
<220> FEATURE:
<223> OTHER INFORMATION: F224Y mutant

<400> SEQUENCE: 6
atgacaacaa agaagcgtcc actaccccgt catctgcacc ttccacctgg agtagaagta     60
ctcgtctctc caccacccta cgaagtatgc acgctcgtcg acagattgtt ggtctacgcc    120
tcgtcgttga ttgtcgttgg atctcccgtt tggttctacg aggcatcat ttattttac     180 aggaagtgga agaagtatcg ttctcttgct gctgctactg aggctgcgag acatgagagt    240
ggtggcggtg gtgcatcgtc aacggttcgt tgcagaggta cacgtcaacg tacatcgtct    300
gatgacggca actacacatc gtcaactggc gaaagctcgc aagaaatgaa cgaacaagag    360
acacaaacac aatcacatcg acaacaaaca gagcaataca caactacaa acgattagca    420 acaagatacg gagtagcact cgctgcaatc attctcatat ccatctgggg gcctcatcgt    480
gacaagcgtg taggagaatg gctcggtgtc aagaagtgga gattgtggga tgcatggttg    540
aactatgttg gattcactgt actaaaggac aatggagatg atgaccacac aataatacaa    600
acgaatccac actcagcaat acccaatcaa gaagagtttg acatacacac atctccatca    660
atcttcgcat acgtacccca cggcatcttt cctttcggac tcgccttttc atgtctaccc    720
gaacgaggac acgaacaaac atggggtctc ttccgaccag tcgttgcaac agccaccaaa    780
ctctttccgc tggtacgaac cttcatttct tggatgaacg gagtggatgc ttcgcgttcg    840
gcggtgtctc gtgctcttgc tcctccgtat accagtgatc atccgggaag agtgggagtt    900
tcgcccggtg gtattgccga gatgtttgag acgtatccaa agccgggtt tcatcctaat    960 gacgaggcag cattgttaaa agatcggaat ggattgttca gcttgcgat gaaacacaag   1020 ctgccgattg ttccggtgta ctgctttgga gctacaaaga tgttgagacg agtgcaatta   1080
cctgcgtttg tggagacgtt gagcagaatg ctcaagatca gtctttgttt attctttgga   1140
aagcttgggt tgcctattcc tttccgacag cggctgatgt atgtcatggg caagacgttg   1200
tttcctcctc tgccgagaga tggcgtgaac acttctatga tggaaggagg agaagaattt   1260

```
gatgaacgag tgcaagagat gcatgatgca ttctgcaatg agataactcg catcttcgag   1320
cgaaacaaag accactacgg ttggggtaac aaaaacttga gactcgtatg agagtgtgag   1380
tgatattcat atgcaactct aacttaaaag ccacagacca cacaggcaca aa           1432

<210> SEQ ID NO 7
<211> LENGTH: 456
<212> TYPE: PRT
<213> ORGANISM: Artificial
<220> FEATURE:
<223> OTHER INFORMATION: V298I mutant

<400> SEQUENCE: 7
```

Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Gly Ser
        35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
            100                 105                 110

Ser Gln Glu Met Asn Glu Gln Glu Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285

Pro Tyr Thr Ser Asp His Pro Gly Arg Ile Gly Val Ser Pro Gly Gly
    290                 295                 300

Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
                325                 330                 335

Met Lys His Lys Leu Pro Ile Val Pro Val Tyr Cys Phe Gly Ala Thr

|     |     |     |     | 340 |     |     |     |     | 345 |     |     |     |     | 350 |     |
| --- | --- | --- | --- | --- | --- | --- | --- | --- | --- | --- | --- | --- | --- | --- | --- |
| Lys | Met | Leu | Arg | Arg | Val | Gln | Leu | Pro | Ala | Phe | Val | Glu | Thr | Leu | Ser |
|     |     |     |     |     | 355 |     |     |     |     | 360 |     |     |     |     | 365 |     |
| Arg | Met | Leu | Lys | Ile | Ser | Leu | Cys | Leu | Phe | Phe | Gly | Lys | Leu | Gly | Leu |
|     |     |     |     |     | 370 |     |     |     |     | 375 |     |     |     |     | 380 |     |
| Pro | Ile | Pro | Phe | Arg | Gln | Arg | Leu | Met | Tyr | Val | Met | Gly | Lys | Thr | Leu |
| 385 |     |     |     |     | 390 |     |     |     |     | 395 |     |     |     |     | 400 |
| Phe | Pro | Pro | Leu | Pro | Arg | Asp | Gly | Val | Asn | Thr | Ser | Met | Met | Glu | Gly |
|     |     |     |     | 405 |     |     |     |     | 410 |     |     |     |     | 415 |     |
| Gly | Glu | Glu | Phe | Asp | Gly | Arg | Val | Gln | Glu | Met | His | Asp | Ala | Phe | Cys |
|     |     |     | 420 |     |     |     |     | 425 |     |     |     |     | 430 |     |     |
| Asn | Glu | Ile | Thr | Arg | Ile | Phe | Glu | Arg | Asn | Lys | Asp | His | Tyr | Gly | Trp |
|     |     |     | 435 |     |     |     |     | 440 |     |     |     |     | 445 |     |     |
| Gly | Asn | Lys | Asn | Leu | Arg | Leu | Val |     |     |     |     |     |     |     |     |
|     |     |     | 450 |     |     |     | 455 |     |     |     |     |     |     |     |     |

<210> SEQ ID NO 8
<211> LENGTH: 1432
<212> TYPE: DNA
<213> ORGANISM: Artificial
<220> FEATURE:
<223> OTHER INFORMATION: V298I mutant

<400> SEQUENCE: 8

```
atgacaacaa agaagcgtcc actacccccgt catctgcacc ttccacctgg agtagaagta      60
ctcgtctctc caccaccccta cgaagtatgc acgctcgtcg acagattgtt ggtctacgcc     120
tcgtcgttga ttgtcgttgg atctcccgtt tggttctacg gaggcatcat ttattttac      180
aggaagtgga gaagtatcg ttctcttgct gctgctactg aggctgcgag acatgagagt      240
ggtggcggtg gtgcatcgtc aacggttcgt tgcagaggta cacgtcaacg tacatcgtct     300
gatgacggca actacacatc gtcaactggc gaaagctcgc aagaaatgaa cgaacaagag     360
acacaaacac aatcacatcg acaacaaaca gagcaataca caactacaa acgattagca     420
acaagatacg gagtagcact cgctgcaatc attctcatat ccatctgggg gcctcatcgt     480
gacaagcgtg taggagaatg gctcggtgtc aagaagtgga gattgtggga tgcatggttg     540
aactatgttg gattcactgt actaaaggac aatggagatg atgaccacac aataatacaa     600
acgaatccac actcagcaat acccaatcaa gaagagtttg acatacacac atctccatca     660
atcttcgcat tcgtacccca cggcatcttt cctttcggac tcgccttttc atgtctaccc     720
gaacgaggac acgaacaaac atgggtgtc ttccgaccag tcgttgcaac agccaccaaa     780
ctctttccgc tggtacgaac cttcatttct tggatgaacg gagtggatgc ttcgcgttcg     840
gcggtgtctc gtgctcttgc tcctccgtat accagtgatc atccgggaag aatcggagtt     900
tcgcccggtg gtattgccga gatgtttgag acgtatccaa agccggggtt tcatcctaat     960
gacgaggcag cattgttaaa agatcggaat ggattgttca agcttgcgat gaaacacaag    1020
ctgccgattg ttccggtgta ctgctttgga gctacaaaga tgttgagacg agtgcaatta    1080
cctgcgtttg tggagacgtt gagcagaatg ctcaagatca gtctttgttt atttcttgga    1140
aagcttgggt tgcctattcc tttccgacag cggctgatgt atgtcatggg caagacgttg    1200
tttcctcctc tgccgagaga tggcgtgaac acttctatga tggaaggagg agaagaattt    1260
gatgaacgag tgcaagagat gcatgatgca ttctgcaatg agataactcg catcttcgag    1320
cgaaacaaag accactacgg ttggggtaac aaaaacttga gactcgtatg agagtgtgag    1380
tgatattcat atgcaactct taacttaaag ccacagacca cacaggcaca aa            1432
```

<210> SEQ ID NO 9
<211> LENGTH: 456
<212> TYPE: PRT
<213> ORGANISM: Artificial
<220> FEATURE:
<223> OTHER INFORMATION: I343L mutant

<400> SEQUENCE: 9

Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Val Gly Ser
            35                  40                  45

Pro Val Trp Phe Tyr Gly Gly Ile Ile Tyr Phe Tyr Arg Lys Trp Lys
        50                  55                  60

Leu Tyr Arg Ser Lys Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
            100                 105                 110

Ser Gln Glu Met Asn Glu Gln Thr Gln Thr Gln Ser His Arg Gln
            115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285

Pro Tyr Thr Ser Asp His Pro Gly Arg Val Gly Val Ser Pro Gly Gly
    290                 295                 300

Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
                325                 330                 335

Met Lys His Lys Leu Pro Leu Val Pro Val Tyr Cys Phe Gly Ala Thr
            340                 345                 350

Lys Met Leu Arg Arg Val Gln Leu Pro Ala Phe Val Glu Thr Leu Ser
        355                 360                 365

```
Arg Met Leu Lys Ile Ser Leu Cys Leu Phe Phe Gly Lys Leu Gly Leu
        370                 375                 380
Pro Ile Pro Phe Arg Gln Arg Leu Met Tyr Val Met Gly Lys Thr Leu
385                 390                 395                 400
Phe Pro Pro Leu Pro Arg Asp Gly Val Asn Thr Ser Met Met Glu Gly
                405                 410                 415
Gly Glu Glu Phe Asp Gly Arg Val Gln Glu Met His Asp Ala Phe Cys
            420                 425                 430
Asn Glu Ile Thr Arg Ile Phe Glu Arg Asn Lys Asp His Tyr Gly Trp
        435                 440                 445
Gly Asn Lys Asn Leu Arg Leu Val
        450                 455

<210> SEQ ID NO 10
<211> LENGTH: 1432
<212> TYPE: DNA
<213> ORGANISM: Artificial
<220> FEATURE:
<223> OTHER INFORMATION: I343L mutant

<400> SEQUENCE: 10
atgacaacaa agaagcgtcc actacccgt catctgcacc ttccacctgg agtagaagta      60
ctcgtctctc caccaccta cgaagtatgc acgctcgtcg acagattgtt ggtctacgcc     120
tcgtcgttga ttgtcgttgg atctcccgtt tggttctacg gaggcatcat ttattttac    180 aggaagtgga gaagtatcg ttctcttgct gctgctactg aggctgcgag acatgagagt     240
ggtggcggtg gtgcatcgtc aacggttcgt tgcagaggta cacgtcaacg tacatcgtct     300
gatgacggca actacacatc gtcaactggc gaaagctcgc aagaaatgaa cgaacaagag     360
acacaaacac aatcacatcg acaacaaaca gagcaataca caactacaa acgattagca     420 acaagatacg gagtagcact cgctgcaatc attctcatat ccatctgggg gcctcatcgt     480
gacaagcgtg taggagaatg gctcggtgtc aagaagtgga gattgtggga tgcatggttg     540
aactatgttg gattcactgt actaaaggac aatggagatg atgaccacac aataatacaa     600
acgaatccac actcagcaat acccaatcaa gaagagtttg acatacacac atctccatca     660
atcttcgcat tcgtacccca cggcatcttt cctttcggac tcgccttttc atgtctaccc     720
gaacgaggac acgaacaaac atggggtctc ttccgaccag tcgttgcaac agccaccaaa     780
ctctttccgc tggtacgaac cttcatttct tggatgaacg gagtggatgc ttcgcgttcg     840
gcggtgtctc gtgctcttgc cctccgtat accagtgatc atccgggaag agtgggagtt     900
tcgcccggtg gtattgccga tgtttgag acgtatccaa agccggggtt tcatcctaat     960
gacgaggcag cattgttaaa agatcggaat ggattgttca agcttgcgat gaaacacaag    1020
ctgccgcttg ttccggtgta ctgctttgga gctacaaaga tgttgagacg agtgcaatta    1080
cctgcgtttg tggagacgtt gagcagaatg ctcaagatca gtctttgttt attctttgga    1140
aagcttgggt tgcctattcc tttccgacag cggctgatgt atgtcatggg caagacgttg    1200
tttcctcctc tgccgagaga tggcgtgaac acttctatga tggaaggagg agaagaattt    1260
gatgaacgag tgcaagagat gcatgatgca ttctgcaatg agataactcg catcttcgag    1320
cgaaacaaag accactacgg ttggggtaac aaaaacttga gactcgtatg agagtgtgag    1380
tgatattcat atgcaactct taacttaaag ccacagacca cacaggcaca aa            1432

<210> SEQ ID NO 11
<211> LENGTH: 456
<212> TYPE: PRT
```

<213> ORGANISM: Artificial
<220> FEATURE:
<223> OTHER INFORMATION: E365K mutant

<400> SEQUENCE: 11

```
Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
            20                  25                  30

Val Asp Arg Leu Leu Val Tyr Ala Ser Ser Leu Ile Val Val Gly Ser
        35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
                100                 105                 110

Ser Gln Glu Met Asn Glu Gln Glu Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
        195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
                245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
        275                 280                 285

Pro Tyr Thr Ser Asp His Pro Gly Arg Val Gly Val Ser Pro Gly Gly
    290                 295                 300

Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
                325                 330                 335

Met Lys His Lys Leu Pro Ile Val Pro Val Tyr Cys Phe Gly Ala Thr
            340                 345                 350

Lys Met Leu Arg Arg Val Gln Leu Pro Ala Phe Val Lys Thr Leu Ser
        355                 360                 365

Arg Met Leu Lys Ile Ser Leu Cys Leu Phe Phe Gly Lys Leu Gly Leu
    370                 375                 380

Pro Ile Pro Phe Arg Gln Arg Leu Met Tyr Val Met Gly Lys Thr Leu
385                 390                 395                 400
```

Phe Pro Pro Leu Pro Arg Asp Gly Val Asn Thr Ser Met Met Glu Gly
                405                 410                 415

Gly Glu Glu Phe Asp Gly Arg Val Gln Glu Met His Asp Ala Phe Cys
            420                 425                 430

Asn Glu Ile Thr Arg Ile Phe Glu Arg Asn Lys Asp His Tyr Gly Trp
        435                 440                 445

Gly Asn Lys Asn Leu Arg Leu Val
    450                 455

<210> SEQ ID NO 12
<211> LENGTH: 1432
<212> TYPE: DNA
<213> ORGANISM: Artificial
<220> FEATURE:
<223> OTHER INFORMATION: E365K mutant

<400> SEQUENCE: 12

| | | |
|---|---|---|
| atgacaacaa agaagcgtcc actacccgt catctgcacc ttccacctgg agtagaagta | 60 |
| ctcgtctctc caccaccta cgaagtatgc acgctcgtcg acagattgtt ggtctacgcc | 120 |
| tcgtcgttga ttgtcgttgg atctcccgtt tggttctacg gaggcatcat ttattttttac | 180 |
| aggaagtgga agaagtatcg ttctcttgct gctgctactg aggctgcgag acatgagagt | 240 |
| ggtggcggtg gtgcatcgtc aacggttcgt tgcagaggta cacgtcaacg tacatcgtct | 300 |
| gatgacggca actacacatc gtcaactggc gaaagctcgc aagaaatgaa cgaacaagag | 360 |
| acacaaacac aatcacatcg acaacaaaca gagcaataca caactacaa acgattagca | 420 |
| acaagatacg gagtagcact cgctgcaatc attctcatat ccatctgggg gcctcatcgt | 480 |
| gacaagcgtg taggagaatg gctcggtgtc aagaagtgga gattgtggga tgcatggttg | 540 |
| aactatgttg gattcactgt actaaaggac aatggagatg atgaccacac aataatacaa | 600 |
| acgaatccac actcagcaat acccaatcaa gaagagtttg acatacacac atctccatca | 660 |
| atcttcgcat tcgtacccca cggcatcttt cctttcggac tcgccttttc atgtctaccc | 720 |
| gaacgaggac acgaacaaac atgggggtctc ttccgaccag tcgttgcaac agccaccaaa | 780 |
| ctctttccgc tggtacgaac cttcatttct tggatgaacg gagtggatgc ttcgcgttcg | 840 |
| gcggtgtctc gtgctcttgc tcctccgtat accagtgatc atccgggaag agtgggagtt | 900 |
| tcgcccggtg gtattgccga gatgtttgag acgtatccaa agccggggtt tcatcctaat | 960 |
| gacgaggcag cattgttaaa agatcggaat ggattgttca agcttgcgat gaaacacaag | 1020 |
| ctgccgattg ttccggtgta ctgctttgga gctacaaaga tgttgagacg agtgcaatta | 1080 |
| cctgcgtttg tgaagacgtt gagcagaatg ctcaagatca gtctttgttt attctttgga | 1140 |
| aagcttgggt tgcctattcc tttccgacag cggctgatgt atgtcatggg caagacgttg | 1200 |
| tttcctcctc tgccgagaga tggcgtgaac acttctatga tggaaggagg agaagaattt | 1260 |
| gatgaacgag tgcaagagat gcatgatgca ttctgcaatg agataactcg catcttcgag | 1320 |
| cgaaacaaag accactacgg ttggggtaac aaaaacttga gactcgtatg agagtgtgag | 1380 |
| tgatattcat atgcaactct taacttaaag ccacagacca cacaggcaca aa | 1432 |

<210> SEQ ID NO 13
<211> LENGTH: 456
<212> TYPE: PRT
<213> ORGANISM: Artificial
<220> FEATURE:
<223> OTHER INFORMATION: L400I mutant

<400> SEQUENCE: 13

Met Thr Thr Lys Lys Arg Pro Lys Pro Arg His Lys His Leu Pro Pro
1               5                   10                  15

Gly Val Glu Val Leu Val Ser Pro Pro Tyr Glu Val Cys Thr Leu
        20                  25                  30

Val Asp Arg Leu Leu Val Tyr Ala Ser Ser Leu Ile Val Gly Ser
            35                  40                  45

Pro Val Trp Phe Tyr Gly Gly Ile Ile Tyr Phe Tyr Arg Lys Trp Lys
    50                  55                  60

Leu Tyr Arg Ser Lys Ala Ala Ala Thr Phe Ala Ala Arg His Glu Ser
65                  70                  75                  80

Gly Gly Gly Gly Ala Ser Ser Thr Val Arg Cys Arg Gly Thr Arg Gln
                85                  90                  95

Arg Thr Ser Ser Asp Asp Gly Asn Tyr Thr Ser Ser Thr Gly Glu Ser
                100                 105                 110

Ser Gln Glu Met Asn Glu Gln Glu Thr Gln Thr Gln Ser His Arg Gln
        115                 120                 125

Gln Thr Glu Gln Tyr Asn Asn Tyr Lys Arg Leu Ala Thr Arg Tyr Gly
    130                 135                 140

Val Ala Lys Ala Ala Ile Ile Lys Ile Ser Ile Trp Gly Pro His Arg
145                 150                 155                 160

Asp Lys Arg Val Gly Glu Trp Leu Gly Val Lys Lys Trp Arg Leu Trp
                165                 170                 175

Asp Ala Trp Leu Asn Tyr Val Gly Phe Thr Val Leu Lys Asp Asn Gly
            180                 185                 190

Asp Asp Asp His Thr Ile Ile Glu Thr Asn Pro His Ser Ala Ile Pro
            195                 200                 205

Asn Gln Glu Glu Phe Asp Ile His Thr Ser Pro Ser Ile Phe Ala Phe
    210                 215                 220

Val Pro His Gly Ile Phe Pro Phe Gly Leu Ala Phe Ser Cys Leu Pro
225                 230                 235                 240

Glu Arg Gly His Glu Gln Thr Trp Gly Leu Phe Arg Pro Val Val Ala
            245                 250                 255

Thr Ala Thr Lys Leu Phe Pro Leu Val Arg Thr Phe Ile Ser Trp Met
            260                 265                 270

Asn Gly Val Asp Ala Ser Asp Ser Ala Val Ser Arg Ala Leu Ala Pro
            275                 280                 285

Pro Tyr Thr Ser Asp His Pro Gly Arg Val Gly Val Ser Pro Gly Gly
    290                 295                 300

Ile Ala Glu Met Phe Glu Thr Tyr Pro Lys Pro Gly Phe His Pro Asn
305                 310                 315                 320

Asp Glu Ala Ala Leu Leu Lys Asp Arg Asn Gly Leu Phe Lys Leu Ala
                325                 330                 335

Met Lys His Lys Leu Pro Ile Val Pro Val Tyr Cys Phe Gly Ala Thr
            340                 345                 350

Lys Met Leu Arg Arg Val Gln Leu Pro Ala Phe Val Glu Thr Leu Ser
            355                 360                 365

Arg Met Leu Lys Ile Ser Leu Cys Leu Phe Phe Gly Lys Leu Gly Leu
    370                 375                 380

Pro Ile Pro Phe Arg Gln Arg Leu Met Tyr Val Met Gly Lys Thr Ile
385                 390                 395                 400

Phe Pro Pro Leu Pro Arg Asp Gly Val Asn Thr Ser Met Met Glu Gly
                405                 410                 415

Gly Glu Glu Phe Asp Gly Arg Val Gln Glu Met His Asp Ala Phe Cys

```
                420            425            430
Asn Glu Ile Thr Arg Ile Phe Glu Arg Asn Lys Asp His Tyr Gly Trp
         435                 440                445
Gly Asn Lys Asn Leu Arg Leu Val
     450             455

<210> SEQ ID NO 14
<211> LENGTH: 1432
<212> TYPE: DNA
<213> ORGANISM: Artificial
<220> FEATURE:
<223> OTHER INFORMATION: L400I mutant

<400> SEQUENCE: 14
```

| | | | | | |
|---|---|---|---|---|---|
| atgacaacaa | agaagcgtcc | actacccegt | catctgcacc | ttccacctgg | agtagaagta       60 |
| ctcgtctctc | caccacccta | cgaagtatgc | acgctcgtcg | acagattgtt | ggtctacgcc     120 |
| tcgtcgttga | ttgtcgttgg | atctcccgtt | tggttctacg | gaggcatcat | ttatttttac     180 |
| aggaagtgga | agaagtatcg | ttctcttgct | gctgctactg | aggctgcgag | acatgagagt     240 |
| ggtggcggtg | gtgcatcgtc | aacggttcgt | tgcagaggta | cacgtcaacg | tacatcgtct     300 |
| gatgacggca | actacacatc | gtcaactggc | gaaagctcgc | aagaaatgaa | cgaacaagag     360 |
| acacaaacac | aatcacatcg | acaacaaaca | gagcaataca | caactacaa  | acgattagca     420 |
| acaagatacg | gagtagcact | cgctgcaatc | attctcatat | ccatctgggg | gcctcatcgt     480 |
| gacaagcgtg | taggagaatg | gctcggtgtc | aagaagtgga | gattgtggga | tgcatggttg     540 |
| aactatgttg | gattcactgt | actaaaggac | aatggagatg | atgaccacac | aataatacaa     600 |
| acgaatccac | actcagcaat | acccaatcaa | gaagagtttg | acatacacac | atctccatca     660 |
| atcttcgcat | tcgtaccccca | cggcatcttt | cctttcggac | tcgccttttc | atgtctaccc     720 |
| gaacgaggac | acgaacaaac | atggggtctc | ttccgaccag | tcgttgcaac | agccaccaaa     780 |
| ctctttccgc | tggtacgaac | cttcatttct | tggatgaacg | gagtggatgc | ttcgcgttcg     840 |
| gcggtgtctc | gtgctcttgc | tcctccgtat | accagtgatc | atccgggaag | agtgggagtt     900 |
| tcgcccggtg | gtattgccga | gatgtttgag | acgtatccaa | agccggggtt | tcatcctaat     960 |
| gacgaggcag | cattgttaaa | agatcggaat | ggattgttca | agcttgcgat | gaaacacaag    1020 |
| ctgccgattg | ttccggtgta | ctgctttgga | gctacaaaga | tgttgagacg | agtgcaatta    1080 |
| cctgcgtttg | tggagacgtt | gagcagaatg | ctcaagatca | gtctttgttt | attctttgga    1140 |
| aagcttgggt | tgcctattcc | tttccgacag | cggctgatgt | atgtcatggg | caagacgatc    1200 |
| tttcctcctc | tgccgagaga | tggcgtgaac | acttctatga | tggaaggagg | agaagaattt    1260 |
| gatgaacgag | tgcaagagat | gcatgatgca | ttctgcaatg | agataactcg | catcttcgag    1320 |
| cgaaacaaag | accactacgg | ttggggtaac | aaaaacttga | gactcgtatg | agagtgtgag    1380 |
| tgatattcat | atgcaactct | taacttaaag | ccacagacca | cacaggcaca | aa             1432 |

```
<210> SEQ ID NO 15
<211> LENGTH: 124
<212> TYPE: PRT
<213> ORGANISM: Artificial
<220> FEATURE:
<223> OTHER INFORMATION: Catalytic domain

<400> SEQUENCE: 15

Ile Phe Pro Phe Gly Leu Ala Phe Ser Cys Leu Pro Glu Arg Gly His
1               5                   10                  15

Glu Gln Thr Trp Gly Leu Phe Arg Pro Val Val Ala Thr Ala Thr Lys
```

```
                20                  25                  30
Leu Phe Pro Leu Val Arg Thr Phe Ile Ser Trp Met Asn Gly Val Asp
            35                  40                  45

Ala Ser Asp Ser Ala Val Ser Arg Ala Leu Ala Pro Pro Tyr Thr Ser
        50                  55                  60

Asp His Pro Gly Arg Val Gly Val Ser Pro Gly Ile Ala Glu Met
65                  70                  75                  80

Phe Glu Thr Tyr Pro Lys Pro Gly Phe His Pro Asn Asp Glu Ala Ala
                85                  90                  95

Leu Leu Lys Asp Arg Asn Gly Leu Phe Lys Leu Ala Met Lys His Lys
            100                 105                 110

Leu Pro Ile Val Pro Val Tyr Cys Phe Gly Ala Thr
            115                 120

<210> SEQ ID NO 16
<211> LENGTH: 372
<212> TYPE: DNA
<213> ORGANISM: Artificial
<220> FEATURE:
<223> OTHER INFORMATION: Catalytic domain

<400> SEQUENCE: 16
atctttcctt tcggactcgc cttttcatgt ctacccgaac gaggacacga acaaacatgg      60
ggtctcttcc gaccagtcgt tgcaacagcc accaaactct ttccgctggt acgaaccttc    120
atttcttgga tgaacggagt ggatgcttcg cgttcggcgg tgtctcgtgc tcttgctcct    180
ccgtatacca gtgatcatcc gggaagagtg ggagtttcgc ccggtggtat tgccgagatg    240
tttgagacgt atccaaagcc ggggtttcat cctaatgacg aggcagcatt gttaaaagat    300
cggaatggat tgttcaagct tgcgatgaaa cacaagctgc cgattgttcc ggtgtactgc    360
tttggagcta ca                                                        372

<210> SEQ ID NO 17
<211> LENGTH: 124
<212> TYPE: PRT
<213> ORGANISM: Artificial
<220> FEATURE:
<223> OTHER INFORMATION: V298I mutant catalytic domain

<400> SEQUENCE: 17

Ile Phe Pro Phe Gly Leu Ala Phe Ser Cys Leu Pro Glu Arg Gly His
1               5                   10                  15

Glu Gln Thr Trp Gly Leu Phe Arg Pro Val Val Ala Thr Ala Thr Lys
            20                  25                  30

Leu Phe Pro Leu Val Arg Thr Phe Ile Ser Trp Met Asn Gly Val Asp
            35                  40                  45

Ala Ser Asp Ser Ala Val Ser Arg Ala Leu Ala Pro Pro Tyr Thr Ser
        50                  55                  60

Asp His Pro Gly Arg Ile Gly Val Ser Pro Gly Ile Ala Glu Met
65                  70                  75                  80

Phe Glu Thr Tyr Pro Lys Pro Gly Phe His Pro Asn Asp Glu Ala Ala
                85                  90                  95

Leu Leu Lys Asp Arg Asn Gly Leu Phe Lys Leu Ala Met Lys His Lys
            100                 105                 110

Leu Pro Ile Val Pro Val Tyr Cys Phe Gly Ala Thr
            115                 120

<210> SEQ ID NO 18
```

```
<211> LENGTH: 372
<212> TYPE: DNA
<213> ORGANISM: Artificial
<220> FEATURE:
<223> OTHER INFORMATION: V298I mutant catalytic domain

<400> SEQUENCE: 18
atctttcctt tcggactcgc cttttcatgt ctacccgaac gaggacacga acaaacatgg      60
ggtctcttcc gaccagtcgt tgcaacagcc accaaactct ttccgctggt acgaaccttc     120
atttcttgga tgaacggagt ggatgcttcg cgttcggcgg tgtctcgtgc tcttgctcct     180
ccgtatacca gtgatcatcc gggaagaatc ggagtttcgc ccgtggtat tgccgagatg      240 tttgagacgt atccaaagcc ggggtttcat cctaatgacg aggcagcatt gttaaaagat     300
cggaatggat tgttcaagct tgcgatgaaa cacaagctgc cgattgttcc ggtgtactgc     360
tttggagcta ca                                                        372

<210> SEQ ID NO 19
<211> LENGTH: 124
<212> TYPE: PRT
<213> ORGANISM: Artificial
<220> FEATURE:
<223> OTHER INFORMATION: I343L mutant catalytic domain

<400> SEQUENCE: 19

Ile Phe Pro Phe Gly Leu Ala Phe Ser Cys Leu Pro Glu Arg Gly His
 1               5                  10                  15

Glu Gln Thr Trp Gly Leu Phe Arg Pro Val Val Ala Thr Ala Thr Lys
             20                  25                  30

Leu Phe Pro Leu Val Arg Thr Phe Ile Ser Trp Met Asn Gly Val Asp
         35                  40                  45

Ala Ser Asp Ser Ala Val Ser Arg Ala Leu Ala Pro Pro Tyr Thr Ser
     50                  55                  60

Asp His Pro Gly Arg Val Gly Val Ser Pro Gly Ile Ala Glu Met
 65                  70                  75                  80

Phe Glu Thr Tyr Pro Lys Pro Gly Phe His Pro Asn Asp Glu Ala Ala
                 85                  90                  95

Leu Leu Lys Asp Arg Asn Gly Leu Phe Lys Leu Ala Met Lys His Lys
            100                 105                 110

Leu Pro Leu Val Pro Val Tyr Cys Phe Gly Ala Thr
        115                 120

<210> SEQ ID NO 20
<211> LENGTH: 372
<212> TYPE: DNA
<213> ORGANISM: Artificial
<220> FEATURE:
<223> OTHER INFORMATION: I343L mutant catalytic domain

<400> SEQUENCE: 20
atctttcctt tcggactcgc cttttcatgt ctacccgaac gaggacacga acaaacatgg      60
ggtctcttcc gaccagtcgt tgcaacagcc accaaactct ttccgctggt acgaaccttc     120
atttcttgga tgaacggagt ggatgcttcg cgttcggcgg tgtctcgtgc tcttgctcct     180
ccgtatacca gtgatcatcc gggaagagtg gagtttcgc ccgtggtat tgccgagatg       240 tttgagacgt atccaaagcc ggggtttcat cctaatgacg aggcagcatt gttaaaagat     300
cggaatggat tgttcaagct tgcgatgaaa cacaagctgc cgcttgttcc ggtgtactgc     360
tttggagcta ca                                                        372
```

```
<210> SEQ ID NO 21
<211> LENGTH: 1432
<212> TYPE: DNA
<213> ORGANISM: Artificial
<220> FEATURE:
<223> OTHER INFORMATION: 80% nucleotide sequence homology to TpDGA2

<400> SEQUENCE: 21
atgactacta aaaacgacc tcttccgcga catctccacc tacctccagg tgttgaagtt       60
ctggtgtcac ctcctccgta cgaagtttgc accctggtgg acagattgtt ggtgtacgcg     120
tcctccttga tagtggtagg ttcaccggta tggttctacg gtgggatcat atatttttac     180
aggaaatgga aaaaatatcg atcactagca gcagcaacag aggcagccag acatgagagt     240 ggaggggag gagcttcctc taccgtacga tgcagaggaa ctcgacagcg aacttcctca      300
gatgacggga actacacttc ctctacaggg aaagctccc aggaaatgaa cgaacaggag      360
actcagactc agtctcatcg tcagcagact gagcagtaca caactacaa gcgtttagct      420 actagatacg gtgttgctct ggcagctatc atactgattt cgatctgggg cccacatcga     480
gacaaacgag ttggtgaatg ctgggagtg aaaaaatgga gattgtggga tgcttggttg      540
aactatgtag gtttcacagt tcttaaagac aatggtgatg atgaccacac tattattcag     600
accaatcctc actctgctat tccgaatcag aagagtttg acattcacac ttcaccttct      660
atcttcgctt tcgttccgca cgggatcttt ccattcggtc tggcgttttc ttgtcttccg     720
gaacgtggtc acgaacagac ttggggactg ttccgtcctg tggtagctac tgcgacgaag     780
ctgtttcccc tcgttcgtac gttcatatca tggatgaacg gtgtcgatgc atcccgatcc     840
gccgtctcac gagcactagc accaccctat acgagtgatc atcccggtag agtcggtgta     900
tccccgggag aatagcgga gatgtttgag acctatccta aacccggctt tcatccaaat      960
gacgaggctg ctttgttaaa ggatcgcaat ggtttgttca aactagccat gaagcacaaa    1020
ctccccatag tacccgtcta ctgctttggt gcaactaaaa tgttgagacg tgtccagtta    1080
ccagcctttg tcgagacctt gagcagaatg ctgaaaatca gtctatgttt attcttggt     1140 aaactaggct tgccaatacc attccgtcaa cgcctcatgt atgtgatggg aaaaccttg     1200 tttccaccac tccccagaga tggggtcaac acatcaatga tggaaggtgg tgaagaattt    1260
gatgaacgtg tccaggagat gcatgatgct ttctgcaatg agattacacg gatcttcgag    1320
cgtaacaagg accactacgg atggggaaac aagaacttga gactggtttg agagtgtgag    1380
tgatattctt atgctacact aaacttaaaa cctcaaacga ctcaagctca ga            1432

<210> SEQ ID NO 22
<211> LENGTH: 1432
<212> TYPE: DNA
<213> ORGANISM: Artificial
<220> FEATURE:
<223> OTHER INFORMATION: 85% nucleotide sequence homology to TpDGA2

<400> SEQUENCE: 22
atgacaacta aaaacgacc tcttccgcgt catctccacc tacctcctgg tgttgaagtt       60
ctcgtgtcac ctccaccgta cgaagtttgc accctcgtgg acagattgtt ggtgtacgcg     120
tcgtccttga tagtggttgg ttcaccggtt tggttctacg gtgggatcat atatttttac     180
aggaaatgga aaaaatatcg atctctagca gcagctacag aggcagccag acatgagagt     240
ggtgggggag gagcatcctc taccgttcga tgcagaggaa ctcgtcagcg aacttcgtca     300
gatgacggga actacacttc gtctacaggg aaagctcgc aggaaatgaa cgaacaggag      360
```

| | |
|---|---|
| acacagactc agtctcatcg acagcagaca gagcagtaca caactacaa gcgtttagct | 420 |
| acaagatacg gtgttgctct cgcagctatc atactcattt cgatctgggg ccctcatcga | 480 |
| gacaaacgag taggtgaatg gctgggagtc aaaaaatgga gattgtggga tgcttggttg | 540 |
| aactatgttg gtttcacagt tctaaaagac aatggtgatg atgaccacac tataattcag | 600 |
| accaatccac actctgctat tcccaatcag gaagagtttg acattcacac ttctccttct | 660 |
| atcttcgctt tcgtaccgca cgggatcttt ccattcggac tggcgttttc ttgtctaccg | 720 |
| gaacgtggac acgaacagac ttggggactg ttccgacctg tggtagcaac tgcgaccaag | 780 |
| ctgtttcccc tcgtacgtac gttcatatct tggatgaacg tgtcgatgc atcgcgatcc | 840 |
| gccgtgtcac gagcacttgc accaccctat accagtgatc atcccggtag agtcggagta | 900 |
| tccccgggtg aatagcgga gatgtttgag acgtatccta aacccgggtt tcatccaaat | 960 |
| gacgaggctg ctttgttaaa cgatcgcaat ggtttgttca aacttgccat gaagcacaaa | 1020 |
| ctgcccatag taccggtcta ctgctttggt gcaacaaaaa tgttgagacg tgtgcagtta | 1080 |
| ccagcctttg tcgagacgtt gagcagaatg ctgaaaatca gtctatgttt attctttgga | 1140 |
| aaactaggct tgcctatacc attccgacaa cgcctcatgt atgtgatggg caaaaccttg | 1200 |
| tttccaccgc tccccagaga tggggtgaac acatcaatga tggaaggtgg agaagaattt | 1260 |
| gatgaacgtg tccaggagat gcatgatgca ttctgcaatg agattacacg gatcttcgag | 1320 |
| cgaaacaagg accactacgg atgggggtaac aagaacttga gactggtttg agagtgtgag | 1380 |
| tgatattctt atgcaacact aaacttaaaa ccacaaacga cacaagctca ga | 1432 |

<210> SEQ ID NO 23
<211> LENGTH: 1432
<212> TYPE: DNA
<213> ORGANISM: Artificial
<220> FEATURE:
<223> OTHER INFORMATION: 90% nucleotide sequence homology to TpDGA2

<400> SEQUENCE: 23

| | |
|---|---|
| atgacaacta aaaaacgtcc tcttccgcgt catctgcacc tacctcctgg agtagaagtt | 60 |
| ctcgtgtcac caccaccgta cgaagtttgc accctcgtcg acagattgtt ggtgtacgcg | 120 |
| tcgtcgttga ttgtggttgg ttcacccgtt tggttctacg gtggcatcat atattttttac | 180 |
| aggaaatgga aaaaatatcg atctcttgct gcagctacag aggcagcgag acatgagagt | 240 |
| ggtgggggag gagcatcgtc taccgttcgt tgcagaggta ctcgtcagcg aacatcgtca | 300 |
| gatgacggga actacacttc gtcaactggc gaaagctcgc aggaaatgaa cgaacaggag | 360 |
| acacagactc agtcacatcg acagcagaca gagcagtaca caactacaa gcgattagct | 420 |
| acaagatacg gtgtagcact cgcagctatc attctcattt cgatctgggg ccctcatcgt | 480 |
| gacaaacgag taggtgaatg gctcggtgtc aaaaaatgga gattgtggga tgcatggttg | 540 |
| aactatgttg gtttcacagt tctaaaagac aatggagatg atgaccacac tataattcag | 600 |
| acgaatccac actcagctat acccaatcag gaagagtttg acattcacac ttctccatct | 660 |
| atcttcgctt tcgtaccgca cggcatcttt ccattcggac tcgcgttttc atgtctaccg | 720 |
| gaacgtggac acgaacagac atggggactg ttccgacctg tcgtagcaac agcgaccaag | 780 |
| ctcttccccc tcgtacgaac gttcatatct tggatgaacg tgtggatgc atcgcgttcc | 840 |
| gcggtgtcac gagcacttgc tccaccctat accagtgatc atcccggaag agtcggagtt | 900 |
| tccccggtg aatagcgga gatgtttgag acgtatccaa aacccgggtt tcatccaaat | 960 |
| gacgaggcag ctttgttaaa cgatcggaat ggtttgttca aacttgcgat gaagcacaaa | 1020 |

```
ctgccgatag taccggtcta ctgctttgga gctacaaaaa tgttgagacg tgtgcagtta    1080
cctgcctttg tcgagacgtt gagcagaatg ctcaaaatca gtctatgttt attctttgga    1140
aaacttggct tgcctattcc attccgacaa cggctcatgt atgtgatggg caaaacgttg    1200
tttccaccgc tcccgagaga tggggtgaac acttcaatga tggaaggagg agaagaattt    1260
gatgaacgtg tccaggagat gcatgatgca ttctgcaatg agataacacg gatcttcgag    1320
cgaaacaagg accactacgg ttggggtaac aagaacttga gactcgtttg agagtgtgag    1380
tgatattcat atgcaacact taacttaaaa ccacaaacca cacaagcaca ga            1432
```

<210> SEQ ID NO 24
<211> LENGTH: 1432
<212> TYPE: DNA
<213> ORGANISM: Artificial
<220> FEATURE:
<223> OTHER INFORMATION: 95% nucleotide sequence homology to TpDGA2

<400> SEQUENCE: 24

```
atgacaacaa aaaacgtcc actaccgcgt catctgcacc ttccacctgg tgtagaagta      60
ctcgtgtctc caccaccta cgaagtttgc acgctcgtcg acagattgtt ggtctacgcc     120
tcgtccttga ttgtcgttgg atctcccgtt tggttctacg gaggcatcat atattttac    180 aggaaatgga aaaatatcg ttctcttgca gcagcaacag aggcagcgag acatgagagt    240
ggtgggggtg gtgcttcgtc tacggttcgt tgcagaggta cacgtcagcg aacatcgtct    300
gatgacggca actacacatc gtcaactggc gaaagctcgc aggaaatgaa cgaacaggag    360
acacagacac agtcacatcg acagcagaca gagcagtaca caactacaa gcgattagca    420 acaagatacg gagtagcact cgcagcaatc attctcatat ccatctgggg ccctcatcgt    480
gacaaacgtg taggagaatg gctcggtgtc aaaaaatgga gattgtggga tgcatggttg    540
aactatgttg gattcactgt actaaaagac aatggagatg atgaccacac aataatacag    600
acgaatccac actcagctat acccaatcag gaagagttg acatacacac atctccatca    660
atcttcgcat tcgtaccgca cggcatcttt cctttcggac tggcctttc atgtctaccg    720 gaacgtggac acgaacagac atggggtctc ttccgaccag tcgtagcaac agccaccaag    780
ctctttccgc tggtacgaac gttcattct tggatgaacg tgtggatgc atcgcgttcc    840 gcggtgtctc gtgcacttgc acctccctat accagtgatc atccgggaag agtgggagta    900
tcgcccggtg gtatagccga gatgtttgag acgtatccaa accggggtt tcatcctaat    960 gacgaggcag ctttgttaaa cgatcggaat ggattgttca aacttgcgat gaaccacaaa    1020
ctgccgattg ttccggtcta ctgctttgga gcaacaaaaa tgttgagacg agtgcagtta    1080
cctgcgtttg tggagacgtt gagcagaatg ctcaaaatca gtctttgttt attctttgga    1140 aaacttggt tgcctattcc tttccgacaa cggctgatgt atgtcatggg caaaacgttg    1200
tttcctccgc tgccgagaga tggggtgaac acttcaatga tggaaggagg agaagaattt    1260
gatgaacgag tgcaggagat gcatgatgca ttctgcaatg agataactcg catcttcgag    1320
cgaaacaagg accactacgg ttggggtaac aagaacttga gactcgtatg agagtgtgag    1380
tgatattcat atgcaactct taacttaaaa ccacaaacca cacaagcaca ga            1432
```

<210> SEQ ID NO 25
<211> LENGTH: 309
<212> TYPE: PRT
<213> ORGANISM: T. pseudonana

<400> SEQUENCE: 25

```
Leu Ala Val Thr Leu Trp Leu Gly Trp Asn Gly Ile Val Val Cys Ile
1               5                   10                  15

Ala Val Tyr Leu Leu Phe Ile Ala Asn Asn Ile Glu Arg Met Val Ile
            20                  25                  30

Ile Gly Leu Ala Thr Met Ser Leu Ile Leu Pro Ala His Phe Pro Gly
        35                  40                  45

Ala Leu Gly Tyr Lys Ile Gly Asp Trp Ile Met Arg Gln Ala Glu Lys
    50                  55                  60

Tyr Phe Gly Leu Lys Thr Val Ile Glu Asp Glu Asp Leu Ile Arg
65              70                  75                  80

His Ala Asn Glu Asn Lys Ala Val Ile Phe Ala Phe Asn Pro His Asp
                85                  90                  95

Met Leu Pro Tyr Ala Val Phe Ala Phe Ala Pro Thr Leu Lys Arg Leu
            100                 105                 110

Pro Gly Lys Ile Gly Lys Asp Gly Thr Cys Leu Met Ser Ser Ala Ile
        115                 120                 125

Phe Asn Ile Pro Phe Leu Arg Gln Val Tyr Thr Trp Val Asn Ser Leu
    130                 135                 140

Pro Val Asp Lys Lys Thr Phe Leu Gly Arg Leu Lys Arg Gly Gln Ser
145                 150                 155                 160

Phe Ala Phe Val Pro Gly Gly Val Gln Glu Val Ile Met Leu Asp Pro
                165                 170                 175

Asn Gln Pro Lys Asp Val Val Leu Tyr Leu Lys Asn Arg Lys Gly Phe
            180                 185                 190

Val Lys Leu Ala Leu Ala Thr Gly Ser Pro Ile Val Pro Val Phe Gly
        195                 200                 205

Phe His Leu Asp Gly Ser Tyr Gly Tyr Trp Leu Pro Lys Gly Lys Leu
    210                 215                 220

Val Glu Arg Leu Ser Arg Thr Leu Gly Phe Leu Pro Leu Leu Phe Trp
225                 230                 235                 240

Gly Arg Trp Met Ile Pro Phe Gly Ile Pro His Pro Lys Lys Ile His
                245                 250                 255

Val Val Val Gly Ser Ala Ile Asp Val Pro Asn Glu Gly Glu Asp Val
            260                 265                 270

Ser Gln Glu Ser Ile Glu Lys Tyr His Ala Ile Phe Leu Lys Glu Leu
        275                 280                 285

Glu Ala Leu Phe Glu Arg His Lys Glu Glu Ala Gly Tyr Gly His Arg
    290                 295                 300

Gln Leu Lys Ile Val
305

<210> SEQ ID NO 26
<211> LENGTH: 930
<212> TYPE: DNA
<213> ORGANISM: T. pseudonana

<400> SEQUENCE: 26
ctggcagtca cattgtggtt ggggtggaat gggatcgtgg tgtgtatcgc agtctacctc      60
ttgttcattg ccaacaatat tgaacgaatg gtgattattg gattggcaac gatgtcgttg     120
atactgcctg ctcactttcc aggagctttg ggctacaaga ttggggattg gattatgcgt     180
caggcagaga agtactttgg attaaagacg gtgattgaag acgaagagga tttgattcgg     240
catgccaatg agaacaaagc agtgatattt gccttcaatc cacatgatat gttgccgtat     300
gcagtatttg cattcgctcc tacattgaag agactaccgg gtaagatcgg gaaggatgga     360
```

```
acgtgcctca tgtcatcggc aatcttcaac attccttttt tgagacaagt gtatacgtgg     420
gtgaacagcc ttccagtaga caagaaaaca tttctgggga ggctgaagag agggcaaagc     480
tttgcttttg ttcctggggg agtgcaagag gtcattatgc ttgatccgaa ccagccaaaa     540
gatgtggtgc tatatctcaa gaaccgcaaa ggattcgtga agctggcgtt ggcgacaggc     600
tcgcccatcg tgcccgtgtt tggctttcat ctggatggaa gctatggcta ttggctgccg     660
aaagggaaac tggtcgagag actttcacga acattgggct tcttcctct tctcttttgg      720 gggcgttgga tgataccttt cggcatacca caccccaaaa agattcacgt tgtcgttgga     780
tcagcaatag atgtaccgaa cgagggagaa gatgtctcac aagagtcaat tgaaaagtac     840
catgccatct ttctgaagga gcttgaagca ttgtttgaga ggcacaagga agaagcggga     900
tacggacatc ggcaattgaa gattgtctaa                                      930

<210> SEQ ID NO 27
<211> LENGTH: 158
<212> TYPE: PRT
<213> ORGANISM: T. pseudonana

<400> SEQUENCE: 27

Met Glu Asp Tyr Leu Lys Asn Gly Glu Asp Val Ala Leu Pro Pro Gly
1               5                   10                  15

Gly Phe Glu Glu Ala Thr Leu Thr Cys Thr Thr Gln Asp Arg Val Phe
            20                  25                  30

Ile Lys Lys Arg Tyr Gly Phe Val Arg Leu Cys Leu Lys Tyr Gly Val
        35                  40                  45

Ala Ile Arg Pro Val Tyr Val Phe Gly Glu Gly Arg Leu Phe Gly Asn
    50                  55                  60

Val Gln Gly Met Trp Lys Thr Arg Leu Ala Leu Asn Arg Trp Gly Ile
65                  70                  75                  80

Pro Thr Ile Leu Val Trp Gly Ser Trp Phe Phe Pro Leu Leu Pro Lys
                85                  90                  95

Lys Gly Val Asn Leu His Ile Val Gly Lys Pro Leu Ile Val Pro
            100                 105                 110

Lys Ile Asp Asn Pro Thr Lys Glu Glu Val Ile Ala Trp His Glu Lys
        115                 120                 125

Tyr Ile Thr Glu Leu Lys Arg Ile Tyr Glu Glu Tyr Lys Glu Val Ala
    130                 135                 140

Tyr Gly Asn Glu Asp Gly Lys Val Ala Lys Leu Glu Val Trp
145                 150                 155

<210> SEQ ID NO 28
<211> LENGTH: 477
<212> TYPE: DNA
<213> ORGANISM: T. pseudonana

<400> SEQUENCE: 28
atggaagact atctgaaaaa tggagaggat gtggcacttc ctcctggggg atttgaggag      60
gctaccctga cttgtacaac gcaggatagg gtgtttatca agaagcggta tggctttgtg     120
aggctgtgtt tgaagtatgg agtggcgata cgaccagtct atgtgtttgg agagggaaga     180
ttgtttggca acgtacaagg aatgtggaag acaagacttg ccttgaatcg atggggcatt     240
ccgactatat tggtatgggg tagttggttc tttcccttgc ttccgaagaa gggtgtcaac     300
ctacatattg ttgttggaaa gcctttgatt gtgccaaaga ttgacaatcc aacaaaggaa     360
gaggttattg cgtggcatga aaagtatatt accgagttga gaggattta tgaagagtac     420
```

```
aaggaggttg cgtacggtaa cgaggacgga aaggttgcaa agcttgaggt ttggtga         477
```

```
<210> SEQ ID NO 29
<211> LENGTH: 376
<212> TYPE: PRT
<213> ORGANISM: T. pseudonana

<400> SEQUENCE: 29
```

| | | | | | | | | | | | | | | | |
|---|---|---|---|---|---|---|---|---|---|---|---|---|---|---|---|
| Met | Lys | Tyr | Arg | Lys | Leu | Asn | Leu | Ala | Thr | Leu | Pro | Asp | Glu | Leu | Phe |
| 1 | | | | 5 | | | | | 10 | | | | | 15 | |
| Thr | Lys | Gln | Thr | Asp | Val | Lys | Glu | Trp | Met | Ala | Leu | Thr | Thr | Thr | Ser |
| | | | 20 | | | | | 25 | | | | | 30 | | |
| Ala | Glu | Gly | Gly | Phe | Pro | Ser | Ser | Leu | Asn | Lys | Val | Leu | Pro | Val | |
| | | 35 | | | | | 40 | | | | | 45 | | | |
| Lys | Arg | Asp | Ile | Glu | Ile | Glu | Arg | Ile | Ile | Gly | Thr | Ser | Tyr | Tyr | Met |
| 50 | | | | | 55 | | | | | 60 | | | | | |
| Ile | Gly | Asn | Thr | Val | Pro | Phe | Ala | Val | Pro | Leu | Leu | Leu | Ala | Ala | Ser |
| 65 | | | | | 70 | | | | | 75 | | | | | 80 |
| Tyr | Phe | Ser | Ala | Val | Gly | Ala | Leu | Ile | Phe | Lys | Val | Tyr | Met | Val | Tyr |
| | | | | 85 | | | | | 90 | | | | | 95 | |
| Phe | Thr | Thr | Leu | Phe | Val | Val | Phe | Thr | Tyr | Tyr | Phe | Tyr | Pro | Lys | Tyr |
| | | | 100 | | | | | 105 | | | | | 110 | | |
| Met | Lys | Arg | Tyr | Asn | Arg | Pro | Lys | Ser | Met | Ser | Lys | Thr | Asp | Ile | Lys |
| | | 115 | | | | | 120 | | | | | 125 | | | |
| Asp | Asn | Gln | Tyr | Leu | Tyr | Thr | Glu | Arg | His | Thr | Gln | Lys | Tyr | Leu | Ser |
| 130 | | | | | 135 | | | | | 140 | | | | | |
| Met | Gln | Phe | Val | Trp | Pro | Glu | Ser | Ile | Gln | Arg | Pro | Ala | Leu | Asn | Asp |
| 145 | | | | | 150 | | | | | 155 | | | | | 160 |
| Gln | Pro | Val | Ile | Phe | Ala | Ala | Ile | Pro | His | Gly | Leu | Ser | Pro | Leu | Gly |
| | | | | 165 | | | | | 170 | | | | | 175 | |
| Ile | Thr | Ala | Tyr | Pro | Met | Trp | Ser | Lys | Leu | Phe | Asn | Asp | Lys | Leu | Cys |
| | | | 180 | | | | | 185 | | | | | 190 | | |
| His | Trp | Thr | Cys | Ala | Pro | Val | Val | Leu | Lys | Leu | Pro | Leu | Ile | Ser | Ser |
| | | 195 | | | | | 200 | | | | | 205 | | | |
| Phe | Met | Lys | Ala | Ile | Gly | Tyr | Ile | Pro | Ala | Lys | Ala | Lys | Asn | Ile | Thr |
| 210 | | | | | 215 | | | | | 220 | | | | | |
| Asp | Thr | Leu | Ile | Lys | Lys | Glu | Glu | Asn | Val | Gly | Ile | Ile | Leu | Asp | Gly |
| 225 | | | | | 230 | | | | | 235 | | | | | 240 |
| Ile | Ala | Gly | Met | Phe | Gln | Ala | His | Asp | Glu | Val | Ala | His | Val | Lys | Arg |
| | | | | 245 | | | | | 250 | | | | | 255 | |
| Arg | Lys | Gly | Ile | Ile | Lys | Ile | Ala | Leu | Arg | Ala | Gly | Ala | Ala | Val | Val |
| | | | 260 | | | | | 265 | | | | | 270 | | |
| Pro | Val | Tyr | Gly | Phe | Gly | His | Thr | Ser | Leu | Trp | Lys | Ile | Val | Val | Asp |
| | | 275 | | | | | 280 | | | | | 285 | | | |
| Pro | Phe | Gly | Phe | Leu | Glu | Trp | Leu | Ser | Thr | Lys | Ser | Asp | Val | Ser | Val |
| 290 | | | | | 295 | | | | | 300 | | | | | |
| Thr | Pro | Phe | Phe | Gly | Arg | Phe | Asn | Trp | Phe | Leu | Gly | Pro | Pro | Lys | Arg |
| 305 | | | | | 310 | | | | | 315 | | | | | 320 |
| Val | Ala | Val | Cys | Val | Cys | Met | Gly | Asp | Ala | Ile | Lys | Cys | Pro | Lys | Ile |
| | | | | 325 | | | | | 330 | | | | | 335 | |
| Glu | Glu | Pro | Thr | Gln | Gln | Asp | Ile | Asp | Lys | Tyr | His | Gly | Leu | Leu | Leu |
| | | | 340 | | | | | 345 | | | | | 350 | | |
| Lys | Gly | Tyr | Asp | Gln | Leu | Phe | Glu | Gln | His | Lys | Val | Ala | Tyr | Gly | Trp |
| | | 355 | | | | | 360 | | | | | 365 | | | |
| Gly | Asp | Lys | Lys | Leu | Gln | Phe | Val | | | | | | | | |

```
                 370                 375
```

<210> SEQ ID NO 30
<211> LENGTH: 1131
<212> TYPE: DNA
<213> ORGANISM: T. pseudonana

<400> SEQUENCE: 30

| | | | | |
|---|---|---|---|---|
| atgaagtatc | gcaaactcaa | cctagccacc | ctaccagacg | aactcttcac caaacagaca | 60 |
| gatgtgaaag | agtggatggc | gcttaccaca | acgtcagcgg | aaggaggctt tccaccatcg | 120 |
| tcattaaaca | aagtgttgcc | tgtgaagaga | gacatcgaga | ttaacgtat catcggcact | 180 |
| tcctactata | tgattgggaa | tacggttcca | tttgcagttc | cgcttctgtt ggctgcatcg | 240 |
| tactttagtg | cagttggtgc | tctgattttc | aaggtgtaca | tggtgtactt taccacactg | 300 |
| ttcgtagtgt | tcacgtatta | tttctaccca | aagtacatga | acgatacaa tcgtccgaag | 360 |
| tccatgtcta | agactgacat | caaggacaac | caatatctgt | acacagaacg tcacacccaa | 420 |
| aagtatctct | ccatgcaatt | cgtgtggcca | gaatcaatcc | aaagaccagc tcttaacgat | 480 |
| caaccagtaa | tctttgcagc | cattccacat | ggattaagcc | cgttaggaat cacggcatat | 540 |
| ccaatgtggt | caaagttgtt | caatgataaa | ctttgccatt | ggacttgtgc accagtggtg | 600 |
| ttgaagttgc | ctttgatatc | ttcgtttatg | aaggctattg | gttacattcc agcgaaagca | 660 |
| aagaatatca | cggacacact | gatcaagaag | gaagagaatg | ttggtatcat tcttgatgga | 720 |
| atcgctggaa | tgtttcaggc | tcatgatgaa | gtggcacacg | tgaagagaag gaagggatt | 780 |
| atcaagattg | cattgagggc | cggagccgca | gttgtacctg | tgtacggttt cggtcatact | 840 |
| tcgttgtgga | aaatcgtcgt | tgatcccttt | ggattcttgg | aatggctgag tacaaaatcg | 900 |
| gatgtctctg | tcacacccttt | cttcgggagg | ttcaactggt | ttttgggtcc tccgaaacga | 960 |
| gttgctgtct | gtgtctgcat | gggagacgca | ataaagtgtc | ctaagatcga ggaaccgacg | 1020 |
| caacaagaca | ttgataagta | tcatggactc | ttattgaaag | gatacgatca actatttgaa | 1080 |
| cagcacaaag | tagcatacgg | atggggtgat | aagaaactgc | agtttgttta a | 1131 |

<210> SEQ ID NO 31
<211> LENGTH: 346
<212> TYPE: PRT
<213> ORGANISM: Chlamydomonas reinhardtii

<400> SEQUENCE: 31

Met Ala Gly Gly Lys Ser Asn Gly Thr Gly Ala Ala Asp Ala His Val
1               5                   10                  15

Arg Thr Ser His Leu Thr Leu Lys Ala Gly Glu Asp Pro Pro Pro Asn
            20                  25                  30

Val Arg Ile Tyr Ser Asp Gly Ile Lys Pro Asp Ala Arg Gln Asn Leu
        35                  40                  45

Leu Val Gln Ile Leu Ala Gly Ile Thr Met Ser Ile Tyr Val Gly Phe
    50                  55                  60

Met Asn Tyr Phe Met Leu Leu Val Val Leu Ser Tyr Trp Ser Arg Ile
65                  70                  75                  80

Cys Arg Tyr Val Val Leu Ala Leu Leu Gly Thr Leu Ala Leu Pro Cys
                85                  90                  95

Lys Pro Val Leu Trp Pro Ala Phe Asn Lys Leu Trp Ile Phe Lys Thr
            100                 105                 110

Trp Arg His Tyr Phe His Tyr Ser Phe Leu Ile Glu Glu Pro Leu Asp
        115                 120                 125

```
Pro Asn Lys Arg Tyr Ile Phe Val Glu Phe Pro His Gly Ala Phe Pro
    130                 135                 140

Ile Gly Pro Ile Val Ala Gly Thr Leu Met Gln Thr Leu Phe Pro His
145                 150                 155                 160

Met Met Ile Tyr Ser Val Ala Ala Ser Val Val Phe Tyr Ile Pro Phe
                165                 170                 175

Trp Arg His Phe Ile Thr Trp Ile Gly Ser Val Pro Ala Thr Pro Gly
            180                 185                 190

Asn Phe Lys Arg Leu Leu Lys Lys Gly Ser Val Ala Val Val Val Gly
        195                 200                 205

Gly Ile Ala Glu Met Tyr Met Gly Asn Lys Lys Glu Arg Ile Lys
    210                 215                 220

Leu Val Gly Arg Arg Gly Phe Ala Arg Ile Ala Leu Glu Glu Gln Val
225                 230                 235                 240

Asp Gly Ile Val Cys Val Tyr Tyr Phe Gly Gln Ser Gln Val Leu Asp
                245                 250                 255

Phe Gly Pro Ser Trp Leu Ala Asp Phe Ser Arg Arg Met Arg Thr Ser
            260                 265                 270

Phe Gly Tyr Leu Thr Gly Trp Met Gly Leu Pro Val Pro Arg Pro Ile
        275                 280                 285

Pro Ile Tyr Met Val Asn Gly Lys Pro Ile Pro Val Pro Lys Val Ala
290                 295                 300

Arg Asp Ser Pro Glu Phe Asp Lys Glu Val Asp Lys Leu Leu Asp Ala
305                 310                 315                 320

Thr Ile Thr Glu Leu Gly Glu Met Tyr Asn Arg His Arg Gly Glu Tyr
                325                 330                 335

Gly Trp Gly Asp Arg Pro Leu Ser Ile Glu
            340                 345

<210> SEQ ID NO 32
<211> LENGTH: 1041
<212> TYPE: DNA
<213> ORGANISM: Chlamydomonas reinhardtii

<400> SEQUENCE: 32
atggcaggtg gaaagtcaaa cggcacgggc gcggcggacg cgcacgtgcg tacctcgcac      60
ttgaccctga aagctgggga ggacccgccc ccgaatgttc gcatctacag tgacggcatc     120
aagccggacg cgcggcagaa cctgcttgtt cagatcctgg ccggcatcac gatgtcgatt     180
tatgtaggct tcatgaacta tttcatgctg ctggtggtgc tctcctactg gagccgcatc     240
tgccgctatg tggtcctggc gctgctaggc acactggcgc tgccctgcaa gcccgtgctg     300
tggcctgcct tcaacaagct gtggatcttc aagacctggc gtcactactt ccactacagt     360
ttcctgattg aggagccgct tgaccccaac aagcgctaca tctttgtcga gttcccgcac     420
ggcgcgttcc ccattggtcc catcgtggcg ggcacgctca tgcagactct gttcccgcac     480
atgatgatct acagcgtggc cgcctccgtc gtgttctaca tccccttctg gcgccatttc     540
atcacgtgga tcggctcggt gcccgcaacg cccggcaact tcaagcggct gctgaagaag     600
ggcagtgtgg cggtggtggt gggcggcatt gccgagatgt acatgggcaa caagaagaag     660
gagcgcatta agctagtggg ccgccgcggc ttcgcacgca tcgcgctgga ggagcaggtg     720
gacggcattg tgtgcgtgta ctacttcggt cagagccaag tgctggactt cgggccctcc     780
tggctggcgg actttagccg ccgcatgcgc accagcttcg gctacctcac gggatggatg     840
gggctgccgg tgccgcggcc catccccatc tacatggtga atgggaagcc catcccggtg     900
```

```
cccaaggtgg ctcgtgactc gcccgagttc gacaaggagg tggataagct gcttgacgcc    960
accatcacgg agctgggcga gatgtacaac aggcacagag gcgagtacgg ctggggcgac   1020
cgcccgctgt ccatcgagta g                                              1041
```

<210> SEQ ID NO 33
<211> LENGTH: 413
<212> TYPE: PRT
<213> ORGANISM: Chlamydomonas reinhardtii

<400> SEQUENCE: 33

```
Met Thr Pro Arg Asp Pro Pro Val Pro Arg Pro Pro Gly Val Arg
 1               5                  10                  15

Gln Tyr Thr Asp Gly Arg Ser Ala Ser Tyr Val Leu Pro Leu Pro Tyr
                20                  25                  30

Arg Leu Leu Ala Gln Leu Thr Leu Gly Leu Tyr Val Gly Phe Pro Tyr
                35                  40                  45

Ile Leu Leu Gly Leu Leu Gly Thr Ala Ala Gly Ser Arg Ala Ala
 50                  55                  60

Ala Ala Ala Leu Ala Leu Thr Leu Gly Ser Leu Leu Val Pro Ala Pro
 65                  70                  75                  80

Pro His Ile Arg Gln Gly Met Leu Asp Ser Ala Leu Phe Arg Leu Trp
                85                  90                  95

Arg Ala Tyr Phe Asn Tyr Ser Tyr Ala Tyr Asp Gln Leu Pro Asp Phe
                100                 105                 110

Asn Arg Pro His Ile Phe Val Asn Ser Pro His Gly Ala Phe Pro Leu
                115                 120                 125

Ser Gln Ile Leu Cys Ile Ser Leu Ser Asn Ile Val Trp Pro Gly Phe
 130                 135                 140

Pro Val His Ser Leu Ala Ala Ser Val Leu Trp Tyr Ile Pro Leu Trp
 145                 150                 155                 160

Arg His Met Lys Ala Ala Leu Gly Ala Ala Pro Ala Ser Arg Asp Asn
                165                 170                 175

Ala Arg Met Leu Leu Arg His Arg Gly Ser Val Ala Val Leu Ala Gly
                180                 185                 190

Gly Ile Ala Glu Met Tyr Thr Ser Ser Pro Ser Arg Ala Ala Ala Ala
                195                 200                 205

Thr Glu Pro Asp Glu Ala Ala Ala Gly Gly Ala Ile Asp Thr Thr
 210                 215                 220

Glu Ala Ala Gly Ala Thr Gly Ser Ser Ser Thr Thr Thr Ser Pro Pro
 225                 230                 235                 240

Gln Pro Lys Glu Gln Gln Arg Asp Gly Glu Gln Arg Gln Gly Pro Arg
                245                 250                 255

Lys Gly Leu Lys Gly Leu Leu Lys Gly Pro Lys Asp Asp Pro Asp Pro
                260                 265                 270

Ala Ala Glu Glu Glu Gln Gly Leu Gly Leu Ala Pro Glu Arg Ile Lys
                275                 280                 285

Leu Leu Gly Arg Arg Gly Phe Val Arg Leu Ala Val Glu Met Gly Val
 290                 295                 300

Pro Ile Val Pro Ile Tyr His Met Gly Asn Ser Lys Ile Leu Thr Phe
 305                 310                 315                 320

Gly Pro Gln Ser Leu Gln Leu Ser Arg Leu Arg Met Ala Leu
                325                 330                 335

Gly Ala Val Phe Gly Val Trp Gly Leu Pro Val Pro Arg Pro Gln Pro
                340                 345                 350
```

```
Leu Met Met Cys Val Gly Ser Pro Ile Pro Val Pro Tyr Val Asp Pro
        355                 360                 365

Ala Ala Glu Pro Glu Arg Phe Glu Ala Val Val Ala Ala Val His Gly
    370                 375                 380

Gln Val Ala Ala Phe Gln Asp Leu Tyr Asn Arg Tyr Arg Val Gln
385                 390                 395                 400

Tyr Gly Cys Gly Trp Glu Arg Arg Pro Leu Glu Val Cys
            405                 410
```

<210> SEQ ID NO 34
<211> LENGTH: 1241
<212> TYPE: DNA
<213> ORGANISM: Chlamydomonas reinhardtii

<400> SEQUENCE: 34

```
atgaccccgc gggatccgcc ggtgccgcgg ccgccgccgg gcgtacggca gtacactgac      60
ggccggtcgg cgtcgtacgt actgccgctg ccgtatcgcc tgctggccca gctgactctg     120
ggtttgtacg tgggctttcc ctacatcctg ctggggttgt tgctgggcac ggctgccggc     180
tcgcgcgccg ccgccgccgc cctggctctg acgctgggca gctgctggt gccgccccca     240
ccgcacatcc ggcagggcat gctggactcg gcactgttca ggctgtggcg cgcctacttc     300
aactacagct acgcctacga ccaactgccc gacttcaacc gcccacacat ctttgtcaac     360
agcccgcacg gcgccttccc gctgtcgcag atcctgtgca tctccctgtc caacatcgtg     420
tggccgggct tccccgtgca cagcctggcg gcctcggtgc tgtggtacat accgctgtgg     480
cgccacatga aggcggcgct gggggccgcg cccgccagcc gggacaacgc gcgcatgctg     540
ctgaggcacc gcgggtcggt ggcggtgctg cgggcggca ttgcggagat gtacacgtca     600
tcgccctccc gcgccgccgc tgccaccgaa ccagatgagg ctgcggctgc gggtggggcg     660
atcgacacga ctgaagccgc cggcgccacc ggctcaagca gcaccaccac tagcccgccg     720
cagccaaagg agcagcagcg cgatggggag cagcgccagg ggccgcgcaa ggggctgaag     780
gggctgctga aaggcccgaa ggacgatccc gatccggcgg cggaggagga gcagggcctc     840
gggttggcac tgaacgcat caagctgctg gccggcgcg gcttcgtgcg gctggcggtg     900
gagatgggtg tgcccattgt acccatatac acatgggca acagcaagat cctgaccttc     960
gggccgcagt cactgcagca gctgtcgcgc gcctgcgca tggcgctggg cgccgtgttc    1020
ggcgtgtggg gcctgcctgt gccgcgcccc cagccgctca tgatgtgtgt gggcagcccc    1080
attcccgtgc cgtacgtgga tccagccgcc gagccggagc gcttcgaggc cgtggtggcg    1140
gcggtgcacg gcaggtggt ggcggccttt caggatctgt acaacaggta ccgcgtgcag    1200
tacggctgcg gttgggagcg ccggccgctg gaggtgtgct g                       1241
```

<210> SEQ ID NO 35
<211> LENGTH: 320
<212> TYPE: PRT
<213> ORGANISM: Chlamydomonas reinhardtii

<400> SEQUENCE: 35

```
Met Gln Ser Lys Arg Cys Ala Glu Leu Ala Ser Gly Ala Leu Trp Pro
1               5                  10                  15

Met Asp Arg Asp Gln Met Arg Arg Asp Pro Trp Lys Leu Arg Asp
            20                  25                  30

Arg Ala Ile Ser Gln Ala Trp Val Trp Pro Leu Leu Ile Gly Thr Leu
        35                  40                  45

Leu Tyr Val Gln Ser Thr Thr Leu Thr Ile Ala Phe Leu Leu Trp His
```

```
                    50                  55                  60
Ile Trp Lys Val Met Ala Ser Tyr Phe Pro Gly Ala Arg Leu Ile Lys
 65                  70                  75                  80

Thr Ala Asp Leu Asp Pro Ala Gly Arg Tyr Ile Phe Val Ser His Pro
                 85                  90                  95

His Gly Val Ile Ala Ile Ser Asp Trp Leu Ala Phe Ala Thr Glu Ala
            100                 105                 110

Leu Gly Phe Ser Lys Leu Phe Pro Gly Leu Asp Leu Arg Cys Ala Thr
            115                 120                 125

Leu Ala Ser Asn Phe Trp Val Pro Gly Leu Arg Glu Tyr Ile Leu Ser
        130                 135                 140

His Gly Met Cys Gly Val Gly Arg Asp Thr Leu Ala Arg Val Leu Thr
145                 150                 155                 160

Gly Lys Pro Gly Arg Ala Val Val Leu Val Val Gly Gly Ala Ser Glu
                165                 170                 175

Ala Leu Leu Ala Ala Glu Gly Thr Tyr Asp Leu Val Leu Arg Asn Arg
            180                 185                 190

Lys Gly Phe Val Arg Leu Ala Leu Gln Thr Gly Ala Ser Leu Val Pro
        195                 200                 205

Val Leu Ser Tyr Gly Glu Thr Asp Thr Phe His Thr Tyr Ile Pro Pro
210                 215                 220

Pro Cys Ser Arg Ala Ala Val Met Lys Val Leu Lys Gln Val Phe
225                 230                 235                 240

Gly Phe Ser Thr Pro Leu Cys Trp Gly Thr Gly Leu Phe Gly Gly Trp
                245                 250                 255

Gly Met Leu Ala Leu Gln Val Pro Leu Thr Val Val Gly Ala Pro
            260                 265                 270

Ile Gln Val Asp Lys Val Ser Ser Pro Thr Glu Ala Glu Val Ala Ala
        275                 280                 285

Leu His Lys Thr Tyr Thr Glu Ala Leu Gln Lys Leu Trp Asp Asp Thr
290                 295                 300

Val Asp Lys Tyr Gly Lys Gly Val Lys Arg Pro Leu Ala Ile Val Gln
305                 310                 315                 320

<210> SEQ ID NO 36
<211> LENGTH: 963
<212> TYPE: DNA
<213> ORGANISM: Chlamydomonas reinhardtii

<400> SEQUENCE: 36
atgcaaagta agcgttgtgc agagctggcc tctggggctc tgtggcccat ggaccgcgac    60
cagatgcgcg accgcgaccc atggaagctg cgcgaccgag ctataagcca agcatgggtg   120
tggcctctgc tcatcggcac attgctttac gtgcagagca ccacgctcac aattgccttc   180
ctgctgtggc atatctggaa ggttatggcc tcttacttcc ccggcgcccg cctgattaag   240
accgccgacc tggatccggc tggccgctat atattcgtga ccacccgca cggcgtcatc   300 gccatttccg actggctggc atttgccaca gaggcgctgg gcttctccaa actgttccca   360
ggcctggacc tgcgctgcgc cacgctggct tcaaacttct gggtgcctgg tttgcgtgag   420
tacatcctat cgcacggcat gtgcggcgtg gggcgagaca ctctggcgcg cgtgctgaca   480
ggaaagccgg gccgtgcggt tgtgttggtg gtgggcggcg cgtctgaggc gctgttggcg   540
gcggagggaa cttatgacct ggtgctgcgc aaccgcaagg gctttgtgcg cctgcgctg   600 cagaccggcg ccagtctggt gccggtgctg tcgtacggtg agacagacac cttccacacc   660
```

-continued

```
tacatcccgc cgccctgcag ccgggcggcc gcggtcatga aggtgctgaa gcaggtgttt    720
ggcttctcca cgcccctgtg ctggggcacc ggactgttcg ggggctgggg catgctagcg    780
ctgcaggtgc cgctcactgt ggtggtgggg gcacccatac aggtggacaa ggtgtccagt    840
cccacggagg ctgaggtggc ggcgctgcat aagacctaca cggaggcact gcagaagctg    900
tgggatgaca cagtggacaa gtacggcaag ggtgtcaagc ggccgctggc catcgtgcaa    960
tga                                                                 963
```

```
<210> SEQ ID NO 37
<211> LENGTH: 324
<212> TYPE: PRT
<213> ORGANISM: Chlamydomonas reinhardtii

<400> SEQUENCE: 37
```

Met Ala Ile Asp Lys Ala Pro Thr Asn Val Arg Ile Trp Ser Asp Gly
1               5                   10                  15

Val Thr Glu Lys Gly Lys Gln Ser Ile Phe Ser Ser Leu Val Ala Met
            20                  25                  30

Leu Thr Leu Phe Ile Tyr Cys Gly Trp Met His Val Leu Leu Ala Leu
        35                  40                  45

Val Ile Leu Ser Phe Trp Tyr Arg Trp Ala Leu Val Thr Val Leu Leu
    50                  55                  60

Leu Tyr Ser Thr Leu Leu Pro Pro Lys Pro Val Leu Trp Gly Pro
65                  70                  75                  80

Val Cys Arg Ser Trp Ile Phe Gln Thr Trp Arg Glu Tyr Phe Lys Phe
                85                  90                  95

Ser Tyr Val Phe Asp Glu Val Leu Asp Ser Lys Lys Lys Tyr Ile Phe
            100                 105                 110

Ala Glu Phe Pro His Gly Val Phe Pro Met Gly Pro Leu Ile Gly Ala
        115                 120                 125

Thr Glu Cys Gln Ile Met Phe Pro Gly Phe Asp Ile Phe Gly Leu Ala
    130                 135                 140

Ala Asn Val Val Phe Thr Val Pro Phe Trp Arg His Phe Val Ala Trp
145                 150                 155                 160

Leu Gly Ser Val Pro Ala Thr Thr Arg Asp Phe Lys Arg Val Leu Lys
                165                 170                 175

Gln Gly Ser Val Ala Val Ile Val Gly Ile Ala Glu Met Tyr Met
            180                 185                 190

Gln Ser Pro Thr Lys Glu Gln Ile Met Leu Lys Asp Arg Lys Gly Phe
        195                 200                 205

Val Arg Val Ala Val Glu Glu Gly Val Asp Gly Ile Val Pro Val
    210                 215                 220

Tyr His Phe Gly Asn Ser Gln Val Leu Asp Phe Gly Pro Gln Ala Met
225                 230                 235                 240

Ala Ser Val Ser Arg Arg Leu Arg Ala Ala Leu Gly Phe Leu Tyr Gly
                245                 250                 255

Val Ala Tyr Leu Pro Leu Pro Arg Arg Arg Asn Ile Tyr Met Val Cys
            260                 265                 270

Gly Lys Pro Val Pro Val Thr Arg Thr Ala Arg Asp Asp Pro Lys Phe
        275                 280                 285

Glu Glu Val Val Asp Ala Thr His Ala Ala Val Met Ala Ala Leu Gln
    290                 295                 300

Glu Ala Tyr Asp Arg His Lys Thr Glu Tyr Gly Trp Ala Asp Arg Pro
305                 310                 315                 320

Leu Val Ile Ser

<210> SEQ ID NO 38
<211> LENGTH: 975
<212> TYPE: DNA
<213> ORGANISM: Chlamydomonas reinhardtii

<400> SEQUENCE: 38

| | | | | | |
|---|---|---|---|---|---|
| atggcgattg | ataaagcacc | gacaaatgtg | cgaatttgga | gcgatggcgt | cacggagaag | 60 |
| ggcaagcaaa | gcatcttctc | atcgctggtg | gctatgttga | cgctcttcat | ctactgtggc | 120 |
| tggatgcatg | tgctgctggc | gcttgtgatc | ctgtccttct | ggtaccgctg | gcgctggtg | 180 |
| acggtgctgc | tgctgtactc | caccctgctg | ctgccgccta | agccggtgct | gtggggaccg | 240 |
| gtctgtcgct | cctggatctt | ccagacctgg | cgggagtact | tcaagttctc | ttacgtgttt | 300 |
| gatgaggtgc | tggactcgaa | gaagaagtac | atcttcgcgg | agttcccgca | cggtgtcttc | 360 |
| cccatgggcc | cactcattgg | cgccacagaa | tgccagatca | tgtttcccgg | ctttgacatc | 420 |
| ttcgggctgg | cggcgaatgt | ggtgttcacg | gtccccttct | ggcggcattt | cgtggcgtgg | 480 |
| ctgggctccg | tgccggccac | cacacgcgac | ttcaagcggg | tgctgaagca | aggaagcgtg | 540 |
| gcggtcatcg | tgggaggcat | cgcagagatg | tacatgcaga | gccccacgaa | ggagcagatc | 600 |
| atgttgaagg | accgcaaggg | cttttgttcgt | gtggcggtgg | aggagggcgt | ggatggcggc | 660 |
| atcgtgccgg | tctaccactt | tggcaactct | caggtgctgg | acttcggccc | ccaggccatg | 720 |
| gccagtgtgt | cccgccggct | gcgtgcggcc | ctgggcttcc | tgtacggagt | ggcctacctg | 780 |
| cccctgccca | ggcgccgcaa | catttacatg | gtgtgcggca | agcccgttcc | cgtcacgcgc | 840 |
| accgcccgcg | acgaccccaa | gtttgaggag | gtggttgacg | ccactcacgc | cgctgtgatg | 900 |
| gcggccctgc | aggaggccta | cgaccgccac | aagaccgagt | acggctgggc | cgaccgaccg | 960 |
| ctggtcatca | gctga | | | | | 975 |

<210> SEQ ID NO 39
<211> LENGTH: 327
<212> TYPE: PRT
<213> ORGANISM: Chlamydomonas reinhardtii

<400> SEQUENCE: 39

Met Pro Leu Ala Lys Leu Arg Asn Val Val Leu Glu Tyr Ala Ala Ile
1               5                   10                  15

Ala Ile Tyr Val Ser Ala Ile Tyr Thr Ser Val Val Leu Leu Pro Ser
            20                  25                  30

Ala Leu Ala Leu Phe Tyr Leu Phe Gly Ala Thr Ser Pro Ser Ala Trp
        35                  40                  45

Leu Leu Leu Ala Ala Phe Leu Ala Leu Thr Phe Thr Pro Leu Gln Leu
    50                  55                  60

Thr Thr Gly Ala Leu Ser Glu Arg Phe Val Gln Phe Ser Val Ala Arg
65                  70                  75                  80

Ala Ala Ala Tyr Phe Pro Thr Arg Val Val Thr Asp Pro Glu Ala
            85                  90                  95

Phe Arg Thr Asp Arg Gly Tyr Leu Phe Gly Phe Cys Pro His Ser Ala
        100                 105                 110

Leu Pro Ile Ala Leu Pro Ile Ala Phe Ala Thr Ser Pro Leu Leu
    115                 120                 125

Pro Lys Glu Leu Arg Gly Arg Thr His Gly Leu Ala Ser Ser Val Cys
130                 135                 140

Phe Ser Ala Pro Ile Val Arg Gln Leu Tyr Trp Trp Leu Gly Val Arg

```
              145                 150                 155                 160

Pro Ala Thr Arg Gln Ser Ile Ser Gly Leu Leu Arg Ala Arg Lys Val
                165                 170                 175

Ala Val Leu Val Pro Gly Gly Val Gln Glu Val Leu Asn Met Glu His
            180                 185                 190

Gly Lys Glu Val Ala Tyr Leu Ser Ser Arg Thr Gly Phe Val Arg Leu
        195                 200                 205

Ala Val Gln His Gly Ala Pro Leu Val Pro Val Trp Ala Phe Gly Gln
    210                 215                 220

Thr Arg Ala Tyr Ser Trp Phe Arg Pro Gly Pro Leu Val Pro Thr
225                 230                 235                 240

Trp Leu Val Glu Arg Ile Ser Arg Ala Ala Gly Ala Val Pro Ile Gly
                245                 250                 255

Met Phe Gly Gln Tyr Gly Thr Pro Met Pro His Arg Glu Pro Leu Thr
                260                 265                 270

Ile Val Val Gly Arg Pro Ile Pro Val Pro Glu Leu Ala Pro Gly Gln
            275                 280                 285

Leu Glu Pro Glu Pro Glu Val Leu Ala Ala Leu Leu Lys Arg Phe Thr
        290                 295                 300

Asp Asp Leu Gln Ala Leu Tyr Asp Lys His Lys Ala Gln Phe Gly Lys
305                 310                 315                 320

Gly Glu Glu Leu Val Ile Met
                325

<210> SEQ ID NO 40
<211> LENGTH: 984
<212> TYPE: DNA
<213> ORGANISM: Chlamydomonas reinhardtii

<400> SEQUENCE: 40
atgccgctcg caaagctgcg aaacgtggtg ctggagtacg cggccatagc catctacgtc      60
agcgccatct acacctcggt ggtgctgctg ccctcggcgc tcgcgctgtt ctacctgttt     120
ggggccacca gccctcggc ctggctgctg ctagccgcct tcctggccct caccttcacg      180
ccgctgcagc tgaccaccgg tgcgctgtcg gagcggttcg tgcagttcag tgtggcgcgg     240
gcggcggcct acttccccac cgcgtggtg gtcacggacc cggaggcctt ccgcactgac      300
cgcggctact tgttcggatt ctgcccgcac tcggctctgc catcgcact gcccatcgcc      360 ttcgccacca cctcgccgct gctgcccaag gagctgcgcg ccgcacaca cggcttggcg      420 tcgtccgtgt gcttcagcgc gcccatagtg cggcagctgt actggtggct gggcgtgcgg     480
cccgccacgc ggcagagcat cagcggcctg ttgcgggcgc gcaaggtggc ggtgctggtg     540
ccggggggcg tgcaggaggt gctcaacatg agcacggca aggaggtggc ctacctctcc      600
agccgcaccg gcttcgtgcg actggccgtg cagcacggcg cgccgctggt gccagtgtgg     660
gcgttcggcc agacgcgcgc gtacagctgg ttccggccgg ggccgccgct cgtgcccacg     720
tggctcgtgg agcgcatctc acgtgccgcc ggcgccgtac ccatcggcat gtttgggcag     780
tacggcacgc ccatgccgca ccgcgagccc ctcaccattg tggtgggtcg ccccatcccg     840
gtgccggagc tggcgccggg ccagctcgag cccgagcccg aggtgctggc ggcgctcctc     900
aagcgcttca cggacgacct gcaggcgctg tacgacaagc acaaggcgca gttcggcaag     960
ggcgaggagc tggtcataat gtag                                            984

<210> SEQ ID NO 41
<211> LENGTH: 469
```

<212> TYPE: PRT
<213> ORGANISM: Ostreococcus lucimarinus

<400> SEQUENCE: 41

```
Met Arg Ala Pro Ala Asp Ala Ala Ile Asp Trp Arg Ala Pro Ser Ala
1               5                   10                  15

Gly Ala Leu Ala Cys Leu Leu Ala Val Ala Ile Thr Asn Phe Gly Val
            20                  25                  30

Gly Gly Ala Leu Phe Gly Gly Arg Gly Trp Arg Ala Trp Gln Pro Phe
        35                  40                  45

Ala Arg Gly Arg Ser Trp Arg Phe Thr Leu Ala Gln Ala Ile Gly Trp
    50                  55                  60

Thr Leu Ala Ser Ala Ser Leu Ala Cys Val Met Ala Cys Gly Thr Leu
65                  70                  75                  80

Val Trp Arg Asp Ala Arg Asp Ala Arg Asp Gly Thr Arg Glu Arg
                85                  90                  95

Arg Leu Ala Val Ala Ala Leu Ser Trp Thr Ser Leu Gly Leu Ser Val
            100                 105                 110

Ala Ser Glu Ala Ala Val Ala Ala Ser Leu Ala Phe Phe Asp Val Gln
        115                 120                 125

Asp Glu Gly Glu Ala Gly Arg Gly Ala Ala Arg Gly Arg Glu Gly Leu
130                 135                 140

Asp Phe Arg Asp Val Ala Arg Val Ala Thr Leu Leu Ser Ile Ala His
145                 150                 155                 160

Val Leu His Ala Pro His Ala Val Ile Phe Ala Thr Leu Ala Thr Val
                165                 170                 175

Tyr Ala Leu Gly Ser Ser Gly Ala Leu Ala Ser Ile Val Val Leu Tyr
            180                 185                 190

Ala Ser Thr Tyr Phe Leu Gln Arg Asp Leu Glu Arg Gly Arg Arg Lys
        195                 200                 205

Trp Asp Ala Phe Arg Ala Trp Ser Ser Arg Trp Ile Glu Gly Ala Ala
    210                 215                 220

Lys Ala Trp His Gly Ser Val Arg Met Ile His Asp Gly Ala His Gly
225                 230                 235                 240

Ala Gly Ser Thr Pro Leu Val Phe Ala Tyr His Pro His Ser Leu Ile
                245                 250                 255

Pro Ala Gly Ala Val Trp Phe His Phe Leu Pro Gln Phe Gly Arg Arg
            260                 265                 270

Phe Glu Asn Val Lys Pro Val Thr Leu Ala Ala Ser Val Leu Phe Lys
        275                 280                 285

Pro Pro Phe Val Arg Glu Leu Ala Ala Trp Leu Gly Val Arg Ser Val
290                 295                 300

Ser Gln Glu Ile Phe Arg Ser Thr Leu Arg His Glu Arg Ala Val Val
305                 310                 315                 320

Val Cys Pro Gly Gly Gln Gly Glu Met Cys His Val Gly Gly Leu
                325                 330                 335

Lys Glu Glu Thr Ile Thr Leu Cys Thr Lys His Arg Gly Phe Val Arg
            340                 345                 350

Leu Ala Ile Glu Glu Lys Ala Arg Leu Val Pro Val Val Cys Phe Gly
        355                 360                 365

Glu Ser Ser Ser Trp Arg Asn Leu Leu Arg His Pro Gly Arg Tyr Leu
    370                 375                 380

Tyr Arg Arg Phe Arg Val Ala Thr Pro Leu Leu Ala Val Gly Tyr Leu
385                 390                 395                 400
```

Gly Ile Leu Pro Ile Pro Ala Arg Val Pro Leu Thr Phe Val Val Gly
            405                 410                 415

Asp Pro Met Ser Leu Pro Glu Pro Asp Ala Gly Arg Ala Arg Glu
            420                 425                 430

Ser Asp Val Glu Ile Ala His Ala Ala Tyr Tyr Arg Glu Val Ala Arg
            435                 440                 445

Leu Phe Ala Lys His Lys Gly Ala Ser Gly Phe Pro Asn Leu Asn Leu
            450                 455                 460

Lys Leu Leu His Glu
465

<210> SEQ ID NO 42
<211> LENGTH: 1410
<212> TYPE: DNA
<213> ORGANISM: Ostreococcus lucimarinus

<400> SEQUENCE: 42

```
atgcgcgcgc cgcggacgc  ggcgatcgat  tggcgcgcgc  cgtccgcggg  cgcgctcgcg    60
tgcctgctcg  cggtggcgat  cacgaacttt  ggcgtcggtg  gcgcgctgtt  cggaggacga   120
ggatggcgcg  cgtggcaacc  gttcgcgcga  ggacgatcgt  ggaggttcac  gctggcgcaa   180
gcgatcggat  ggacgctggc  gagcgcgtcg  ctggcgtgcg  tgatggcgtg  cgggacgctg   240
gtgtggcgag  acgcgaggga  cgcgagggac  gacgggacgc  gcgagcggcg  actggcggtg   300
gcggcgctga  gttggacgag  cctgggactg  agcgtcgcga  gcgaggcggc  ggtggcggcg   360
tcgctggcgt  tcttcgacgt  ccaggacgag  ggcgaggcgg  ggcgaggcgc  ggcgagggga   420
agggaaggtt  tggattttag  agacgtcgcg  cgcgtcgcga  cgctgttgtc  catcgcgcac   480
gtgttgcacg  cgccgcacgc  ggtgattttc  gcgacgctgg  cgacggtgta  cgcgctcggg   540
tcgtcgggag  cgctggcgtc  catcgttgtt  ctgtacgcga  gcacgtattt  cttgcagcgc   600
gatctcgagc  gcgggcgccg  gaagtgggac  gcgtttcgag  cgtggtcgtc  gcgatggata   660
gagggcgcgg  cgaaggcgtg  gcacgggagc  gtgcgcatga  ttcacgacgg  cgcgcacggc   720
gcgggctcga  cgcctctcgt  cttttgcctat  caccccgcact  cgctcattcc  ggcgggcgcc   780
gtgtggtttc  acttttttacc  tcagtttggt  cgtcgctttg  aaaacgtcaa  gcccgtgacg   840
ttggccgcga  cgttctttt  caagccgccg  ttcgtgcgag  agctcgccgc  gtggttgggc   900
gtgcgcagcg  tgtcgcaaga  aatatttcgt  tcgacgcttc  gtcacgagcg  cgcggtcgtc   960
gtgtgtccgg  cggtcaggg  cgagatgtgc  gagcacgtcg  gcggattgaa  ggaggagacc  1020
atcacgctct  gcacgaaaca  tcgcgggttc  gttcgactcg  ccatcgaaga  aaaagcgcgt  1080
ctcgtgcccg  tcgtgtgttt  cggcgagagt  agcagctggc  gcaatctctt  gcggcacccc  1140
ggtcgatatt  tgtacagacg  ctttcgcgtc  gcgacgccgc  ttttagcggt  gggctacctc  1200
ggcattctcc  cgattccggc  ccgagtgccg  ctcacgttcg  tcgtcggcga  cccgatgtcg  1260
cttcccgagc  ccgatgacgc  gggacgagcg  agggagagcg  acgttgagat  cgctcacgcg  1320
gcgtattacc  gcgaggtggc  gcgcttgttc  gcaaagcaca  agggcgcgag  cggatttccg  1380
aatttaaact  tgaaattgct  gcacgagtga                                      1410
```

<210> SEQ ID NO 43
<211> LENGTH: 316
<212> TYPE: PRT
<213> ORGANISM: Ostreococcus lucimarinus

<400> SEQUENCE: 43

Met Phe Ala Trp Leu Gly Leu Ile His Val Asp Val Ala Val Thr Ala

```
            1               5                  10                 15
Leu Ala Val Trp Thr Leu Pro Ser Ala Met Ala Val Thr Ala Leu Ala
                      20                  25                  30

Thr Leu Val Ala Ala Ala Ile Pro Arg Thr Val Ala Thr Pro Arg
             35                  40                  45

Trp Gly Ala Arg Leu Ala Arg Ala Val Thr Arg Thr Ala Thr Ala Tyr
         50                  55                  60

Phe Pro Thr Arg Leu Glu Phe Glu Asp Glu Ala Tyr Leu Arg Ala
65                  70                  75                  80

Val Arg Asn Glu Glu Ala Cys Val Ile Gly Leu Glu Pro His Gly Val
                 85                  90                  95

Leu Pro Leu Ser Val Ile Ser Phe Ala Glu Tyr Phe Met His Asp Glu
             100                 105                 110

Glu Gly Ala Arg Arg Gly Leu Thr Pro Ala Ala Arg Arg Gly Ala
             115                 120                 125

Arg Ala Leu Ala Ser Ala Ala Ile Phe Lys Val Pro Leu Val Lys His
130                 135                 140

Leu Trp Thr Trp Leu Gly Leu Asp Pro Ile Ser Lys Ala Cys Met Leu
145                 150                 155                 160

Arg Met Leu Arg Ala Gly Lys Thr Ala Val Ile Ile Pro Gly Gly Val
                 165                 170                 175

Ala Glu Cys Met Ala Met Glu Arg Gly Val Thr Leu Tyr Leu Arg
             180                 185                 190

Lys Arg Tyr Gly Phe Val Lys Ile Ala Ile Val Thr Gly Ala Lys Leu
                 195                 200                 205

Ile Pro Ala Tyr Thr Phe Gly Gln Ser Arg Tyr Gly Tyr Trp Arg
             210                 215                 220

Leu Gly Pro Pro Ile Val Pro Lys Phe Val Ala Asp Trp Ile Gly Lys
225                 230                 235                 240

Thr Phe Ser Phe Ala Pro Ile Ile Phe Trp Gly Lys Phe Cys Thr Pro
                 245                 250                 255

Ile Pro Tyr Ala Thr Ala Leu Asn Thr Val Val Gly Lys Pro Ile Glu
             260                 265                 270

Val Glu Lys Asn Pro Asp Pro Ser Lys Glu Val Gln Ala Lys Leu
             275                 280                 285

Asp Glu Phe Ile Asp Ala Met Arg Ser Leu Tyr Asp Ser His Lys Ala
             290                 295                 300

Arg Phe Gly Tyr Glu Asp Val Arg Leu Val Ile Cys
305                 310                 315

<210> SEQ ID NO 44
<211> LENGTH: 951
<212> TYPE: DNA
<213> ORGANISM: Ostreococcus lucimarinus

<400> SEQUENCE: 44
atgttcgcgt ggctcggatt gattcacgtc gacgtcgcgg tgacggcgct ggcggtgtgg      60
acgctgccga gcgcgatggc ggtgacggcg ctcgcgacgc tggtcgcggc ggcggcgatc     120
ccgcggacgg tggcgacgcc gaggtggggc gcgcggttgg cgcgcgcggt gacgaggacg     180
gcgacggcgt actttccgac gcgattggaa ttcgaagacg aggaggcgta tctgcgagcg     240
gtgaggaacg aagaggcgtg cgtgatagga ctgaaccgca cggggtgctg ccgctgagc      300 gtgatatcgt tcgcggagta ttttatgcac gatgaggagg gggcgcggcg acgaggattg     360
acgccggcgg cgagacgagg cgcgcgggcg ctggcgagcg cggcgatatt taaagtcccg     420
```

```
ctcgtgaaac atctgtggac gtggttgggg ttggatccga tctcgaaggc gtgcatgctg    480
aggatgctgc gagcggggaa gacggcggtg atcattcccg gcggcgtcgc cgagtgcatg    540
gcgatggaac gcggcgtgga gacgttgtat ttgcgcaagc gatacggatt cgtgaagatc    600
gccatcgtga ccggagcgaa actgattccc gcgtacacgt tcggacaaag tcggacgtac    660
gggtactggc ggctcgggcc gccgatcgtg ccgaaattcg tggcggattg gatcgggaag    720
acgttttcgt tcgcgccgat tattttctgg gggaaatttt gcacgcccat cccgtacgcg    780
acggcgctca acacggtcgt gggcaaaccg atcgaggttg aaaaaaaccc agatccgagc    840
aaggaagagg ttcaggcgaa attggacgag tttatcgacg ccatgcgttc gctgtacgac    900
agtcacaagg cgagattcgg ttacgaagac gttcgactcg tgatttgtta g             951
```

<210> SEQ ID NO 45
<211> LENGTH: 338
<212> TYPE: PRT
<213> ORGANISM: Ostreococcus lucimarinus

<400> SEQUENCE: 45

```
Met Ile Tyr Ala Trp Ile Leu Ser Ala Ile Phe Val Tyr Pro Ala Tyr
1               5                   10                  15

Cys Val Phe Gly Pro Ser Met Trp Leu Lys Asn Phe Phe Leu Gly Tyr
            20                  25                  30

Ile Ala Trp Tyr Ala Thr Leu Asp Arg Lys Thr Ala Ser Ser Gly Lys
        35                  40                  45

Arg Phe Ala Arg Trp Ser Arg Arg Leu Pro Phe Trp Arg Ile Leu Ala
    50                  55                  60

Glu Tyr Phe Pro Val Arg Leu His Val Ser Ala Lys Leu Asp Pro Ser
65                  70                  75                  80

Gly Asn Tyr Leu Phe Gly Tyr His Pro His Gly Val Ile Gly Val Gly
                85                  90                  95

Ala Leu Leu Thr Phe Ala Thr Glu Ala Thr Gly Phe Tyr Glu Ala Phe
            100                 105                 110

Pro Gly Leu Asp Leu Arg Leu Leu Thr Leu Ser Met Asn Phe Lys Phe
        115                 120                 125

Pro Phe Thr Arg Glu Val Leu Met Gly Leu Gly Ile Asn Ser Val Thr
    130                 135                 140

Lys Ser Ser Val Glu Thr Asn Leu Thr Arg Ala Pro Gly Ala Ser Val
145                 150                 155                 160

Ala Ile Val Ile Gly Gly Ala Ser Glu Ala Leu Asp Ala Arg Pro Gly
                165                 170                 175

Trp Ala Thr Leu Thr Leu Ala Arg Arg Lys Gly Phe Val Lys Met Ala
            180                 185                 190

Leu Arg Thr Gly Ala Ser Leu Val Pro Val Phe Ala Phe Gly Glu Asn
        195                 200                 205

Asp Ile Phe Glu Gln Val Glu Asn Pro Glu Gly Gly Arg Leu Arg Asn
    210                 215                 220

Phe Gln Met Tyr Ile Lys Gln Leu Ile Gly Ile Thr Pro Pro Ala Phe
225                 230                 235                 240

Tyr Gly Arg Ser Leu Ser Arg Gly Met Trp Arg Ile Phe Gly Arg
                245                 250                 255

Lys Gly Val Leu Pro Lys Arg Glu Pro Ile Glu Val Val Gly Asn
            260                 265                 270

Pro Ile Ala Val Pro Lys Val Val Asp Pro Ser Asn Glu Ile Ile Asp
        275                 280                 285
```

```
Lys Tyr His Ala Leu Tyr Thr Glu Ser Leu Lys Glu Leu Tyr Glu Leu
        290                 295                 300

His Arg Arg Gln Phe His Arg Leu Asn Arg Gly Gly Ser Ser Asp Asp
305                 310                 315                 320

Leu Leu Ser Asp Leu Leu Thr Arg Gln Gly Lys Leu Gly Asn Met Gln
                325                 330                 335

Phe Lys

<210> SEQ ID NO 46
<211> LENGTH: 1017
<212> TYPE: DNA
<213> ORGANISM: Ostreococcus lucimarinus

<400> SEQUENCE: 46
atgatatacg cgtggatact gagcgcgata ttcgtatatc ccgcgtattg cgtgttcggg      60
ccgtcgatgt ggttgaagaa tttcttcctg gggtacatcg cgtggtacgc gacgctcgac     120
aggaagacgg cgagctcggg gaagcgtttc gctcgatggt ctcggcggtt accgttttgg     180
aggattttgg cggagtattt tccggtgcga ttacacgtga gcgcgaagtt agatccgagc     240
ggtaattact tgttcggtta tcatccgcac ggcgtcatcg gcgtcggcgc gttgttgacg     300
ttcgccaccg aggcgacggg attttacgaa gcatttccgg gactcgattt gcgtcttctc     360
acgctgtcca tgaacttcaa gttcccgttc actcgcgagg tgttgatggg gctcgggatc     420
aatagcgtga ccaagtcgag cgtggagacg aatctgacgc gcgcgccggg ggcgtccgtc     480
gccatagtca tcggcggcgc ctccgaagcg ttggacgcgc gtccgggctg ggccacgctc     540
acgctcgcca gacgcaaggg gttcgtaaag atggctcttc gcacaggagc atcgctcgtg     600
cccgtgttcg cgttcggcga gaatgacatc ttcgaacaag tggaaaatcc cgaaggcgga     660
cgattgagga atttccaaat gtacatcaaa caactcattg gcatcacgcc gcctgctttt     720
tacgggcggt cgctcagtcg aggcatgtgg cgtcgaatct ttggtcgcaa aggtgtgctt     780
ccgaagcgtg agccgatcga agtcgtcgtg ggcaatccca tcgccgtgcc caaagtcgtc     840
gatccgtcaa acgaaatcat cgacaagtac cacgccctgt acaccgaatc tttgaaagag     900
cttacgagt acatcgtcg acagtttcat agactcaatc gcgggggggtc gtcggatgat     960
cttctgagcg atctcctgac tcggcaagga aaactgcaaa acatgcagtt caagtag       1017

<210> SEQ ID NO 47
<211> LENGTH: 350
<212> TYPE: PRT
<213> ORGANISM: Ostreococcus lucimarinus

<400> SEQUENCE: 47

Met Gly Ser Asn Ala Gln Arg Gly Ala Leu Trp Arg Glu His Arg Ala
1               5                   10                  15

Val Glu Ala Ala Thr Ile Ala Ala Met Arg Ala Arg Gly Val Arg Asp
                20                  25                  30

Val Pro Trp Ser Ser Ala Lys Arg Met Leu Ala Val Leu Cys Val Ser
            35                  40                  45

Ala Ile Tyr Thr Ser Trp Ile Leu Ser Pro Val Val Ser Ala Val Ala
        50                  55                  60

Val Ile Leu Ile Pro Ser Leu Arg Ala Tyr Val Gly Cys Tyr Leu Phe
65                  70                  75                  80

Ala Ser Tyr Ala Leu Gly Val Arg Val Pro Met Asn Gly Leu Tyr Lys
                85                  90                  95
```

```
Phe Phe Cys Gly Leu Glu Cys Gly Glu Glu Asn Gly Trp Glu Leu Val
                100                 105                 110
Val Glu Asp Ala Thr Ala Gly Glu Lys Glu Ile Asp Cys Ser Lys Arg
            115                 120                 125
Ala Tyr Leu Phe Ala Ala His Pro His Gly Leu Phe Ala Ser Gly Cys
        130                 135                 140
Val Gly Asn Ile Val Leu Ser Asp Ala Ala Leu Arg Arg Phe Arg Ala
145                 150                 155                 160
Arg His Val Arg Phe Phe Ile Asn Asn Leu Leu Ile Ser Val Phe Pro
                165                 170                 175
Ile Ile Lys Asp Val Leu Ser Ser Leu Gly Phe Leu Pro Cys Thr Ala
            180                 185                 190
Lys Met Met Arg Arg Val Leu Gly Arg Gly Glu Thr Gly Met Ile Val
        195                 200                 205
Val Gly Gly Val Gln Glu Val Leu Thr Gly Asn Val Asp Val Glu
210                 215                 220
Glu Leu Tyr Leu Lys Asn Cys Phe Gly Phe Val Lys Val Ala Ile Gln
225                 230                 235                 240
Val Gly Thr Pro Leu Val Pro Val Tyr Thr Phe Gly Glu Ser Leu Ala
                245                 250                 255
Thr Gly Pro Asp Trp Val Pro Phe Arg Glu Ile Arg Lys Arg Leu Ser
            260                 265                 270
Tyr Lys Phe Val Phe Pro Phe Arg Ser Leu Gly Ile Val His Arg Trp
        275                 280                 285
Gly Phe Cys Phe Pro Arg Gly Lys Leu Thr Thr Val Val Gly Pro Pro
        290                 295                 300
Ile Glu Val Lys Gln Asn Asp Arg Pro Ser Arg Glu Glu Val Ala Ala
305                 310                 315                 320
Val His Ala Gln Tyr Cys Lys Ser Leu Leu Ala Leu Ile Glu Arg Asn
                325                 330                 335
Lys Ala Ala Ala Gly Tyr Pro Thr Gln Val Thr Arg Leu Val
            340                 345                 350

<210> SEQ ID NO 48
<211> LENGTH: 1053
<212> TYPE: DNA
<213> ORGANISM: Ostreococcus lucimarinus

<400> SEQUENCE: 48
atgggctcga acgcgcagcg cggtgcgctc tggcgcgaac accgcgccgt ggaggcggcg    60
acgatcgcgg cgatgcgcgc gcgcggcgtg cgcgacgtgc cgtggagctc cgcgaagcgc   120
atgctcgcgt gctgtgcgt cagcgcgatt tacacgtcgt ggatcctgtc cccggtcgtg   180
tccgcggtgg cggtgatttt gataccgtcg ttgcgagcgt acgtcgggtg ttatctcttc   240
gcgtcgtacg cgctcgggt gcgtgtgccc atgaatgggc tttataaatt cttttgcggg   300
ctcgagtgcg gagaagaaaa tggatgggaa ctcgtcgtcg aggacgcgac ggcgggcgag   360
aaagagattg attgctctaa gcgcgcgtat ttgttcgccg cgcacccgca cgggttattc   420
gcgtctggtt gcgtggggaa tatcgtattg agcgacgcgg cgttgaggcg attccgagcg   480
cggcacgtta gattcttcat caacaacttg ctcataagcg tgtttccgat catcaaagat   540
gtgctgtcgt cgcttgggtt cttaccatgc acagcaaaaa tgatgcgacg ggttttaggg   600 cgtgggggaga ctgggatgat tgttgttggc ggcgttcaag aggtgtgct gacgggcaac   660 gtcgacgtcg aagagctata cttgaagaat tgtttcggat tcgtcaaggt agccatccaa   720
```

```
gtcggaacgc ccttagtgcc agtatacacg tttggcgagt ctctggctac tggtccggat    780
tgggtgccgt ttcgtgagat acgaaaacgc ctgagctata aatttgtatt tccgttccgc    840
tcgctcggca tcgtccatcg ttggggattc tgctttccgc gaggcaagct cacgacagtg    900
gtgggaccac ctattgaagt taagcagaac gatagaccgt cgcgcgagga agtggctgcg    960
gtgcatgcgc agtattgtaa gtcgcttttg gcactcattg aacgaaacaa agccgccgcg   1020
ggatacccaa cccaggtgac aagattggta tag                                1053

<210> SEQ ID NO 49
<211> LENGTH: 421
<212> TYPE: PRT
<213> ORGANISM: Ostreococcus tauri
<220> FEATURE:
<221> NAME/KEY: misc_feature
<222> LOCATION: (58)..(65)
<223> OTHER INFORMATION: Xaa can be any naturally occurring amino acid

<400> SEQUENCE: 49

Met Ala Ala Ala Asp Ala Lys Ala Ile Val Leu Ala Ser Thr Cys
1               5                   10                  15

Val Leu Val Ala Thr Cys Ala Thr His Phe Gly Ala Gly Arg Ala Leu
            20                  25                  30

Trp Ser Asp Arg Gly Trp Arg Ala Trp Gln Pro Met Arg Gly Arg Arg
        35                  40                  45

Ala Phe Val Ala Leu Gln Pro Val Gly Xaa Xaa Xaa Xaa Xaa Xaa
    50                  55                  60

Xaa Gly Ala Gly Glu Pro Leu Val Gly Val Ser Leu Ala Phe Phe Asp
65                  70                  75                  80

Glu Thr Arg Ala Gly Gly Arg Thr Ser Glu Thr Met Asp Ala Arg Asn
                85                  90                  95

Val Ala Arg Val Val Gln Met Leu Thr Val Leu His Val Val His Ala
            100                 105                 110

Pro His Met Ala Val Phe Ala Val Leu Gly Thr Ala Tyr Ala Leu Gly
        115                 120                 125

Arg Trp Arg Thr Leu Ala Ala Val Val Ala Leu Tyr Ala Ser Thr Tyr
    130                 135                 140

Val Thr Arg Gln Lys Ser Leu Glu Arg Gly Gln Arg Lys Trp Glu Gln
145                 150                 155                 160

Phe Gln Thr Trp Thr Leu Arg Thr Val Glu Gly Ala Ala Lys Ser Trp
                165                 170                 175

Tyr Gly Ser Val Arg Val Val His Asp Gly Lys Val Ser Glu Ala Ala
            180                 185                 190

His Ser Ser Pro His Val Phe Ala Tyr His Pro His Ser Met Val Pro
        195                 200                 205

Ala Gly Ala Val Trp Phe His Met Leu Pro Asp Phe Ser Ala Arg Phe
    210                 215                 220

Arg Gly Ile Gln Pro Val Thr Leu Ala Ala Ser Val Leu Phe Lys Ala
225                 230                 235                 240

Pro Ile Val Arg Glu Leu Ala Ala Trp Leu Gly Val Arg Ala Val Ser
                245                 250                 255

Arg Glu Ile Phe Arg Ser Thr Leu Arg Glu Gln Gly Ala Val Val Val
            260                 265                 270

Cys Pro Gly Gly Gln His Glu Met Gln Glu His Gly Gly Pro Met Glu
        275                 280                 285

Glu Thr Ile Val Leu Cys Thr Lys His Lys Gly Phe Ile Arg Ile Ala
    290                 295                 300
```

```
Ile Glu Glu Arg Ala Arg Val Val Pro Val Ile Cys Phe Gly Glu Ser
305                 310                 315                 320

Lys Ser Trp Thr Asn Ile Met Ala Lys Pro Gly Arg Tyr Leu Tyr Arg
                325                 330                 335

Arg Phe Arg Phe Gly Phe Thr Pro Leu Leu Ala Val Gly Tyr Leu Gly
            340                 345                 350

Ile Leu Pro Leu Pro Arg Arg Val Pro Ile Thr Phe Val Ile Gly Glu
        355                 360                 365

Pro Met Val Leu Pro Asp Pro Asp Ala Leu Thr Gly Leu Ala Lys Glu
    370                 375                 380

Ser Asp Val Asp Ala Phe His Ala Ser Tyr Tyr Ser Gln Val Glu Arg
385                 390                 395                 400

Leu Phe Asp Glu His Lys Ser Lys Ala Gly Phe Pro Glu Leu Cys Leu
                405                 410                 415

Val Met Lys Asn Asp
            420

<210> SEQ ID NO 50
<211> LENGTH: 1266
<212> TYPE: DNA
<213> ORGANISM: Ostreococcus tauri
<220> FEATURE:
<221> NAME/KEY: misc_feature
<222> LOCATION: (174)..(193)
<223> OTHER INFORMATION: n is a, c, g, or t

<400> SEQUENCE: 50
atggcggcgg cggcggacgc gaaagccatc gtcttggcct cgacgtgcgt cctcgtcgcg    60
acgtgcgcga cgcacttcgg cgcgggccga gcgctgtgga gcgatcgagg atggcgggcg   120
tggcagccga tgcgcggacg gcgcgcgttc gtggcgctgc agccggtggg gtgnnnnnnn   180
nnnnnnnnnn nngggggtgc gggtgagccc ttggtggggg tgtcgctggc gttttttgat   240
gagacgcgcg cgggcgggcg gacgtcggag acgatggacg cgcgaaacgt cgcgcgcgtg   300
gtgcagatgt tgaccgtctt gcacgtcgtg cacgcgccgc acatggcggt gtttgcggtg   360
ttggggacgg cgtacgcgtt gggtcgatgg cgtacgctcg cggcggtggt cgcgttgtac   420
gcgtcgacgt acgtgacgag acagaagtcg ctcgagcggg gacagagaaa gtgggagcag   480
ttccagacgt ggacgcttcg gacggtggag ggggcggcga atcgtggta cgggagcgtg   540 cgcgtggtgc acgacgggaa ggtttcggaa gcggcgcatt cgtcgccgca cgtcttcgcg   600
taccacccgc actcgatggt tcccgcgggc gccgtgtggt ttcacatgct cccggatttt   660
agcgcccgtt ttcgcgggat tcaacccgtg acgctcgcag cctcggtttt gtttaaggca   720
ccgatcgtcc gggagcttgc ggcgtggctt ggcgttcgtg cggtgagcag agagattttc   780
cgttcgacgc tacgagagca aggcgcggtt gtcgtgtgcc cgggaggaca gcacgagatg   840
caagagcacg gaggtccgat ggaggagacg atcgtttttat gcaccaaaca taaaggattc   900
attcgaatag cgatcgagga gcgcgcgcgc gtcgtccccg tgatttgttt cggcgagagc   960
aagagttgga ccaacatcat ggcaaagccg ggccgttatc tctacagacg ctttcgattc   1020
ggtttcaccc cgttactagc cgtgggctac ctcggaattc ttccgctccc gagacgcgta   1080
cccatcacgt tcgtcatcgg cgagccgatg gtacttcctg atccggatgc cttgacggga   1140
ctggcgaagg aatcggatgt cgacgcgttc cacgcgtcgt attacagtca agtggagaga   1200
ctgttcgacg agcacaaatc caaagccggg ttccctgagc tttgcctcgt gatgaaaaac   1260
gattag                                                             1266
```

<210> SEQ ID NO 51
<211> LENGTH: 325
<212> TYPE: PRT
<213> ORGANISM: Ostreococcus tauri

<400> SEQUENCE: 51

Met Ser Arg Ser Ile Val Asp His Gly Val Leu Leu Val Trp Leu Gly
1               5                   10                  15

Leu Phe His Ala Leu Val Val Val Val Ala Ile Val Ala Leu
            20                  25                  30

Glu Arg Arg Arg Ala Met Thr Val Leu Ala Ala Leu Met Ser Leu Ser
            35                  40                  45

Val Val Pro Arg Arg Ile Arg Pro Arg Trp Gly Val Thr Leu Ala Arg
50                  55                  60

Ala Ile Thr Arg Thr Ala Lys Ser Tyr Phe Pro Cys Ala Leu Thr Phe
65                  70                  75                  80

Glu Asn Glu Glu Ala Tyr Leu Lys Gly Ala Arg Lys Gly Val Gly Arg
                85                  90                  95

Leu Val Gly Leu Glu Pro His Gly Ala Leu Pro Leu Ser Val Ile Ala
            100                 105                 110

Phe Ala Asp Tyr Phe Met Phe Asp Glu Asp Gly Ile Glu Ala Arg Gly
        115                 120                 125

Met Asn His Ala Ala Ser Met Asn Ser Arg Ala Leu Ala Ser Gly Ala
130                 135                 140

Ile Phe His Val Pro Leu Val Arg His Leu Trp Thr Trp Leu Gly Leu
145                 150                 155                 160

Glu Pro Ile Ser Arg Arg Met Thr Ser Met Leu Ser Asp Gly Ser
                165                 170                 175

Thr Cys Val Ile Val Pro Gly Gly Val Ala Glu Cys Met Ala Met Glu
            180                 185                 190

Arg Gly Val Glu Thr Leu Tyr Leu Lys Arg Arg Tyr Gly Phe Val Lys
        195                 200                 205

Ile Ala Ile Gln Thr Gly Ala Ala Leu Val Pro Ala Tyr Thr Phe Gly
210                 215                 220

Gln Thr Arg Ala Tyr Lys Tyr Trp Arg Leu Gly Pro Pro Leu Val Pro
225                 230                 235                 240

Thr Ser Val Ala Asn Trp Phe Ser Lys Thr Phe Ser Phe Ala Pro Met
                245                 250                 255

Val Phe Trp Gly Lys Trp Phe Thr Pro Ile Pro Tyr Ala Thr Pro Leu
            260                 265                 270

His Thr Val Val Gly Glu Leu Ile Glu Thr Thr Gln Asn Asp Asn Pro
        275                 280                 285

Ser Arg Glu Glu Val Gln Ala Lys Leu Asp Glu Phe Ile Val Ala Met
290                 295                 300

Arg Ser Leu Tyr Asp Arg His Lys Ser Ala His Gly Tyr Ala Asp Val
305                 310                 315                 320

Asp Leu Val Val Cys
            325

<210> SEQ ID NO 52
<211> LENGTH: 978
<212> TYPE: DNA
<213> ORGANISM: Ostreococcus tauri

<400> SEQUENCE: 52

```
atgtcgcgct cgatcgtcga tcacggcgtg ctgctcgtgt ggttgggggtt gttccacgcc    60
ctggtcgtcg tcgtcgtcgt cgcgatcgtc gcgctcgagc gacgacgcgc gatgacggtg   120
ctcgccgcgt tgatgtcttt gagcgtcgtc ccgcggcgca tccgaccgcg ctggggcgtg   180
acgctggcgc gcgcgatcac gcgcacggcg aagtcgtatt tcccgtgcgc gttgacgttt   240
gagaacgagg aggcgtacct gaagggtgct cggaagggtg tcgggcggtt ggtgggtttg   300
gagccgcacg gagcgctgcc gctctcggtg atcgcgttcg cggattactt catgttcgat   360
gaagatggga tcgaggcgag ggggatgaat cacgctgcgt cgatgaattc gcgagcgttg   420
gcgtcggggg cgatatttca cgtcccgttg gtgcgacacc tgtggacgtg gttgggattg   480
gaaccgatat ctcgaaggcg gatgacgagt atgttaagcg acggttcgac gtgcgtgatc   540
gtgccgggtg ggtggcgga gtgcatggcg atggagagag gggttgagac gctgtatctc   600
aagcgaaggt acgggttcgt gaagattgcg atacagacgg gcgcggcact cgtgccggcg   660
tacacgtttg ggcagacgcg ggcgtacaag tactggcgac tcggtccgcc gttggtgccg   720
acgtccgttg caaattggtt ctcgaaaacg ttttctttcg cacccatggt ttttttgggga   780
aagtggttca cgcccattcc gtacgctacc cctctgcaca cggtggttgg cgagctcatc   840
gagaccacgc aaaacgacaa tccgagtcgc gaggaggtgc aggcaaagct tgacgagttc   900
atcgtcgcta tgcgttcgct gtacgaccga cacaaatctg cacacgggta tgccgacgtc   960
gacctcgtcg tgtgctga                                                 978
```

<210> SEQ ID NO 53
<211> LENGTH: 314
<212> TYPE: PRT
<213> ORGANISM: Ostreococcus tauri

<400> SEQUENCE: 53

Met Arg Asn Ala Phe Leu Gly Tyr Ile Gly Trp Tyr Val Leu Leu Asp
1               5                   10                  15

Arg Arg Ser Asp Ser Ser Gly Thr Arg Phe Val Ala Trp Ser Arg Arg
            20                  25                  30

Leu Pro Phe Trp Arg Ile Leu Ala Asp Tyr Phe Pro Val Arg Leu Tyr
        35                  40                  45

Lys Ser Gly Glu Leu Asp Pro Lys Gly Asn Tyr Leu Phe Gly Tyr His
    50                  55                  60

Pro His Gly Val Ile Gly Val Gly Ala Leu Met Thr Phe Ala Thr Glu
65                  70                  75                  80

Ala Thr Gly Phe Tyr Glu Ala Phe Pro Gly Leu Asp Leu Arg Leu Leu
                85                  90                  95

Thr Leu Ser Val Asn Phe Lys Phe Pro Phe Thr Arg Glu Val Leu Met
            100                 105                 110

Ala Leu Gly Ile Asn Ser Val Thr Lys Ala Ser Val Met Thr Asn Leu
        115                 120                 125

Thr Arg Ala Pro Gly Ala Ser Val Ala Ile Val Ile Gly Gly Ala Ala
    130                 135                 140

Glu Ala Leu Asp Ala Arg Pro Gly Ser Ala Thr Leu Thr Leu Ala Arg
145                 150                 155                 160

Arg Lys Gly Phe Val Lys Met Ala Leu Arg Thr Gly Ala Ser Leu Val
                165                 170                 175

Pro Val Phe Ala Phe Gly Glu Asn Asp Ile Phe Glu Gln Val Glu Asn
            180                 185                 190

Pro Asp Gly Gly Arg Leu Arg Lys Phe Gln Thr Tyr Ile Lys Gln Leu
        195                 200                 205

```
Ile Gly Ile Ser Pro Pro Ala Phe Tyr Gly Arg Ser Leu Ser Arg Gly
    210                 215                 220
Val Trp Arg Arg Ile Phe Gly Arg Lys Gly Val Leu Pro Lys Arg Glu
225                 230                 235                 240
Pro Ile Glu Val Ile Ile Gly Asn Pro Ile His Val Pro Gln Val Asp
                245                 250                 255
Asp Pro Ser Pro Asp Val Ile Asp Lys Tyr His Gln Leu Tyr Thr Val
            260                 265                 270
Gly Leu Lys Glu Leu Tyr Glu Leu His Arg Arg Gln Phe His Gln Leu
        275                 280                 285
Asn Arg Gly Gly Ser Ser Asp Asp Leu Leu Ser Asp Leu Ile Lys Arg
    290                 295                 300
Lys Asn Asn Leu Gln Ala Met Thr Phe Lys
305                 310

<210> SEQ ID NO 54
<211> LENGTH: 945
<212> TYPE: DNA
<213> ORGANISM: Ostreococcus tauri

<400> SEQUENCE: 54
atgcggaacg cgttcttggg atacattggt tggtacgtgc tgttggaccg gcgctcggat      60
agctcgggca ctagattcgt ggcgtggtcg agacgtctac ctttttggcg catcctggct     120
gattacttcc cagttcgatt atacaagagc ggcgagctcg atccaaaagg gaattacttg     180
ttcgggtatc atccgcacgg cgtcatcggc gtcgggcgt tgatgacgtt tgccaccgaa      240
gcgacgggat tttacgaagc atttccagga ttggatttac ggctcttgac gttatcggtg     300
aacttcaagt ttccatttac gcgagaggtg ttgatggcgc tcgggattaa ctccgtcact     360
aaggcgagcg tcatgaccaa tcttacccgc gcaccaggcg cgagcgtcgc catcgtcatc     420
ggcggcgccg cagaggcgtt ggacgctcgt ccgggatcgg ccacgctcac gctggcgaga     480
cgtaaagggt tcgtgaaaat ggctctgcgc acgggtgcat cgctcgtgcc tgttttgcc      540 ttcggggaga cgatattttt cgagcaagtc gagaatcccg acggcgggcg cctgcgcaag     600
tttcagacgt acatcaagca actcatcgga atctcaccgc cggcttttta cggccgctcg     660
ctcagtcggg gggtgtggcg tcgcattttt ggcgtaagg gagtgctgcc gaagcgtgaa      720
ccgatcgaag tgatcatcgg taatcccata cacgtccctc aggtggacga tccgtcgccc     780
gacgtcatcg acaagtatca tcaattgtac accgtgggac tcaaggaact ttacgagctg     840
catcgcagac aatttcacca gttgaatcgc ggaggttctt ccgacgatct gctaagcgat     900
ctgatcaagc gtaagaacaa cctccaagcc atgacattca aatag                    945

<210> SEQ ID NO 55
<211> LENGTH: 354
<212> TYPE: PRT
<213> ORGANISM: Ostreococcus tauri

<400> SEQUENCE: 55

Met Arg Thr Ser Ser Gly Ala Gly Gly Thr Arg Ala Arg Arg His Cys
1               5                   10                  15

Ala Thr Thr Asp Val Ala Arg Ser Phe Asp Ala Val Arg Glu Met
            20                  25                  30

Arg Glu Ala Arg Gly Ile Ala Asp Val Pro Trp Ser Ser Leu Lys Arg
        35                  40                  45

Leu Leu Gly Val Ser Cys Val Ser Ala Ile Tyr Thr Ser Trp Ile Leu
```

```
                 50                   55                    60
Ser Pro Val Met Ser Ala Leu Ala Val Trp Arg Tyr Glu Trp Leu Arg
 65                  70                      75                  80

Ala Tyr Val Ala Cys Tyr Leu Phe Ala Ser Tyr Ala Leu Gly Val Ala
                     85                      90                  95

Met Pro Met Asn Ala Leu His Arg Phe Phe Cys Trp Leu Glu Thr Gly
                    100                     105                 110

Glu Glu Asn Gly Trp Gln Leu Val Val Glu Asp Cys Asp Val Asp
                    115                     120             125

Cys Ser Lys Arg Ala Tyr Leu Phe Thr Ala His Pro His Gly Leu Phe
                130                     135                 140

Ala Ser Gly Cys Val Gly Asn Val Val Leu Ser Gly Arg Ala Leu Lys
145                     150                     155                 160

Arg Phe Arg Ala Arg Arg Ile Trp Phe Phe Ile Asn Glu Leu Leu Ile
                    165                     170                     175

Arg Val Phe Pro Ile Ile Lys Asp Val Leu Ser Met Leu Gly Phe Val
                180                     185                     190

Pro Cys Thr Ala Lys Met Met Lys Lys Val Leu Gly Arg Gly Glu Thr
                195                     200                     205

Gly Leu Ile Val Val Gly Gly Val Gln Glu Val Val Leu Thr Gly Asn
210                     215                     220

Val Asp Glu Glu Glu Leu Tyr Leu Lys Asn Cys Phe Gly Phe Val Lys
225                     230                     235                 240

Val Ala Met Gln Ala Gly Thr Pro Leu Val Pro Val Tyr Thr Phe Gly
                    245                     250                     255

Glu Ser Leu Ala Thr Gly Pro Asp Trp Val Pro Phe Arg Glu Leu Arg
                260                     265                     270

Lys Arg Leu Ser Tyr Lys Phe Val Phe Pro Phe Arg Ser Leu Gly Ile
                275                     280                     285

Ile His Arg Trp Gly Leu Cys Phe Pro Lys Ala Lys Leu Thr Thr Val
                290                     295                     300

Val Gly Ala Pro Ile Glu Val Lys Gln Asn Pro Asn Pro Thr Arg Glu
305                     310                     315                 320

Glu Val Ala Ala Val His Gln Gln Tyr Cys Asp Ala Leu Leu Ala Met
                        325                     330                 335

Ile Glu Arg Asn Lys Ala Arg Ala Gly Tyr Pro Thr Gln Arg Thr Lys
                340                     345                     350

Leu Val

<210> SEQ ID NO 56
<211> LENGTH: 1065
<212> TYPE: DNA
<213> ORGANISM: Ostreococcus tauri

<400> SEQUENCE: 56
atgcgaacct cctcgggcgc gggaggaacg cgcgcgcgtc gtcactgtgc gacgacggac     60
gtcgcgcgat cgttcgacgc cgttcgcagg gagatgcgag aggcgcgagg gatcgcggac    120 gtccctgga  gctcgctcaa gcgcttgctc ggtgtctcgt gcgtgagcgc gatttacacg    180
tcgtggatcc tctccccggt gatgagcgcg ctcgcggtgt ggcggtacga gtggttgaga    240
gcgtacgtcg cgtgctatct cttcgcgtcc tacgcgctcg gcgtggcgat gccgatgaac    300
gcgctgcatc ggttcttctg ttggctcgag acgggagagg aaaacgggtg gcagctcgtc    360
gtcgaggacg actgcgatgt ggactgctcg aagagggcgt acttgttcac ggcgcatccg    420
```

-continued

```
cacgggttgt tcgcgtcggg atgcgtcggg aacgtcgttt tgagcggacg cgcgctcaag    480
aggttccggg cgagacggat ttggttcttc atcaacgagc tgttaatccg agtgtttccg    540
atcatcaagg acgtgttgtc gatgctggga ttcgtgccgt gcacggcgaa aatgatgaag    600
aaggtgttgg gaaggggcga gaccggattg atcgtcgtcg gtggggttca ggaggttgtg    660
ttgactggta acgtcgacga agaggaactt tatctaaaaa attgtttcgg ctttgtcaaa    720
gtggccatgc aggccgggac gccgctcgtg cccgtataca cattcggcga atcgctagcc    780
accggcccgg actgggtacc gttcagagag ctgcgtaaac ggctgagcta caagtttgtg    840
ttcccgtttc gctcgcttgg cataatccat cgctgggggc tctgctttcc caaggcaaag    900
ctcacgaccg tggtaggcgc gccgattgag gtgaaacaaa acccaaatcc cacgcgcgag    960
gaagttgcgg cggtgcatca gcagtattgc gacgcactgc tggcgatgat tgagcgaaac    1020
aaggcccgcg cggggtatcc gacgcaacgc acaaagttgg tgtaa    1065
```

<210> SEQ ID NO 57
<211> LENGTH: 359
<212> TYPE: PRT
<213> ORGANISM: Phaeodactylum tricornutum

<400> SEQUENCE: 57

```
Met Lys Glu Arg Arg Ser Gly Leu Asn Pro Ser Gly Ser Ser Val Tyr
1               5                   10                  15

Pro Leu His Pro Pro Asp Ser Arg Val Leu Arg Val Pro Ser Asp
            20                  25                  30

Ile Ser Phe Leu Asp Arg Leu Ile Val Ala Gly Ser Ser Ile Phe Ile
        35                  40                  45

Val Gly Ser Leu Val Trp Val Pro Leu Thr Ala Arg Trp Val Tyr Arg
    50                  55                  60

Arg Trp Lys Gln Ala Lys Asp Lys Arg Lys Ala Leu Tyr Ala Ser
65                  70                  75                  80

Leu Leu Val Ile Leu Ala Val Leu Val Ile Gly Gly Pro His Arg Ser
                85                  90                  95

Pro Arg Val Gly Lys Trp Leu Gln Val Arg Lys Trp Ser Leu Phe Gln
            100                 105                 110

Ala Trp Val Lys Phe Ile Ala Met Glu Val Ile Leu Asp Gln Pro Lys
        115                 120                 125

Gly Ile Thr Met Asp Val Gln Gln Asp Lys Ala Ile Phe Ala Phe Ala
    130                 135                 140

Pro His Gly Ile Phe Pro Phe Ala Phe Ala Gly Val Leu Pro Asp
145                 150                 155                 160

Ile Ala Thr Gln Ser Phe Gly Tyr Val Arg Pro Val Ala Thr Ala
                165                 170                 175

Thr Arg Leu Phe Pro Val Val Arg Asp Phe Ile Ser Trp Ala Asn Pro
            180                 185                 190

Val Asp Ala Ser Lys Asp Ser Val Glu Arg Ala Leu Ala Leu Gly Asp
        195                 200                 205

Arg Ile Ala Val Ile Pro Gly Gly Ile Ala Glu Ile Phe Glu Gly Tyr
    210                 215                 220

Pro Lys Pro Asn Thr His Pro Asp Glu Glu Tyr Ala Ile Val Arg Ser
225                 230                 235                 240

Gly Phe Leu Arg Leu Ala Ile Lys His Gly Ile Pro Val Ile Pro Val
                245                 250                 255

Tyr Cys Phe Gly Ala Thr Lys Met Leu Lys Arg Leu Glu Leu Pro Gly
            260                 265                 270
```

```
Leu Glu Gln Leu Ser Leu Phe Leu Arg Val Ser Ile Cys Leu Phe Phe
            275                 280                 285

Gly Val Gly Gly Leu Pro Ile Pro Phe Arg Gln Arg Leu Ser Tyr Val
        290                 295                 300

Met Gly Gln Pro Ile Leu Pro Pro Val Arg Thr Thr Gly Ser Asp Ile
305                 310                 315                 320

Ser Asp Ala His Val Lys Glu Met Gln Asp Arg Phe Cys Ala Glu Val
                325                 330                 335

Gln Arg Leu Phe Asp Arg His Lys Glu Ala Tyr Gly Trp Ser His Lys
            340                 345                 350

Thr Leu Lys Leu Leu Glu Gln
        355

<210> SEQ ID NO 58
<211> LENGTH: 1080
<212> TYPE: DNA
<213> ORGANISM: Phaeodactylum tricornutum

<400> SEQUENCE: 58
atgaaagaaa gaagatctgg cctaaatccg tcaggatcct ccgtgtatcc attgcaccct      60
cctgacagtc gcgttctcgt tcgagtcccc tccgatattt cctttcttga tcgtctcatc     120
gtcgctggca gcagtatctt tattgtcggt tcgctagtat gggttccatt gaccgcaaga     180
tgggtctaca ggcggtggaa gcaagctaaa gataaacgaa agcgggcttt gtatgcctct     240
ctactcgtga ttctggcagt tctcgttatt ggcggacccc accgatctcc tcgtgtcggc     300
aaatggctcc aagtacgaaa gtggtccctc ttccaagcgt gggtaaagtt tattgctatg     360
gaagtgattt tggatcaacc gaaaggcatt actatggacg tccaacaaga caaggcgatt     420
tttgcattcg cgccacatgg aatctttccg tttgcgttcg cctttggagt gcttccgat      480 attgccacac aatcgtttgg ctacgttcgt ccggtcgtgg caaccgccac aaggttgttt     540
cctgtagtcc gggatttcat ctcttgggcg aatccggtag acgcttccaa agattccgtt     600
gaacgtgctt tagcattggg cgatcgcatt gctgtaatac ctggaggaat tgcagaaatt     660
ttcgaaggat atccgaaacc gaacacgcat ccggatgaag agtacgctat cgtacggagt     720
ggatttttgc gtttggcaat aaaacacggt atcccagtga ttcccgtata ctgtttcggc     780
gctaccaaaa tgttgaagcg tctggagctt cctggcctgg agcaactgtc cctgtttcta     840
cgcgtgagca tttgcctctt ttttggagtc ggcgggttgc ccatccctt ccgacaacga     900 tgtcgtacg taatgggaca accaattttg ccaccgtaa ggacaacggg cagcgatatt     960
tcggacgcac acgtcaaaga aatgcaagat cgcttttgtg ctgaggtcca gcggctcttt    1020
gatcgacata aggaagctta tggttggtcc cacaaaacgc tgaaactatt ggaacagtga    1080

<210> SEQ ID NO 59
<211> LENGTH: 392
<212> TYPE: PRT
<213> ORGANISM: Phaeodactylum tricornutum

<400> SEQUENCE: 59

Met Arg Glu Arg Ser Cys Ala Asn Ala Ser Asp Asp Ser Ile His
1               5                   10                  15

Lys Gln Ser Pro Glu Leu Glu Ala Glu Phe Leu His Thr Ser Lys Leu
            20                  25                  30

Thr Leu Ala Asp Met Arg Arg Leu Ala His Asp Pro Lys Asp Arg Arg
        35                  40                  45
```

```
Leu Ala Thr Lys Pro Ala Ala Gln Ala Thr Lys Glu Asp Val Leu Thr
 50                  55                  60

Val Gln Pro Met Ser Phe Val Glu His Thr Ala Cys Cys Leu Phe Leu
 65                  70                  75                  80

Ala Phe Gly Val Pro Asn Gly Ala Leu Thr Ile Pro Ile Ala Thr Trp
                 85                  90                  95

Leu Ile Gly Lys Phe Val Val Arg Asn Val Phe Leu Ala Phe Leu Leu
                100                 105                 110

Ala Gly Cys Ile Leu Leu Pro Leu Ala Ile Leu Pro Gln Glu Tyr Val
            115                 120                 125

Pro Ala Arg Leu Gln Ser Trp Leu Ala Leu Gln Ile Leu Lys Tyr Phe
130                 135                 140

Ser Phe Ser Leu Val Met Glu Glu Arg Pro Pro Thr Met Cys Thr Gly
145                 150                 155                 160

Lys Gln Leu Ile Glu Gln Pro Ala Arg Pro Arg Ile Val Thr Ala Tyr
                165                 170                 175

Pro His Gly Val Phe Pro Tyr Gly Asn Ala Leu Thr Val Val Thr Trp
                180                 185                 190

Pro Leu Leu Thr Gly His His Ile Val Gly Leu Ala Ala Asn Ala Ala
            195                 200                 205

Leu Arg Thr Pro Ile Phe Lys Gln Ile Leu Arg Ser Ile Gly Val Lys
210                 215                 220

Asp Ala Ser Arg Ala Ser Val Arg Asn Ala Leu Glu Thr Trp Pro Phe
225                 230                 235                 240

Thr Val Gly Ile Ser Pro Gly Gly Val Ala Glu Val Phe Glu Thr Asn
                245                 250                 255

His Phe Asn Glu His Ile Leu Leu Lys Glu Arg Ile Gly Val Ile Lys
                260                 265                 270

Met Ala Ile Arg Thr Gly Ala Asp Leu Val Pro Gly Tyr Met Tyr Gly
            275                 280                 285

Asn Thr Asn Leu Tyr Trp Cys Trp Thr Gly Glu Gly Ile Pro Gly Ala
290                 295                 300

Arg Trp Leu Leu Glu Tyr Val Ser Arg Lys Ile Leu Gly Phe Ala Leu
305                 310                 315                 320

Val Pro Ile Ala Gly Arg Trp Gly Leu Pro Ile Pro Tyr Arg Thr Pro
                325                 330                 335

Ile Leu Cys Val Val Gly Lys Pro Ile Pro Thr Ile His Leu Gln Thr
                340                 345                 350

Glu Glu Pro Ser Met Glu Gln Ile Val Asp Ile Gln Glu Gln Leu Ser
            355                 360                 365

Thr Glu Leu Lys Ser Met Phe Asp Arg Tyr Lys His Leu Tyr Gly Trp
370                 375                 380

Glu Asp Arg Met Leu Val Ile Thr
385                 390

<210> SEQ ID NO 60
<211> LENGTH: 1179
<212> TYPE: DNA
<213> ORGANISM: Phaeodactylum tricornutum

<400> SEQUENCE: 60
atgcgtgagc gaagctgcgc caacgcttct gacgatgaca gcattcacaa gcagtcgcca       60
gaattggagg ctgagtttct tcataccagc aagttgacct tagccgacat gcgacgattg      120
gcgcacgatc cgaaggatcg gaggttggca acaaaacctg cggcgcaagc tacgaaagaa      180
```

```
gacgtcttga cggtacaacc catgagtttc gtagaacaca ctgcttgctg tctgtttctc      240
gcgtttggag tgcccaatgg cgctctgacg attcccatag caacgtggct gatcggaaaa      300
ttcgtggtac gcaacgtttt cttggcgttt ctgttagcag gctgtatact tctaccgctt      360
gcgatactgc cgcaagaata tgtgcccgcc cgattgcaat cgtggcttgc tttgcagata      420
ctgaaatatt tttcttcctc tttggtcatg gaggaacgcc ctccgacaat gtgtactggc      480
aagcagctga tcgagcagcc cgctcggcca cgaatcgtca cagcctatcc gcacggagtt      540
ttcccatacg gaaacgcgtt gactgtagtc acatggccgt tgttgacggg acaccatatt      600 gtgggttttgg cagcaaatgc cgctttgcgg acaccgatct ttaaacaaat cttgcggagc      660
attggcgtca aggacgcctc tcgagcgtcg gtacggaatg cgctggaaac atggcctttc      720
accgtcggga tttcgccagg tggcgtggcg gaagttttg aaacaaacca cttcaatgag       780
cacattctgt tgaaagaacg tattggtgtc atcaagatgg ccattcgcac cggtgcggat       840
cttgtaccag gctatatgta tggtaatact aatctgtact ggtgctggac aggggaaggt       900
attcctggag ctcggtggct attggagtat gttttcgcgta aaatcctagg ttttgccctc       960
gtgcctatag cgggtagatg gggactacca ataccgtaca ggactccgat attgtgtgtc      1020
gtgggcaagc caataccaac cattcatttg caaaccgaag aaccatcaat ggagcaaatc      1080
gtggacattc aggaacaatt gtcaacagaa ttgaaatcaa tgttcgaccg ctataagcac      1140
ctgtacggat gggaagatcg aatgctagtg atcacataa                             1179
```

<210> SEQ ID NO 61
<211> LENGTH: 329
<212> TYPE: PRT
<213> ORGANISM: Phaeodactylum tricornutum

<400> SEQUENCE: 61

```
Met Glu Arg Thr Lys Ile Gln Asp Glu His Lys Ser Pro Asn Pro
1               5                   10                  15

Ser Thr Phe Arg Trp Phe Leu Gly Leu Leu Val Ala Ser Thr Phe Ser
            20                  25                  30

Met Val Tyr Phe Val Ala Pro Phe Tyr Met Leu Thr Val Phe Ala
            35                  40                  45

Leu Val Phe Lys Tyr Pro Ser Val Glu Ile Ala Trp Met Tyr Ala Ile
50                  55                  60

Pro Met Ile Val Ser Ala Ile Leu Pro Pro Met Ala Ser Pro Leu Ala
65                  70                  75                  80

Leu Arg Leu Ile Ser Pro Leu Ile Asp Tyr Phe Asp Tyr Glu Glu Ile
                85                  90                  95

His Glu Thr Ser Pro Val Asp Val Gln Lys Glu Ile Leu Ser Asn Asn
            100                 105                 110

Lys Asn Tyr Leu Leu Val Phe Gln Pro His Gly Ala Leu Ser Phe Thr
        115                 120                 125

Gly Ile Thr Ser Met Val Thr Ala Pro Gln Ala Met Lys Gly Lys Leu
    130                 135                 140

Pro Thr Ala Val Ala Asp Ala Leu Leu Tyr Thr Pro Ile Leu Lys His
145                 150                 155                 160

Val Leu Gly Ile Phe Gly Leu Ile Ser Ala Ser Lys Ser Ser Met Ile
                165                 170                 175

Arg Thr Leu Lys Lys Lys Gly Val Glu Gly Thr Ile Val Leu Tyr Val
            180                 185                 190

Gly Gly Ile Ala Glu Leu Phe Leu Thr Asp Glu Thr Asp Glu Arg Leu
        195                 200                 205
```

```
Tyr Leu Arg Lys Arg Lys Gly Phe Ile Lys Leu Ala Leu Gln Gln Gly
    210                 215                 220

Val Asp Val Val Pro Val Tyr Leu Phe Gly Asn Thr Asn Ala Leu Ser
225                 230                 235                 240

Val Leu Lys Thr Gly Phe Leu Ala Ala Ile Ser Arg Lys Leu Gln Ile
                245                 250                 255

Ser Leu Thr Tyr Ile Trp Gly Lys Trp Tyr Leu Pro Ile Pro Arg Asp
                260                 265                 270

Cys Lys Leu Leu Tyr Ala Ser Gly Gln Pro Leu Gly Met Pro His Ile
                275                 280                 285

Leu Asp Pro Ser Gln Ala Asp Ile Asp Lys Trp His Glu Lys Tyr Cys
    290                 295                 300

Ser Glu Val Met Arg Ile Phe Glu Lys Tyr Lys Glu Lys Val Pro Glu
305                 310                 315                 320

Tyr Lys His Lys Lys Leu Glu Ile Ile
                325

<210> SEQ ID NO 62
<211> LENGTH: 990
<212> TYPE: DNA
<213> ORGANISM: Phaeodactylum tricornutum

<400> SEQUENCE: 62
atggagagaa caaagataca agacgagcac aaaagtcccc ctaatccgtc gacatttcga      60
tggttcctcg gccttctagt ggcgtcgacg ttttccatgg tctatttgt ggctcccttt     120 tacatgctta cagtcgtgtt tgcactagtt ttcaaatatc cttcggtaga aattgcatgg    180
atgtacgcta ttccgatgat tgtctcggcc attttgccac caatggcttc tccacttgcc    240
ttgcgactca tctccccgct cattgactac ttcgattacg aagagatcca cgaaacctca    300
ccggtggacg tccagaagga aatactaagc aacaacaaaa actatttgct agtctttcaa    360
ccgcatggag cactgtcgtt tacaggaatc acttcaatgg tgacagctcc acaagcaatg    420
aaaggcaaat tgccaacagc tgtggctgac gcactcttgt acacacctat actgaaacat    480
gtcttaggaa ttttcgggct gattagtgcc tccaaaagca gcatgatccg aacttttaaaa   540 aagaagggtg tggaaggaac cattgttttg tacgttggtg ggattgccga gctcttttg    600 accgacgaga cggacgagcg cctctatctg cgaaagcgaa aagggtttat caaattagct    660
ctacaacagg gtgtcgatgt tgtacctgtg tatctatttg gaacacacaa cgcgctgtcg   720
gtactaaaga cgggatttct cgcggcaatt cgcgaaaat tacagatatc tctgacgtac   780
atttggggaa agtggtatct tccgattccc cgtgattgca aattgctgta tgcttccggt   840
cagccattag gaatgcctca tttttagac ccaagccaag ccgacattga taaatggcac    900
gaaaagtact gctccgaggt catgcggatc ttcgaaaaat acaaggaaaa ggttccggaa    960
tacaagcaca agaaattaga aattatttga                                     990

<210> SEQ ID NO 63
<211> LENGTH: 320
<212> TYPE: PRT
<213> ORGANISM: Phaeodactylum tricornutum

<400> SEQUENCE: 63

Met Thr Arg Ser Lys Phe Ile Gly Ser Ala Gly Ala Ile Gly Leu Phe
1               5                   10                  15

Cys Leu Met Ile Ile Pro Asn Val Gly Ile Leu Ile Ala Thr Phe Leu
                20                  25                  30
```

| Tyr | Pro | Lys | Val | Leu | Gly | Phe | Tyr | Phe | Leu | Ile | Pro | Tyr | Ala | Tyr |
| | | 35 | | | | | 40 | | | | | 45 | | |

Asn Leu Ser Ile Gly Lys His Glu Ala Arg Asp Gly Asn Gly Trp Asn
    50                  55                  60

Trp Phe Ser Glu Asn Phe Val Phe Asn Ile Val Arg Gly Tyr Leu
65                  70                  75                  80

Asn Leu Lys Ile Glu Ala Asp Ser Glu Leu Lys Glu Ala Glu Ala Lys
                85                  90                  95

Glu Gly Ala Gln Phe Val Phe Ala Val Ser Pro His Gly Thr Asn Ala
                100                 105                 110

Asp Tyr Arg Val Phe Ile Asp Gly Met Leu His Glu Ala Leu Pro Gln
            115                 120                 125

Thr Ala Ser Lys Ile Arg Thr Leu Ala Ala Thr Val Leu Phe His Ile
        130                 135                 140

Pro Leu Val Arg Glu Ile Ala Leu Trp Thr Gly Cys Val Asp Ala Ser
145                 150                 155                 160

Arg Ala Val Ala Val Glu Arg Leu Lys Glu Glu Gly Ser Leu Leu
                165                 170                 175

Val Ile Pro Gly Gly Gln Ala Glu Gln Met Tyr Thr Gln Tyr Gly Arg
            180                 185                 190

Glu Arg Val Tyr Leu Lys Arg Arg Lys Gly Phe Leu Lys Leu Cys Leu
            195                 200                 205

Lys Tyr Glu Ile Pro Val Val Pro Ala Tyr Val Phe Gly Val Ser Asp
210                 215                 220

Tyr Tyr Phe Thr Ser Ala Lys Leu Phe Gly Leu Arg Met Trp Leu Val
225                 230                 235                 240

Gln Asn Leu Gly Ile Ala Leu Pro Leu Cys Trp Gly Arg Tyr Gly Leu
                245                 250                 255

Pro Ile Cys Pro Arg Pro Val Asp Thr Thr Leu Val Phe Asp Lys Pro
            260                 265                 270

Leu Tyr Leu Ser Cys Gln Asn Pro Ser Asn Pro Ser Glu Asp Glu Val
        275                 280                 285

Asp Lys Ala His Leu Gln Phe Cys Gln Ala Leu Glu Lys Leu Phe Asp
    290                 295                 300

Thr His Lys Glu Arg Leu Gly Tyr Gly Asp Arg Lys Leu Glu Ile Ile
305                 310                 315                 320

<210> SEQ ID NO 64
<211> LENGTH: 963
<212> TYPE: DNA
<213> ORGANISM: Phaeodactylum tricornutum

<400> SEQUENCE: 64

| atgaccagat cgaagtttat aggaagtgct ggagctattg gcttattttg tttgatgatc | 60 |
| ataccgaatg tgggaattct gatcgcaaca tttctttatc ccaaagtact tgggttctac | 120 |
| tttctgattc cgtactacgc atacaacttg tccattggca acacgaagc tcgagacggc | 180 |
| aacggctgga attggttcag cgagaatttc tttgtcttta acattgtgag gggatatcta | 240 |
| aatcttaaga ttgaagctga ctccgagctc aaggaagccg aagcgaaaga aggcgcccaa | 300 |
| tttgtgttcg ccgttagccc tcacggaacg aacgcagact tcgagttttt tattgacggt | 360 |
| atgctacatg aggcactccc acagactgca agcaagatca gaacactagc ggcgacagta | 420 |
| ctgttccaca ttcccttggt tcgtgaaatc gcactttgga caggatgtgt cgatgccagc | 480 |
| cgcgcagttg ctgtcgagag attaaaagaa gaaggtggtt cactgcttgt gattcccggt | 540 |

```
ggccaagcag aacaaatgta cacccaatat ggacgtgaaa gagtatatct gaaacggcgc    600
aaaggatttt tgaagctttg cttgaagtac gagattccgg tcgtcccagc ttatgttttt    660
ggcgtatctg actattactt cacgtccgca aagctctttg gtctgcgaat gtggctcgtt    720
cagaatcttg gcattgctct tccactgtgc tggggaagat atggtctacc aatctgtcct    780
agaccagtcg ataccaccct tgtctttgac aaacctttat acctatcctg ccagaatccg    840
tcgaatccct cggaagacga ggttgacaag gctcatctgc aattttgcca agccctcgag    900
aagctgtttg atacacacaa agagaggctt gggtacggcg atcgaaagct ggaaataatt    960
tag                                                                  963
```